United States Patent
Yeo et al.

(10) Patent No.: US 11,197,883 B2
(45) Date of Patent: Dec. 14, 2021

(54) INHIBITION OF STRESS GRANULE FORMATION THROUGH MANIPULATION OF UBAP2L

(71) Applicant: The Regents of the University of California, Oakland, CA (US)

(72) Inventors: Eugene Yeo, La Jolla, CA (US); Sebastian Markmiller, La Jolla, CA (US); En-Ching Luo, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/431,486

(22) Filed: Jun. 4, 2019

(65) Prior Publication Data

US 2020/0030359 A1    Jan. 30, 2020

Related U.S. Application Data

(60) Provisional application No. 62/680,979, filed on Jun. 5, 2018.

(51) Int. Cl.
*A61K 31/7105* (2006.01)
*C12N 15/113* (2010.01)
*C12N 9/22* (2006.01)

(52) U.S. Cl.
CPC ......... *A61K 31/7105* (2013.01); *C12N 9/22* (2013.01); *C12N 15/113* (2013.01); *C12N 2310/11* (2013.01); *C12N 2310/14* (2013.01)

(58) Field of Classification Search
CPC ..... A61K 31/7105; C12N 9/22; C12N 15/113
See application file for complete search history.

(56) References Cited

FOREIGN PATENT DOCUMENTS

WO    WO-2016/210123 A1    12/2016

OTHER PUBLICATIONS

Fernandes (In RNA Metabolism in Neurodegenerative Diseases, Advances in Neurobiology 20, pp. 173-212, Jun. 19, 2018) (Year: 2018).*
Mensch et al (Exp. Neurol. 306: 222-231, 2018) (Year: 2018).*
Zhao et al (Mol. Cells 41(9): 818-829, 2018) (Year: 2018).*
Zhu et al (Proc. Nat. Acad. Sci. USA 115(18): 4661-4665, May 1, 2018) (Year: 2018).*
Khalfallah et al (Nature Scientific Reports 8:7551, 13 pages, May 15, 2018) (Year: 2018).*
Youn et al (Molecular Cell 69, 517-532 Feb. 1, 2018) (Year: 2018).*
Huang et al (Cell Death & Differentiation (2020) 27:227-241) (Year: 2020).*
Abudayyeh et al (Nature 550:281-284, Oct. 4, 2017) (Year: 2017).*
Aucagne, et al., "UBAP2L is amplified in a large subset of human lung adenocarcinoma and is critical for epithelial lung cell identity and tumor metastasis", The FASEB Journal, 2017, 31(11), pp. 5012-5018.
Becker, et al., "Therapeutic reduction of ataxin 2 extends lifespan and reduces pathology in TDP-43 mice", Nature, Apr. 20, 2020, 544(7650), pp. 367-371.
Blokhuis, et al., "Comparative interactomics analysis of different ALS-associated proteins identifies converging molecular pathways", Acta Neuropathol, 2016, 132, pp. 175-196.
Boutahar, et al., "Differential Effect of Oxidative or Excitotoxic Stress on the Transcriptional Profile of Amyotrophic Lateral Sclerosis-Linked Mutant SOD1 Cultured Neurons", Journal of Neuroscience Research, 2011, 89, pp. 1439-1450.
Chai, et al., "Depletion of UBA protein 2-like protein inhibits growth and induces apoptosis of human colorectal carcinoma cells", Tumor Biol., 2016, 37, p. 13225-13235.
Freibaum, et al., "Global analysis of TDP-43 interacting proteins reveals strong association with RNA splicing and translation machinery", J Proteome Res., 2010, Feb. 5, 2010, 9(2), pp. 1104-1120.
Maeda, et al., "Arginine methylation of ubiquitin-associated protein 2-like is required for the accurate distribution of chromosomes", The FASEB Journal, 2016, 30(1), pp. 312-323.
Markmiller, et al., "Context-Dependent and Disease-Specific Diversity in Protein Interactions within Stress Granules", Cell, Jan. 25, 2018, 172, pp. 590-604.
Markmiller, et al., "Proximity labeling reveals an extensive steady-state stress granule interactome and insights to neurodegeneration", bioRxiv, Jun. 20, 2017, 49 pages.
Scoles, et al., "Antisense oligonucleotide therapy for spinocerebellar ataxia type 2", Nature, Apr. 20, 2017, 544(7650), pp. 362-366.

\* cited by examiner

*Primary Examiner* — Richard A Schnizer
(74) *Attorney, Agent, or Firm* — Foley & Lardner LLP

(57) ABSTRACT

Disclosed herein are UBAP2L targeting agents and use of such agents for the treatment of a neurodegenerative disorder. Further disclosed herein are methods of monitoring the progression of a neurodegenerative disorder and methods of determining the efficacy of a neurodegenerative disorder therapy.

12 Claims, 12 Drawing Sheets

Specification includes a Sequence Listing.

SEQUENCE LISTING

<160> NUMBER OF SEQ ID NOS: 30

<210> SEQ ID NO 1
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccgggccaat actgatgata actatctcga gatagttatc atcagtattg gcttttt        57

<210> SEQ ID NO 2
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ccggcgcagc agaataccct ttcatctcga gatgaaaggg tattctgctg cgttttt        57

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cctcaaagtc agcatcatta                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

```
aagcaatcac acattcatcc                                                  20

<210> SEQ ID NO 5
<211> LENGTH: 3889
<212> TYPE: DNA
<213> ORGANISM: Homo sapiens

<400> SEQUENCE: 5
gagactgagt attctacctt gtaaatactg ttatttgtat atactgtaaa tgatgacatc       60
ggtgggcact aaccgagccc ggggaaactg ggaacaacct caaaaccaaa accagacaca      120
gcacaagcag cggccacagg ccactgcaga acaaattaga cttgcacaga tgatttcgga      180
ccataatgat gctgactttg aggagaaggt gaaacaattg attgatatta caggcaagaa      240
ccaggatgaa tgtgtgattg ctttgcatga ctgcaatgga gatgtcaaca gagctatcaa      300
tgttcttctg gaaggaaacc cagacacgca ttcctgggag atggtcggga agaagaaggg      360
agtctcaggc cagaaggatg gtggccagac ggaatccaat gaggaaggca agaaaatcg       420 agaccgggac agagactata gtcggcgacg tggtgggcca ccagacgggg gagaggtgc       480 cagccgtgga cgagagtttc gaggtcagga aaatggattg gatggcacca agagtggagg      540
gccttctgga agaggaacag aaagaggcag aaggggccgt ggccgaggca gaggtggctc      600
tggtaggcga ggaggaaggt tttctgctca aggaatggga acctttaacc cagctgatta      660
tgcagagcca gccaatactg atgataacta tggcaatagc agcggcaata cgtggaacaa      720
cactggccac tttgaaccag atgatgggac gagtgcatgg aggactgcaa cagaggagtg      780
ggggactgaa gattggaatg aagatctttc tgagaccaag atcttcactg cctctaatgt      840
gtcttcagtg cctctgcctg cggagaatgt gacaatcact gctggtcaga gaattgacct      900
tgctgttctg ctggggaaga caccatctac aatggagaat gattcatcta atctggatcc      960
gtctcaggct ccttctctgg cccagcctct ggtgttcagt aattcgaagc agactgccat     1020
atcacagcct gcttcaggga cacatttttc tcatcacagt atggtgagca tgttagggaa     1080
aggatttggt gatgtcggtg aagctaaagg cggcagtact acaggctccc agttcttgga     1140
gcaattcaag actgcccaag ccctggctca gttggcagct cagcattctc agtctggaag     1200
caccaccacc tcctcttggg acatgggctc gacgacacaa tccccatcac tggtgcagta     1260
tgatttgaag aacccaagtg attcagcagt gcacagcccc tttacaaagc gccaggcttt     1320
taccccatct tcaaccatga tggaggtgtt ccttcaggag aagtcacctg cagtggctac     1380
ctccacagct gcacctccac ctccgtcttc tcctctgcca agcaaatcca tcggctcc       1440 acagatgtcg cctggatctt cagacaacca gtcctctagc cctcagccgg ctcaccagaa     1500
actgaaacag cagaagaaaa aagcctcctt gacttctaag attcctgctc tggctgtgga     1560
gatgcctggc tcagcagata tctcagggct aaacctgcag tttggggcat gcagtttgg       1620 gtcagagcct gtcctttctg attatgagtc caccccacc acgagcgcct cttcaagcca     1680
ggctccaagt agcctgtata ccagcacggc cagtgaatca tcctctacaa tttcatctaa     1740
ccagagtcag gagtctggtt atcagagcgg cccaattcag tcgacaacct atacctccca     1800
aaataatgct cagggccctc tttatgaaca gagatccaca cagactcggc ggtaccccag     1860
ctccatctct tcatcacccc aaaaggacct gactcaggca agaatggct tcagttctgt       1920 gcaggccacg cagttacaga ccacacaatc tgttgaaggt gctacaggct gcagtgaa       1980 atctgattca ccttccactt ctagcatccc ccctctcaat gaaacggtat ctgcagcttc     2040
cttactgacg acaaccaatc agcattcatc ctccttgggt ggcttgagcc acagtgagga     2100
```

-continued

```
gattccaaat actaccacca cacaacacag cagcacgtta tctacgcagc agaataccct    2160
ttcatcatca acatcttctg ggcgcacttc gacatccact cttttgcaca caagtgtgga    2220
gagtgaggcg aatctccatt cttcctccag cacttttcc accacatcca gcacagtctc     2280
tgcacctccc ccagtggtca gtgtctcctc cagtctcaat agtggcagta gcctgggcct    2340
cagcctaggc agcaactcca ctgtcacagc ctcgactcga agctcagttg ctacgacttc    2400
aggaaaagct cctcccaacc tcctcctgg ggtcccgccg ttgttgccta atccgtatat     2460
tatggctcca gggctgttac atgcctaccc gccacaagta tatggttatg atgacttgca   2520
gatgcttcag acaagatttc cattggatta ctacagcatc ccatttccca cacccactac   2580
tccgctgact gggagggatg gtagcctggc cagcaaccct tattctggtg acctcacaaa   2640
gttcggccgt ggggatgcct cctcccagc ccggccaca accttggccc aaccccaaca     2700
gaaccagacg cagactcacc ataccacgca gcagacattc ctgaacccgg cgctgcctcc   2760
tggctacagt tacaccagcc tgccatacta tacaggggtc ccgggcctcc ccagcacctt   2820
ccagtatggg cctgctgtgt tccctgtggc tcctacctct tccaagcagc atggtgtgaa   2880
tgtcagtgtg aatgcatcgg ccaccccttt ccaacagccg agtggatatg ggtctcatgg   2940
atacaacact ggtgtttcag tcacctccag taacacgggc gtgccagata tctcgggttc   3000
tgtgtactcc aaaacccagc agtcctttga gaaacaaggt tttcattccg gtactcctgc   3060
tgcttccttc aacttgcctt cagccctagg aagtgggggc cccatcaatc cggccacagc   3120
tgctgcctac ccacctgccc cctttatgca cattctgacc ccccatcagc agccgcattc   3180
tcagatcctt caccatcacc tgcagcagga tggccagacg ggcagcgggc aacgtagcca   3240
gaccagctcc atcccgcaga agccccagac caacaagtct gcctacaaca gctacagctg   3300
gggggccaac tgaggccctg accctcttct cccggtccca tcttctgaga gggcttctca   3360
gcctggaaac tatggaaaca gcatcaaaga gaaggaatg tggggggttt ccgctgcccc    3420 ccaccccag cggcccaccc catgcctcag cttcatgtct gtcccattcc tataccatcc    3480
ccaccctgtt gtatgtatta taggatttgt atttctcct ttttttccc ccttccattc     3540 cttctcccct cttgcattca agattatgaa actttgctat gggccctgca cttcctttgc   3600
ttcctcctgt tcaccctggt ggtgtacgga tgaggcgggg aggtgggacc cccaaacata   3660
tatcagccca acagccctaa gtctccttct ttattattag gaaaacaaca acaacaacaa   3720
acaaaaaaat ggcgtcatga atatgaacag cattgtcaga tgaattagtt gaagtggttt   3780
tttttttgtt tttttttttt tttttgtact gtgtcctcaa atttaatgga ttaatgtgtc   3840
ttgtatatat aaaaagaaaa cctctacctt caaaaaaaaa aaaaaaaaa                3889
```

<210> SEQ ID NO 6
<211> LENGTH: 1087
<212> TYPE: PRT
<213> ORGANISM: Homo sapiens

<400> SEQUENCE: 6

```
Met Met Thr Ser Val Gly Thr Asn Arg Ala Arg Gly Asn Trp Glu Gln
1               5                   10                  15

Pro Gln Asn Gln Asn Gln Thr Gln His Lys Gln Arg Pro Gln Ala Thr
            20                  25                  30

Ala Glu Gln Ile Arg Leu Ala Gln Met Ile Ser Asp His Asn Asp Ala
        35                  40                  45

Asp Phe Glu Glu Lys Val Lys Gln Leu Ile Asp Ile Thr Gly Lys Asn
```

```
                50                  55                  60
        Gln Asp Glu Cys Val Ile Ala Leu His Asp Cys Asn Gly Asp Val Asn
        65                  70                  75                  80

Arg Ala Ile Asn Val Leu Leu Glu Gly Asn Pro Asp Thr His Ser Trp
                            85                  90                  95

Glu Met Val Gly Lys Lys Gly Val Ser Gly Gln Lys Asp Gly Gly
                        100                 105                 110

Gln Thr Glu Ser Asn Glu Glu Gly Lys Glu Asn Arg Asp Arg Asp Arg
                    115                 120                 125

Asp Tyr Ser Arg Arg Arg Gly Gly Pro Pro Arg Arg Gly Arg Gly Ala
                130                 135                 140

Ser Arg Gly Arg Glu Phe Arg Gly Gln Glu Asn Gly Leu Asp Gly Thr
        145                 150                 155                 160

Lys Ser Gly Gly Pro Ser Gly Arg Gly Thr Glu Arg Gly Arg Arg Gly
                        165                 170                 175

Arg Gly Arg Gly Arg Gly Ser Gly Arg Arg Gly Gly Arg Phe Ser
                    180                 185                 190

Ala Gln Gly Met Gly Thr Phe Asn Pro Ala Asp Tyr Ala Glu Pro Ala
                195                 200                 205

Asn Thr Asp Asp Asn Tyr Gly Asn Ser Ser Gly Asn Thr Trp Asn Asn
            210                 215                 220

Thr Gly His Phe Glu Pro Asp Asp Gly Thr Ser Ala Trp Arg Thr Ala
        225                 230                 235                 240

Thr Glu Glu Trp Gly Thr Glu Asp Trp Asn Glu Asp Leu Ser Glu Thr
                        245                 250                 255

Lys Ile Phe Thr Ala Ser Asn Val Ser Ser Val Pro Leu Pro Ala Glu
                        260                 265                 270

Asn Val Thr Ile Thr Ala Gly Gln Arg Ile Asp Leu Ala Val Leu Leu
                    275                 280                 285

Gly Lys Thr Pro Ser Thr Met Glu Asn Asp Ser Ser Asn Leu Asp Pro
                290                 295                 300

Ser Gln Ala Pro Ser Leu Ala Gln Pro Leu Val Phe Ser Asn Ser Lys
        305                 310                 315                 320

Gln Thr Ala Ile Ser Gln Pro Ala Ser Gly Asn Thr Phe Ser His His
                            325                 330                 335

Ser Met Val Ser Met Leu Gly Lys Gly Phe Gly Asp Val Gly Glu Ala
                        340                 345                 350

Lys Gly Gly Ser Thr Thr Gly Ser Gln Phe Leu Glu Gln Phe Lys Thr
                    355                 360                 365

Ala Gln Ala Leu Ala Gln Leu Ala Ala Gln His Ser Gln Ser Gly Ser
                370                 375                 380

Thr Thr Thr Ser Ser Trp Asp Met Gly Ser Thr Thr Gln Ser Pro Ser
        385                 390                 395                 400

Leu Val Gln Tyr Asp Leu Lys Asn Pro Ser Asp Ser Ala Val His Ser
                            405                 410                 415

Pro Phe Thr Lys Arg Gln Ala Phe Thr Pro Ser Ser Thr Met Met Glu
                        420                 425                 430

Val Phe Leu Gln Glu Lys Ser Pro Ala Val Ala Thr Thr Ala Ala
                    435                 440                 445

Pro Pro Pro Pro Ser Ser Pro Leu Pro Ser Lys Ser Thr Ser Ala Pro
                450                 455                 460

Gln Met Ser Pro Gly Ser Ser Asp Asn Gln Ser Ser Ser Pro Gln Pro
        465                 470                 475                 480
```

```
Ala His Gln Lys Leu Lys Gln Gln Lys Lys Ala Ser Leu Thr Ser
            485                 490                 495

Lys Ile Pro Ala Leu Ala Val Glu Met Pro Gly Ser Ala Asp Ile Ser
            500                 505                 510

Gly Leu Asn Leu Gln Phe Gly Ala Leu Gln Phe Gly Ser Glu Pro Val
            515                 520                 525

Leu Ser Asp Tyr Glu Ser Thr Pro Thr Thr Ser Ala Ser Ser Ser Gln
            530                 535                 540

Ala Pro Ser Ser Leu Tyr Thr Ser Thr Ala Ser Glu Ser Ser Ser Thr
545                 550                 555                 560

Ile Ser Ser Asn Gln Ser Gln Glu Ser Gly Tyr Gln Ser Gly Pro Ile
            565                 570                 575

Gln Ser Thr Thr Tyr Thr Ser Gln Asn Asn Ala Gln Gly Pro Leu Tyr
            580                 585                 590

Glu Gln Arg Ser Thr Gln Thr Arg Arg Tyr Pro Ser Ser Ile Ser Ser
            595                 600                 605

Ser Pro Gln Lys Asp Leu Thr Gln Ala Lys Asn Gly Phe Ser Ser Val
            610                 615                 620

Gln Ala Thr Gln Leu Gln Thr Thr Gln Ser Val Glu Gly Ala Thr Gly
625                 630                 635                 640

Ser Ala Val Lys Ser Asp Ser Pro Ser Thr Ser Ser Ile Pro Pro Leu
            645                 650                 655

Asn Glu Thr Val Ser Ala Ala Ser Leu Leu Thr Thr Asn Gln His
            660                 665                 670

Ser Ser Ser Leu Gly Gly Leu Ser His Ser Glu Glu Ile Pro Asn Thr
            675                 680                 685

Thr Thr Thr Gln His Ser Ser Thr Leu Ser Thr Gln Gln Asn Thr Leu
            690                 695                 700

Ser Ser Ser Thr Ser Ser Gly Arg Thr Ser Thr Ser Thr Leu Leu His
705                 710                 715                 720

Thr Ser Val Glu Ser Glu Ala Asn Leu His Ser Ser Ser Ser Thr Phe
            725                 730                 735

Ser Thr Ser Ser Thr Val Ser Ala Pro Pro Val Val Ser Val
            740                 745                 750

Ser Ser Ser Leu Asn Ser Gly Ser Ser Leu Gly Leu Ser Leu Gly Ser
            755                 760                 765

Asn Ser Thr Val Thr Ala Ser Thr Arg Ser Ser Val Ala Thr Thr Ser
            770                 775                 780

Gly Lys Ala Pro Pro Asn Leu Pro Pro Gly Val Pro Pro Leu Leu Pro
785                 790                 795                 800

Asn Pro Tyr Ile Met Ala Pro Gly Leu Leu His Ala Tyr Pro Pro Gln
            805                 810                 815

Val Tyr Gly Tyr Asp Asp Leu Gln Met Leu Gln Thr Arg Phe Pro Leu
            820                 825                 830

Asp Tyr Tyr Ser Ile Pro Phe Pro Thr Pro Thr Pro Leu Thr Gly
            835                 840                 845

Arg Asp Gly Ser Leu Ala Ser Asn Pro Tyr Ser Gly Asp Leu Thr Lys
850                 855                 860

Phe Gly Arg Gly Asp Ala Ser Ser Pro Ala Pro Ala Thr Thr Leu Ala
865                 870                 875                 880

Gln Pro Gln Gln Asn Gln Thr Gln Thr His His Thr Thr Gln Gln Thr
            885                 890                 895
```

```
Phe Leu Asn Pro Ala Leu Pro Pro Gly Tyr Ser Tyr Thr Ser Leu Pro
            900                 905                 910

Tyr Tyr Thr Gly Val Pro Gly Leu Pro Ser Thr Phe Gln Tyr Gly Pro
        915                 920                 925

Ala Val Phe Pro Val Ala Pro Thr Ser Ser Lys Gln His Gly Val Asn
    930                 935                 940

Val Ser Val Asn Ala Ser Ala Thr Pro Phe Gln Gln Pro Ser Gly Tyr
945                 950                 955                 960

Gly Ser His Gly Tyr Asn Thr Gly Val Ser Val Thr Ser Ser Asn Thr
                965                 970                 975

Gly Val Pro Asp Ile Ser Gly Ser Val Tyr Ser Lys Thr Gln Gln Ser
            980                 985                 990

Phe Glu Lys Gln Gly Phe His Ser Gly Thr Pro Ala Ala Ser Phe Asn
        995                 1000                1005

Leu Pro Ser Ala Leu Gly Ser Gly Gly Pro Ile Asn Pro Ala Thr
    1010                1015                1020

Ala Ala Ala Tyr Pro Pro Ala Pro Phe Met His Ile Leu Thr Pro
    1025                1030                1035

His Gln Gln Pro His Ser Gln Ile Leu His His His Leu Gln Gln
    1040                1045                1050

Asp Gly Gln Thr Gly Ser Gly Gln Arg Ser Gln Thr Ser Ser Ile
    1055                1060                1065

Pro Gln Lys Pro Gln Thr Asn Lys Ser Ala Tyr Asn Ser Tyr Ser
    1070                1075                1080

Trp Gly Ala Asn
    1085

<210> SEQ ID NO 7
<211> LENGTH: 267
<212> TYPE: DNA
<213> ORGANISM: Homo sapiens

<400> SEQUENCE: 7
caaaaccaga cacagcacaa gcagcggcca caggccactg cagaacaaat tagacttgca      60
cagatgattt cggaccataa tgatgctgac tttgaggaga aggtgaaaca attgattgat     120
attacaggca agaaccagga tgaatgtgtg attgcttttgc atgactgcaa tggagatgtc     180
aacagagcta tcaatgttct tctggaagga aacccagaca cgcattcctg ggagatggtc     240
gggaagaaga agggagtctc aggccag                                         267

<210> SEQ ID NO 8
<211> LENGTH: 89
<212> TYPE: PRT
<213> ORGANISM: Homo sapiens

<400> SEQUENCE: 8

Gln Asn Gln Thr Gln His Lys Gln Arg Pro Gln Ala Thr Ala Glu Gln
1               5                   10                  15

Ile Arg Leu Ala Gln Met Ile Ser Asp His Asn Asp Ala Asp Phe Glu
            20                  25                  30

Glu Lys Val Lys Gln Leu Ile Asp Ile Thr Gly Lys Asn Gln Asp Glu
        35                  40                  45

Cys Val Ile Ala Leu His Asp Cys Asn Gly Asp Val Asn Arg Ala Ile
    50                  55                  60

Asn Val Leu Leu Glu Gly Asn Pro Asp Thr His Ser Trp Glu Met Val
65                  70                  75                  80
```

Gly Lys Lys Lys Gly Val Ser Gly Gln
                85

<210> SEQ ID NO 9
<211> LENGTH: 168
<212> TYPE: DNA
<213> ORGANISM: Homo sapiens

<400> SEQUENCE: 9
cgtggtgggc caccaagacg ggggagaggt gccagccgtg gacgagagtt tcgaggtcag        60
gaaaatggat tggatggcac caagagtgga gggccttctg gaagaggaac agaaagaggc       120
agaaggggcc gtggccgagg cagaggtggc tctggtaggc gaggagga                    168

<210> SEQ ID NO 10
<211> LENGTH: 56
<212> TYPE: PRT
<213> ORGANISM: Homo sapiens

<400> SEQUENCE: 10

Arg Gly Gly Pro Pro Arg Arg Gly Arg Gly Ala Ser Arg Gly Arg Glu
1               5                   10                  15

Phe Arg Gly Gln Glu Asn Gly Leu Asp Gly Thr Lys Ser Gly Gly Pro
            20                  25                  30

Ser Gly Arg Gly Thr Glu Arg Gly Arg Arg Gly Arg Gly Arg Gly Arg
        35                  40                  45

Gly Gly Ser Gly Arg Arg Gly Gly
    50                  55

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cacctcatgc agccatacaa accc                                              24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaacgggttt gtatggctgc atga                                              24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cacctccatg aagattcact gccg                                              24

<210> SEQ ID NO 14

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aaaccggcag tgaatcttca tgga                                          24

<210> SEQ ID NO 15
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tcagagcaga ttgtactgag agtgcaccat atgtccccgg cccttagttt gctagtcct    59

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tgctatacga agttatcgta gaatcgagac cgaggagagg gttagggata ggcttaccga   60

<210> SEQ ID NO 17
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cggcatggac gagctgtaca agtaagtcga catcttcatg gatcttcatg cagccataca   60

<210> SEQ ID NO 18
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agctatgacc atgattacgc caagcttgca tgcccatcaa taaaagagaa ccataac      57

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
agccactgaa gaacccagaa                                               20

<210> SEQ ID NO 20
<211> LENGTH: 60
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ggggacaagt ttgtacaaaa aagcaggctt caccatgatg acatcggtgg gcactaaccg      60

<210> SEQ ID NO 21
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggggaccact ttgtacaaga aagctgggtt ttacttgtag agctcgtcca tgccg           55

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aaggatggtg gccagac                                                     17

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gttttgaggt tgttcccag                                                   19

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tctgctcaag gaatgggaac                                                  20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
acagatgtcg cctggatctt                                                  20

<210> SEQ ID NO 26
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 26
tccattcttc ctccagcact                                                    20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tccttcaact tgccttcagc                                                    20

<210> SEQ ID NO 28
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aacaagatga agagcaccaa ctcgagttgg tgctcttcat cttgtt                       46

<210> SEQ ID NO 29
<211> LENGTH: 4
<212> TYPE: PRT
<213> ORGANISM: Unknown
<220> FEATURE:
<223> OTHER INFORMATION: Description of Unknown:
      DEAD-box helicase peptide

<400> SEQUENCE: 29

Asp Glu Ala Asp
1

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gly Gly Gly Ser Gly Gly Gly Gly Ser
1               5                   10
```

INHIBITION OF STRESS GRANULE FORMATION THROUGH MANIPULATION OF UBAP2L

CROSS-REFERENCE TO RELATED APPLICATION

This application claims priority under 35 U.S.C. § 119(e) to U.S. Provisional Application No. 62/680,979, filed Jun. 5, 2018, the content of which is hereby incorporated by reference in its entirety.

STATEMENT OF GOVERNMENT SUPPORT

This invention was made with government support under the Grant Nos. NS075449, NS1013172, and HG004659 awarded by the National Institute for Health (NIH). The government has certain rights to the invention.

SEQUENCE LISTING

The instant application contains a Sequence Listing which has been filed electronically in ASCII format and is hereby incorporated by reference in its entirety. Said ASCII copy, created on Aug. 13, 2019, is named 114198-0261_SL.txt and is 22,500 bytes in size.

BACKGROUND

Cellular RNA molecules interact with a diverse array of nearly 2,000 RNA-binding proteins (RBPs) to form ribonucleoprotein particles (RBPs). Large numbers of RBPs frequently accumulate into microscopically visible RBP granules, which can measure up to several microns in size but remain highly dynamic. Neuronal transport granules, which mediate the transport of mRNA and other cargo along axons and dendrites, are an example of RBP granules that are present in cells under physiological conditions. By contrast, exposure of cells to exogenous stresses can induce the rapid formation of cytoplasmic stress granules (SGs) and other induced RBP granules. The formation of SGs occurs concurrently with alterations in global RNA metabolism, primarily a near-complete shutdown in translation through sequestration of untranslated mRNAs within stalled translation initiation complexes.

SG formation has been suggested as a two-step process, with initial formation of a dense stable SG "core" followed by accumulation of proteins containing intrinsically disordered regions (IDRs) and low-complexity domains (LCDs) into a peripheral "shell" through a process involving liquid-liquid phase separation (LLPS). Recently, SGs have been associated with human neurodegenerative disorders characterized by the presence of toxic insoluble protein aggregates. This link is most compelling in the case of amyotrophic lateral sclerosis (ALS) and frontotemporal dementia (FTD), where numerous disease-causing mutations are purported to interfere with LLPS-dependent growth and dynamics of SGs. A more complete description of how SG composition and behavior are affected in normal and disease conditions is required for the potential development of SG-targeting therapies. In vivo approaches are needed that address potential loss or gain of SG protein interactions following cell lysis. Furthermore, there is an unmet need to systematically examine the extent to which SG composition is dependent on cell type, the nature of the stressor, and the presence of disease-linked mutations in SG proteins. This disclosure satisfies this need and provides related advantages.

SUMMARY

Disclosed herein are methods for inhibiting the formation of a toxic insoluble protein aggregate stress granule (SG), comprising, consisting of, or consisting essentially of contacting a cell or tissue with an effective amount of ubiquitin associated protein 2-like ("UBAP2L") in a mammalian neuronal cell. Generally, the method comprises, or consists essentially of, or yet further consists of, contacting the cell with an effective amount of an ubiquitin associated protein 2-like (UBAP2L) targeting agent that specifically targets one or more regions within an UBAP2L protein, mRNA, or gene.

In some embodiments, the UBAP2L protein comprises, or consists essentially of, or consists of, or has the amino acid sequence of SEQ ID NO: 6 or an equivalent thereof. In some embodiments, the UBAP2L mRNA comprises, or consists essentially of, or consists of, or has the nucleotide sequence of SEQ ID NO: 5 or an equivalent thereof. In some embodiments, the UBAP2L gene comprises, or consists essentially of, or consists of, or has the nucleotide sequence of NCBI Reference No. NC_000001.11, or an equivalent thereof or encodes SEQ ID NOS: 5 or 6, or an equivalent of each thereof.

In some embodiments, the UBAP2L targeting agent specifically targets one or more regions within bases 617 to 3889 of an UBAP2L messenger RNA (mRNA) molecule having a nucleotide sequence of SEQ ID NO: 5 or an equivalent thereof. In some embodiments, the UBAP2L targeting agent specifically hybridizes to one or more regions within bases 617 to 3889 of an UBAP2L messenger RNA (mRNA) molecule having a nucleotide sequence of SEQ ID NO: 5 or an equivalent thereof.

In some embodiments, the UBAP2L targeting agent specifically targets one or more regions within the UBAP2L gene having the nucleotide sequence of NCBI Reference No. NC_000001.11 or an equivalent thereof.

In some embodiments, the UBAP2L targeting agent does not bind to a region of the UBAP2L that corresponds to the ubiquitin associated (UBA) domain. In some embodiments, the UBA domain comprises, or consists essentially of, or yet further consists of, or has a nucleotide sequence of SEQ ID NO: 7 or an equivalent thereof. In some embodiments, the UBA domain comprises, or consists essentially of, or yet further consists of or has an amino acid sequence of SEQ ID NO: 8, or an equivalent thereof.

In some embodiments, the UBAP2L targeting agent does not bind to a region of the UBAP2L that corresponds to the glycine-rich motif (RGG domain). In some embodiments, the UBA domain comprises, or consists essentially of, or yet further consists of, or has a nucleotide sequence of SEQ ID NO: 9 or an equivalent thereof. In some embodiments, the UBA domain comprises, or consists essentially of, or yet further consists of, or has an amino acid sequence of SEQ ID NO: 10 or an equivalent thereof.

In some embodiments, the contacting is in vivo. Alternatively, the contacting is in vitro. In a further embodiment, the contacting is in vivo, by administration of an effective amount of the agent to a subject in need thereof.

In some embodiments, the mammalian neuronal cell is a cell of the group of spinal group neuron and brain neuron. In some embodiments, the spinal group neuron is a neuron of the group of sensory neuron, motor neuron, and interneurons. In some embodiments, the spinal group neuron is a motor neuron.

In some embodiments, the method further comprises, or further consists essentially of, or yet further consists of, subjecting the cell to an environmental stressor. In some embodiments, the environmental stressor is selected from the group of temperature, exposure to a toxin, and mechanical damage. In some embodiments, the environmental stressor is an increase in temperature. In some embodiments, the environmental stresser is exposure to a toxin. In some embodiments, the toxin is selected from sodium arsenite and thapsigargin.

In some embodiments, the method further comprises, or further consists essentially of, or yet further consists of, detecting SG formation. In some embodiments, detecting SG formation comprises, further consists essentially of, or yet further consists of, immunofluorescence imaging. In some embodiments, detecting SG formation comprises, further consists essentially of, or yet further consists of, contacting the cell with an antibody that binds to a RNA binding protein (RBP). In some embodiments, the RBP is G3BP Stress Granule Assembly Factor 1 (G3BP1) or Fragile X Mental Retardation 1 (FMR1), or an equivalent thereof.

In some embodiments, the method further comprises, or further consists essentially of, or yet further consists of, detecting the expression level of UBAP2L. In some embodiments, the method further comprises, or further consists essentially of, or yet further consists of, detecting the expression level of one or more RNA binding proteins (RBPs).

In some embodiments, the expression level of UBAP2L or the RBPs is detected in a sample from the subject. In some embodiments, the sample comprises, or consists essentially of, or yet further consists of, a bodily fluid. Alternatively, the sample comprises, or consists essentially of, or yet further consists of, a tissue or cell.

In some embodiments, the UBAP2L targeting agent that specifically targets a UBAP2L protein, mRNA, or gene is selected from the group of: an antisense oligonucleotide (ASO) that hybridizes to a region within an UBAP2L messenger RNA (mRNA) molecule; a RNA interference (RNAi) molecule that hybridizes to a region within an UBAP2L messenger RNA (mRNA) molecule; and a Clustered Regularly Interspaced Short Palindromic Repeat (CRISPR) system that targets a region within an UBAP2L messenger RNA (mRNA) molecule.

In some embodiments, the ubiquitin associated protein 2-like (UBAP2L) targeting agent that specifically targets one or more regions within an UBAP2L protein, mRNA, or gene is selected from the group of: an antisense oligonucleotide (ASO) that hybridizes to a region within an UBAP2L messenger RNA (mRNA) molecule comprising, or consisting essentially of, or yet further consisting of, SEQ ID NO: 5 or an equivalent thereof; a RNA interference (RNAi) molecule that hybridizes to a region within an UBAP2L messenger RNA (mRNA) molecule comprising, or consisting essentially of, or yet further consisting of, SEQ ID NO: 5 or an equivalent thereof; and a Clustered Regularly Interspaced Short Palindromic Repeat (CRISPR) system that targets a nucleic acid molecule comprising, or consisting essentially of, or yet further consisting of, a nucleotide sequence of SEQ ID NO: 5 or an equivalent thereof.

In some embodiments, the UBAP2L targeting agent that specifically targets a UBAP2L protein, mRNA, or gene is selected from the group of: an antisense oligonucleotide (ASO) that hybridizes to a region within an UBAP2L gene; a RNA interference (RNAi) molecule that hybridizes to a region within an UBAP2L gene; and a Clustered Regularly Interspaced Short Palindromic Repeat (CRISPR) system that targets a region within an UBAP2L gene.

In some embodiments, the CRISPR system comprises, or consists essentially of, or yet further consists of: (a) an oligonucleotide encoding a CRISPR associated endonuclease (Cas) protein; and (b) an oligonucleotide comprising, or consisting essentially of, or yet further consisting of, (i) a first region that hybridizes to an ubiquitin associated protein 2-like (UBAP2L) gene; and (ii) a scaffold sequence.

Also disclosed herein are methods for treating a neurodegenerative disorder in a subject in need thereof. Generally, the method comprises, or consists essentially of, or yet further consists of, administering to the subject an effective amount of an ubiquitin associated protein 2-like (UBAP2L) targeting agent that specifically targets one or more regions within an UBAP2L protein, mRNA, or gene.

In some embodiments, the subject is a mammal. In some embodiments, the mammal is of the group of human, non-human primate, rat, mouse, cow, pig, rabbit, horse, and goat. In some embodiments, the mammal is a human.

In some embodiments, the UBAP2L targeting agent is selected from the group of: an antisense oligonucleotide (ASO) that hybridizes to a region within an UBAP2L messenger RNA (mRNA) molecule; a RNA interference (RNAi) molecule that hybridizes to a region within an UBAP2L messenger RNA (mRNA) molecule; and a Clustered Regularly Interspaced Short Palindromic Repeat (CRISPR) system that targets to a region within an UBAP2L messenger RNA (mRNA) molecule.

In some embodiments, the UBAP2L targeting agent is selected from the group of: an antisense oligonucleotide (ASO) that targets an UBAP2L messenger RNA (mRNA) molecule; a RNA interference (RNAi) molecule that targets an UBAP2L messenger RNA (mRNA) molecule; and a Clustered Regularly Interspaced Short Palindromic Repeat (CRISPR) system that targets an UBAP2L messenger RNA (mRNA) molecule.

In some embodiments, the UBAP2L targeting agent is selected from the group of: an antisense oligonucleotide (ASO) that hybridizes to a region within an UBAP2L gene; a RNA interference (RNAi) molecule that hybridizes to a region within an UBAP2L gene; and a Clustered Regularly Interspaced Short Palindromic Repeat (CRISPR) system that targets to a region within an UBAP2L gene.

In some embodiments, the UBAP2L targeting agent is selected from the group of: an antisense oligonucleotide (ASO) that targets an UBAP2L gene; a RNA interference (RNAi) molecule that targets an UBAP2L gene; and a Clustered Regularly Interspaced Short Palindromic Repeat (CRISPR) system that targets an UBAP2L gene.

In some embodiments, the CRISPR system comprises, or consists essentially of, or yet further consists of: (a) an oligonucleotide encoding a CRISPR associated endonuclease (Cas) protein; and (b) an oligonucleotide comprising, or consisting essentially of, or yet further consisting of, (i) a first region that hybridizes to an ubiquitin associated protein 2-like (UBAP2L) gene; and (ii) a scaffold sequence.

In some embodiments, the ASO and/or RNAi molecule hybridizes to bases 617 to 3889 of an UBAP2L messenger RNA (mRNA) molecule comprising, or consisting essentially of, or yet further consisting of, the nucleotide sequence of SEQ ID NO: 5 or an equivalent thereof. In some embodiments, the ASO and/or RNAi molecule does not hybridize to a region of the UBAP2L mRNA molecule that encodes for an ubiquitin associated (UBA) domain or arginine and glycine-rich motif (RGG domain).

In some embodiments, the ASO and/or RNAi molecule does not hybridize to a region of the UBAP2L gene that encodes for an ubiquitin associated (UBA) domain or arginine and glycine-rich motif (RGG domain).

In some embodiments, the RNAi molecule is selected from a microRNA (miRNA) or small interfering RNA (siRNA). In some embodiments, the RNAi molecule comprises, or consists essentially of, or consists of, or has the nucleotide sequence of SEQ ID NO: 1 or SEQ ID NO: 2, or an equivalent of each thereof.

In some embodiments, the UBAP2L targeting agent is a CRISPR system. In some embodiments, the first region of the CRISPR system does not hybridize to a region of the UBAP2L gene that encodes for an ubiquitin associated (UBA) domain or arginine and glycine-rich motif (RGG domain). In some embodiments, the Cas protein is a Cas9 protein.

In some embodiments, the subject has been identified for treatment by detecting expression of UBAP2L in a neuronal sample isolated from the subject.

In some embodiments, the neurodegenerative disorder is characterized by the formation of stress granules. In some embodiments, the neurodegenerative disorder is amyotrophic lateral sclerosis (ALS) or dementia. In some embodiments, the dementia is selected from Alzheimer's disease (AD), frontotemporal lobar degeneration (FTLD), or Lewy body dementia (LBD). In some embodiments, the LBD is selected from dementia with Lewy bodies and Parkinson's disease dementia.

Further disclosed herein are methods of monitoring disease progression in a subject suffering from a neurodegenerative disorder. Generally, the method comprises, or consists essentially of, or yet further consists of, (a) analyzing at least two biological samples taken from the subject at different time points to detect level of expression of ubiquitin associated protein 2-like (UBAP2L); and (b) comparing the detected UBAP2L expression level in the biological samples taken at different time points.

In some embodiments, an increase in the detected UBAP2L expression level over time is indicative that the subject's neurodegenerative disorder is progressing.

In some embodiments, a decrease in the detected UBAP2L expression level over time is indicative that the subject's neurodegenerative is not progressing.

Also disclosed herein are methods of determining the efficacy of a neurodegenerative disorder therapy in a subject suffering from a neurodegenerative disorder. Generally, the method comprises, or consists essentially of, or yet further consists of, (a) administering an effective amount of the neurodegenerative disorder therapy; and (b) analyzing at least two biological samples taken from the subject before and after administration of the neurodegenerative disorder therapy for the level of expression of ubiquitin associated protein 2-like (UBAP2L).

In some embodiments, an increase in the detected UBAP2L expression level over time is indicative that the subject's neurodegenerative disorder is progressing.

In some embodiments, a decrease in the detected UBAP2L expression level over time is indicative that the subject's neurodegenerative is not progressing.

In some embodiments, the neurodegenerative disorder is characterized by the formation of stress granules. In some embodiments, the neurodegenerative disorder is amyotrophic lateral sclerosis (ALS) or dementia. In some embodiments, the dementia is selected from Alzheimer's disease (AD), frontotemporal lobar degeneration (FTLD), or Lewy body dementia (LBD). In some embodiments, the LBD is selected from dementia with Lewy bodies and Parkinson's disease dementia.

Disclosed herein is an antisense oligonucleotide (ASO) that hybridizes to a region within a mRNA encoding an ubiquitin associated protein 2-like (UBAP2L) protein.

Also disclosed herein is an antisense oligonucleotide (ASO) that hybridizes to a region within a mRNA encoding an ubiquitin associated protein 2-like (UBAP2L) protein, wherein the ASO does not hybridize to a region of the mRNA that encodes for an ubiquitin associated (UBA) domain or arginine and glycine-rich motif (RGG domain).

Further disclosed herein is a vector comprising, or consisting essentially of, or yet further consisting of, an antisense oligonucleotide (ASO) that hybridizes to a region within a mRNA encoding an ubiquitin associated protein 2-like (UBAP2L) protein, wherein the ASO is optionally linked to expression and/or regulatory elements.

Further disclosed herein is a vector comprising, or consisting essentially of, or yet further consisting of, an antisense oligonucleotide (ASO) that hybridizes to a region within a mRNA encoding an ubiquitin associated protein 2-like (UBAP2L) protein, wherein the ASO does not hybridize to a region of the mRNA that encodes for an ubiquitin associated (UBA) domain or arginine and glycine-rich motif (RGG domain), wherein the ASO is optionally linked to expression and/or regulatory elements.

Further disclosed herein is a RNA interference (RNAi) molecule comprising, or consisting essentially of, or yet further consisting of, the oligonucleotide sequence of SEQ ID NO: 1 or SEQ ID NO: 2, or an equivalent of each thereof.

Further disclosed herein is a RNA interference (RNAi) molecule that hybridizes to a region within mRNA encoding an ubiquitin associated protein 2-like (UBAP2L) protein, wherein the RNAi molecule does not hybridize to a region of the mRNA that encodes for an ubiquitin associated (UBA) domain or arginine and glycine-rich motif (RGG domain).

Further disclosed herein is a vector comprising, or consisting essentially of, or yet further consisting of, a RNA interference (RNAi) molecule comprising, or consisting essentially of, or yet further consisting of, the oligonucleotide sequence of SEQ ID NO: 1 or SEQ ID NO: 2 or an equivalent of each thereof, wherein the RNAi molecule is optionally linked to expression and/or regulatory elements.

Further disclosed herein is a vector comprising, or consisting essentially of, or yet further consisting of, a RNA interference (RNAi) molecule that hybridizes to region within a mRNA encoding an ubiquitin associated protein 2-like (UBAP2L) protein, wherein the RNAi molecule does not hybridize to a region of the mRNA that encodes for an ubiquitin associated (UBA) domain or arginine and glycine-rich motif (RGG domain), wherein the RNAi molecule is optionally linked to expression and/or regulatory elements.

Further disclosed herein are isolated host cells comprising, or consisting essentially of, or yet further consisting of, one or more of: (a) an antisense oligonucleotide (ASO) comprising, or consisting essentially of, or yet further consisting of, the oligonucleotide sequence that hybridizes to a region within a mRNA encoding an ubiquitin associated protein 2-like (UBAP2L) protein, (b) an antisense oligonucleotide (ASO) that hybridizes to a region within a mRNA encoding an ubiquitin associated protein 2-like (UBAP2L) protein, wherein the ASO does not hybridize to a region of the mRNA that encodes for an ubiquitin associated (UBA) domain or arginine and glycine-rich motif (RGG domain), (c) a RNA interference (RNAi) molecule comprising, or consisting essentially of, or yet further consisting of, the oligonucleotide sequence of SEQ ID NO: 1 or SEQ ID NO: 2 or an equivalent of each thereof, (d) a RNA interference (RNAi) molecule that hybridizes to a region within a mRNA encoding an ubiquitin associated protein 2-like (UBAP2L) protein, wherein the RNAi molecule does not hybridize to a region of the mRNA that encodes for an ubiquitin associated (UBA) domain or arginine and glycine-rich motif (RGG domain), or (e) a vector comprising, or consisting essentially of, or yet further consisting of, (i) the ASO of (a) or (b); or (ii) the RNAi molecule of (c) or (d), wherein the ASO or RNAi molecule is optionally linked to expression and/or regulatory elements.

Disclosed herein is an antisense oligonucleotide (ASO) that hybridizes to a region within a gene encoding an ubiquitin associated protein 2-like (UBAP2L) protein.

Also disclosed herein is an antisense oligonucleotide (ASO) that hybridizes to a region within a gene encoding an ubiquitin associated protein 2-like (UBAP2L) protein, wherein the ASO does not hybridize to a region of the gene that encodes for an ubiquitin associated (UBA) domain or arginine and glycine-rich motif (RGG domain).

Further disclosed herein is a vector comprising, or consisting essentially of, or yet further consisting of, an antisense oligonucleotide (ASO) that hybridizes to a region within a gene encoding an ubiquitin associated protein 2-like (UBAP2L) protein, wherein the ASO is optionally linked to expression and/or regulatory elements.

Further disclosed herein is a vector comprising, or consisting essentially of, or yet further consisting of, an antisense oligonucleotide (ASO) that hybridizes to a region within a gene encoding an ubiquitin associated protein 2-like (UBAP2L) protein, wherein the ASO does not hybridize to a region of the gene that encodes for an ubiquitin associated (UBA) domain or arginine and glycine-rich motif (RGG domain), wherein the ASO is optionally linked to expression and/or regulatory elements.

Further disclosed herein is a RNA interference (RNAi) molecule that hybridizes to a region within a gene encoding an ubiquitin associated protein 2-like (UBAP2L) protein.

Further disclosed herein is a RNA interference (RNAi) molecule that hybridizes to a region within a gene encoding an ubiquitin associated protein 2-like (UBAP2L) protein, wherein the RNAi molecule does not hybridize to a region of the gene that encodes for an ubiquitin associated (UBA) domain or arginine and glycine-rich motif (RGG domain).

Further disclosed herein is a vector comprising, or consisting essentially of, or yet further consisting of, a RNA interference (RNAi) molecule that hybridizes to a region within a gene encoding an ubiquitin associated protein 2-like (UBAP2L) protein, wherein the RNAi molecule is optionally linked to expression and/or regulatory elements.

Further disclosed herein is a vector comprising, or consisting essentially of, or yet further consisting of, a RNA interference (RNAi) molecule that hybridizes to a region within a gene encoding an ubiquitin associated protein 2-like (UBAP2L) protein, wherein the RNAi molecule does not hybridize to a region of the gene that encodes for an ubiquitin associated (UBA) domain or arginine and glycine-rich motif (RGG domain), wherein the RNAi molecule is optionally linked to expression and/or regulatory elements.

Further disclosed herein are isolated host cells comprising, or consisting essentially of, or yet further consisting of, one or more of: (a) an antisense oligonucleotide (ASO) comprising, or consisting essentially of, or yet further consisting of, the oligonucleotide sequence that hybridizes to a region within a gene encoding an ubiquitin associated protein 2-like (UBAP2L) protein, (b) an antisense oligonucleotide (ASO) that hybridizes to a region within a gene encoding an ubiquitin associated protein 2-like (UBAP2L) protein, wherein the ASO does not hybridize to a region of the gene that encodes for an ubiquitin associated (UBA) domain or arginine and glycine-rich motif (RGG domain), (c) a RNA interference (RNAi) molecule that hybridizes to a region within a gene encoding an ubiquitin associated protein 2-like (UBAP2L) protein, (d) a RNA interference (RNAi) molecule that hybridizes to a region within a gene encoding an ubiquitin associated protein 2-like (UBAP2L) protein, wherein the RNAi molecule does not hybridize to a region of the gene that encodes for an ubiquitin associated (UBA) domain or arginine and glycine-rich motif (RGG domain), or (e) a vector comprising, or consisting essentially of, or yet further consisting of, (i) the ASO of (a) or (b); or (ii) the RNAi molecule of (c) or (d), wherein the ASO or RNAi molecule is optionally linked to expression and/or regulatory elements.

Further disclosed herein is a Clustered Regularly Interspaced Short Palindromic Repeat (CRISPR) system comprising, or consisting essentially of, or yet further consisting of: (a) an oligonucleotide encoding a CRISPR associated endonuclease (Cas) protein; and (b) an oligonucleotide comprising, or consisting essentially of, or yet further consisting of, (i) a first region that hybridizes to an ubiquitin associated protein 2-like (UBAP2L) gene; and (ii) a scaffold sequence.

Further disclosed herein is a vector comprising, or consisting essentially of, or yet further consisting of, a Clustered Regularly Interspaced Short Palindromic Repeat (CRISPR) system comprising, or consisting essentially of, or yet further consisting of: (a) an oligonucleotide encoding a CRISPR associated endonuclease (Cas) protein; and (b) an oligonucleotide comprising, or consisting essentially of, or yet further consisting of, (i) a first region that hybridizes to an ubiquitin associated protein 2-like (UBAP2L) gene; and (ii) a scaffold sequence, wherein one or more of the oligonucleotides of the CRISPR system is optionally linked to expression and/or regulatory elements.

Further disclosed herein is a RNA molecule comprising, or consisting essentially of, or yet further consisting of, a Clustered Regularly Interspaced Short Palindromic Repeat (CRISPR) system comprising, or consisting essentially of, or yet further consisting of: (a) an oligonucleotide encoding a CRISPR associated endonuclease (Cas) protein; and (b) an oligonucleotide comprising, or consisting essentially of, or yet further consisting of, (i) a first region that hybridizes to an ubiquitin associated protein 2-like (UBAP2L) gene; and (ii) a scaffold sequence. In some embodiments, the RNA molecule is encapsulated in a nanoparticle.

Further disclosed herein is an isolated host cell comprising, or consisting essentially of, or yet further consisting of, (A) a Clustered Regularly Interspaced Short Palindromic Repeat (CRISPR) system comprising, or consisting essentially of, or yet further consisting of: (i) an oligonucleotide encoding a CRISPR associated endonuclease (Cas) protein; and (ii) an oligonucleotide comprising, or consisting essentially of, or yet further consisting of, (a) a first region that hybridizes to an ubiquitin associated protein 2-like (UBAP2L) gene; and (b) a scaffold sequence, (B) a RNA molecule comprising, or consisting essentially of, or yet further consisting of, the CRISPR system of (A), or (C) a vector comprising, or consisting essentially of, or yet further consisting of, the CRISPR system of (A).

In some embodiments, the first region of the CRISPR system comprises, or consists essentially of, or yet further consists of, an oligonucleotide sequence of SEQ ID NO: 3 or SEQ ID NO: 4 or an equivalent of each thereof. Alternatively, or additionally, in some embodiments, the first region does not hybridize to a region of the UBAP2L gene that encodes for an ubiquitin associated (UBA) domain or arginine and glycine-rich motif (RGG domain).

Further disclosed herein is a Clustered Regularly Interspaced Short Palindromic Repeat (CRISPR) system comprising, or consisting essentially of, or yet further consisting of: (a) CRISPR associated endonuclease (Cas) protein; and (b) an oligonucleotide comprising, or consisting essentially of, or yet further consisting of, (i) a first region that hybridizes to an ubiquitin associated protein 2-like (UBAP2L) gene; and (ii) a scaffold sequence.

In some embodiments, the first region comprises, or consists of essentially of, or yet further consists of, an oligonucleotide sequence of SEQ ID NO: 3 or SEQ ID NO: 4, or an equivalent of each thereof. Alternatively, or additionally, in some embodiments, the first region does not hybridize to a region of the UBAP2L gene that encodes for an ubiquitin associated (UBA) domain or arginine and glycine-rich motif (RGG domain).

In some embodiments, the oligonucleotide comprises, or consists essentially of, or consists of, RNA.

In some embodiments, the Cas protein is a Cas9 protein.

Further disclosed herein is a kit comprising, or consisting essentially of, or yet further consisting of, (a) an antisense oligonucleotide (ASO) that hybridizes to a region within a mRNA encoding an ubiquitin associated protein 2-like (UBAP2L) protein and (b) instructions for use.

Further disclosed herein is a kit comprising, or consisting essentially of, or yet further consisting of, (a) an antisense oligonucleotide (ASO) that hybridizes to a region within a mRNA encoding an ubiquitin associated protein 2-like (UBAP2L) protein, wherein the ASO does not hybridize to a region of the mRNA that encodes for an ubiquitin associated (UBA) domain or arginine and glycine-rich motif (RGG domain); and (b) instructions for use.

Further disclosed herein is a kit comprising, or consisting essentially of, or yet further consisting of, (a) a vector comprising, or consisting essentially of, or yet further consisting of, an antisense oligonucleotide (ASO) that hybridizes to a region within a mRNA encoding an ubiquitin associated protein 2-like (UBAP2L) protein, wherein the ASO is optionally linked to expression and/or regulatory elements; and (b) instructions for use.

Further disclosed herein is a kit comprising, or consisting essentially of, or yet further consisting of, (a) a vector comprising, or consisting essentially of, or yet further consisting of, an antisense oligonucleotide (ASO) that hybridizes to a region within a mRNA encoding an ubiquitin associated protein 2-like (UBAP2L) protein, wherein the ASO does not hybridize to a region of the mRNA that encodes for an ubiquitin associated (UBA) domain or arginine and glycine-rich motif (RGG domain), wherein the ASO is optionally linked to expression and/or regulatory elements; and (b) instructions for use.

Further disclosed herein is a kit comprising, or consisting essentially of, or yet further consisting of, (a) a vector comprising, or consisting essentially of, or yet further consisting of, a RNAi molecule comprising, or consisting essentially of, or yet further consisting of, the oligonucleotide sequence of SEQ ID NO: 1 or SEQ ID NO: 2 or equivalent of each thereof, wherein the RNAi molecule is optionally linked to expression and/or regulatory elements; and (b) instructions for use.

Further disclosed herein is a kit comprising, or consisting essentially of, or yet further consisting of, (a) a vector comprising, or consisting essentially of, or yet further consisting of, a RNAi molecule that hybridizes to a region within a mRNA encoding an ubiquitin associated protein 2-like (UBAP2L) protein, wherein the RNAi molecule does not hybridize to a region of the mRNA that encodes for an ubiquitin associated (UBA) domain or arginine and glycine-rich motif (RGG domain), and wherein the RNAi molecule is optionally linked to expression and/or regulatory elements; and (b) instructions for use.

Further disclosed herein is a kit comprising, or consisting essentially of, or yet further consisting of, (a) an antisense oligonucleotide (ASO) that hybridizes to a region within a gene encoding an ubiquitin associated protein 2-like (UBAP2L) protein and (b) instructions for use.

Further disclosed herein is a kit comprising, or consisting essentially of, or yet further consisting of, (a) an antisense oligonucleotide (ASO) that hybridizes to a region within a gene encoding an ubiquitin associated protein 2-like (UBAP2L) protein, wherein the ASO does not hybridize to a region of the gene that encodes for an ubiquitin associated (UBA) domain or arginine and glycine-rich motif (RGG domain); and (b) instructions for use.

Further disclosed herein is a kit comprising, or consisting essentially of, or yet further consisting of, (a) a vector comprising, or consisting essentially of, or yet further consisting of, an antisense oligonucleotide (ASO) that hybridizes to a region within a gene encoding an ubiquitin associated protein 2-like (UBAP2L) protein, wherein the ASO is optionally linked to expression and/or regulatory elements; and (b) instructions for use.

Further disclosed herein is a kit comprising, or consisting essentially of, or yet further consisting of, (a) a vector comprising, or consisting essentially of, or yet further consisting of, an antisense oligonucleotide (ASO) that hybridizes to a region within a gene encoding an ubiquitin associated protein 2-like (UBAP2L) protein, wherein the ASO does not hybridize to a region of the gene that encodes for an ubiquitin associated (UBA) domain or arginine and glycine-rich motif (RGG domain), wherein the ASO is optionally linked to expression and/or regulatory elements; and (b) instructions for use.

Further disclosed herein is a kit comprising, or consisting essentially of, or yet further consisting of, (a) a vector comprising, or consisting essentially of, or yet further consisting of, a RNAi molecule that hybridizes to a region within a gene encoding an ubiquitin associated protein 2-like (UBAP2L) protein, wherein the RNAi molecule is optionally linked to expression and/or regulatory elements; and (b) instructions for use.

Further disclosed herein is a kit comprising, or consisting essentially of, or yet further consisting of, (a) a vector comprising, or consisting essentially of, or yet further consisting of, a RNAi molecule that hybridizes to a region within a gene encoding an ubiquitin associated protein 2-like (UBAP2L) protein, wherein the RNAi molecule does not hybridize to a region of the gene that encodes for an ubiquitin associated (UBA) domain or arginine and glycine-rich motif (RGG domain), and wherein the RNAi molecule is optionally linked to expression and/or regulatory elements; and (b) instructions for use.

Further disclosed herein is a kit comprising, or consisting essentially of, or yet further consisting of, (A) a vector comprising, or consisting essentially of, or yet further consisting of, a CRISPR system comprising, or consisting essentially of, or yet further consisting of: (i) an oligonucleotide encoding a CRISPR associated endonuclease (Cas) protein; and (ii) an oligonucleotide comprising, or consisting essentially of, or yet further consisting of, (a) a first region that hybridizes to an ubiquitin associated protein 2-like (UBAP2L) gene; and (b) a scaffold sequence, and wherein the CRISPR system is optionally linked to expression and/or regulatory elements; and (B) instructions for use. In some embodiments, the first region comprises, or consists essentially of, or consists of, an oligonucleotide sequence of SEQ ID NO: 3 or SEQ ID NO: 4 or an equivalent of each thereof. Alternatively, or additionally, in some embodiments, the first region does not hybridize to a region of the UBAP2L gene that encodes for an ubiquitin associated (UBA) domain or arginine and glycine-rich motif (RGG domain).

Further disclosed herein is a kit comprising, or consisting essentially of, or yet further consisting of, (a) a RNA interference (RNAi) molecule comprising, or consisting essentially of, or yet further consisting of, the oligonucleotide sequence of SEQ ID NO: 1 or SEQ ID NO: 2, or an equivalent of each thereof; and (b) instructions for use.

Further disclosed herein is a kit comprising, or consisting essentially of, or yet further consisting of, (a) a RNA interference (RNAi) molecule that hybridizes to a region within a mRNA encoding an ubiquitin associated protein 2-like (UBAP2L) protein, wherein the RNAi molecule does not hybridize to a region of the mRNA that encodes for an ubiquitin associated (UBA) domain or arginine and glycine-rich motif (RGG domain); and (b) instructions for use.

Further disclosed herein is a kit comprising, or consisting essentially of, or yet further consisting of, (a) an isolated host cell comprising, or consisting essentially of, or yet further consisting of, one or more of: (i) antisense oligonucleotide (ASO) that hybridizes to a region within a mRNA encoding an ubiquitin associated protein 2-like (UBAP2L) protein; (ii) an antisense oligonucleotide (ASO) that hybridizes to a region within a mRNA encoding an ubiquitin associated protein 2-like (UBAP2L) protein, wherein the ASO does not hybridize to a region of the mRNA that encodes for an ubiquitin associated (UBA) domain or arginine and glycine-rich motif (RGG domain); (iii) a RNA interference (RNAi) molecule comprising, or consisting essentially of, or yet further consisting of, the oligonucleotide sequence of SEQ ID NO: 1 or SEQ ID NO: 2 or an equivalent of each thereof; (iv) a RNA interference (RNAi) molecule that hybridizes to a region within a mRNA encoding an ubiquitin associated protein 2-like (UBAP2L) protein, wherein the RNAi molecule does not hybridize to a region of the mRNA that encodes for an ubiquitin associated (UBA) domain or arginine and glycine-rich motif (RGG domain); or (v) a vector comprising, or consisting essentially of, or yet further consisting of, any of (i)-(iv); and (b) instructions for use.

Further disclosed herein is a kit comprising, or consisting essentially of, or yet further consisting of, (I) an isolated host cell comprising, or consisting essentially of, or yet further consisting of, one or more of: (A) one or more of: (i) a Clustered Regularly Interspaced Short Palindromic Repeat (CRISPR) system comprising, or consisting essentially of, or yet further consisting of: (a) an oligonucleotide encoding a CRISPR associated endonuclease (Cas) protein; and (b) an oligonucleotide comprising, or consisting essentially of, or yet further consisting of, (1) a first region that hybridizes to an ubiquitin associated protein 2-like (UBAP2L) gene; and (2) a scaffold sequence; (ii) a RNA molecule comprising, or consisting essentially of, or yet further consisting of, the CRISPR system of (i); or (iii) a vector comprising, or consisting essentially of, or yet further consisting of, (i) or (ii); and (II) instructions for use. In some embodiments, the first region comprises, or consists essentially of, or consists of, an oligonucleotide sequence of SEQ ID NO: 3 or SEQ ID NO: 4, or an equivalent of each thereof. Alternatively, or additionally, in some embodiments, the first region does not hybridize to a region of the UBAP2L gene that encodes for an ubiquitin associated (UBA) domain or arginine and glycine-rich motif (RGG domain).

Further disclosed herein is a kit comprising, or consisting essentially of, or yet further consisting of, (A) a Clustered Regularly Interspaced Short Palindromic Repeat (CRISPR) system comprising, or consisting essentially of, or yet further consisting of: (i) CRISPR associated endonuclease (Cas) protein; and (ii) an oligonucleotide comprising, or consisting essentially of, or yet further consisting of, (a) a first region that hybridizes to an ubiquitin associated protein 2-like (UBAP2L) gene; and (b) a scaffold sequence; and (B) instructions for use. In some embodiments, the first region comprises, or consists essentially of, or consists of, an oligonucleotide sequence of SEQ ID NO: 3 or SEQ ID NO: 4 or an equivalent of each thereof. Alternatively, or additionally, in some embodiments, the first region does not hybridize to a region of the UBAP2L gene that encodes for an ubiquitin associated (UBA) domain or arginine and glycine-rich motif (RGG domain). In some embodiments, the oligonucleotide comprises, or consists essentially of, or consists of, RNA.

Further disclosed herein is a kit comprising, or consisting essentially of, or yet further consisting of, (A) an RNA molecule comprising, or consisting essentially of, or yet further consisting of, (i) a Clustered Regularly Interspaced Short Palindromic Repeat (CRISPR) system comprising, or consisting essentially of, or yet further consisting of: (a) an oligonucleotide encoding a CRISPR associated endonuclease (Cas) protein; and (b) an oligonucleotide comprising, or consisting essentially of, or yet further consisting of, (1) a first region that hybridizes to an ubiquitin associated protein 2-like (UBAP2L) gene; and (2) a scaffold sequence; and (B) instructions for use. In some embodiments, the first region comprises, or consists essentially of, or consists of, an oligonucleotide sequence of SEQ ID NO: 3 or SEQ ID NO: 4 or an equivalent of each thereof. Alternatively, or additionally, in some embodiments, the first region does not hybridize to a region of the UBAP2L gene that encodes for an ubiquitin associated (UBA) domain or arginine and glycine-rich motif (RGG domain). In some embodiments, the RNA molecule is encapsulated in a nanoparticle.

BRIEF DESCRIPTION OF THE DRAWINGS

(FIG. 1A) Schematic of APEX proximity labeling to tag SG proteins with biotin. (FIG. 1B) Streptavidin staining of unstressed and NaAsO2-treated HEK293T G3BP1-APEX2-GFP and hPGK-NES-APEX2-GFP cells. Scale bars, 25 mm. (FIG. 1C) Streptavidin-HRP western blot analysis of induced protein biotinylation in lysates from NES-APEX2-GFP and G3BP1-APEX2-GFP cells. (FIG. 1D) Schematic of G3BP1 interactome changes upon stress. (FIG. 1E) Experimental designs for detecting the G3BP1 interactome changes under different conditions, including log 2 H/L ratio distributions of all proteins detected, overlaid with log 2 H/L ratio distributions of known SG proteins.

(FIG. 2A) Enrichment frequency distribution of known SG proteins in log 2 H/L-ranked proteomics datasets. The dashed line represents 2 times the background frequency of SG proteins across all detected proteins. (FIG. 2B) Venn diagram showing overlapping hits from four experimental designs, with previously known SG proteins highlighted in bold. (FIG. 2C) Volcano plots showing statistically significant enrichment of selected known and previously unknown SG proteins across experiments. (FIG. 2D) Protein interaction network (PIN) of 283 proteins identified as APEX hits in HEK293T cells or previously shown to associate with SGs. Network was visualized in Cytoscape using a force-directed layout. (FIG. 2E) Common network parameters for the SG-PIN compared to five PINs from a randomly selected equal number of nodes and edges.

(FIG. 3A) Overview of NPC generation from induced pluripotent stem cells (iPSCs). (FIG. 3B) Enrichment frequency distribution of known SG proteins in log 2 H/L-ranked proteomics datasets. The dashed lines represent 2 times the background frequency of SG proteins across all detected proteins. (FIG. 3C) Volcano plot showing statistically significant enrichment of selected known and previously unknown neuronal SG proteins in NPCs. (FIG. 3D) Venn diagram showing the overlap between known SG proteins and SG-APEX hits identified in HEK293T cells and NPCs. (FIG. 3E) Previously unknown SG proteins identified by SG-APEX in both HEK293T cells and NPCs. (FIG. 3F) IF images of selected neuronal SG proteins with functions related to protein folding. (FIG. 3G) IF images of selected neuronal SG proteins with functions in autophagy and vesicular transport. (FIG. 3H) Ranked list of proteins with the greatest connectivity to SG proteins as determined by the Enrichr gene enrichment analysis tool. Scale bars in (FIG. 3A), (FIG. 3F), and (FIG. 3G), 25 µm. See also FIG. 10.

(FIG. 4A) High-content imaging (HCI) screen outline to identify SG-localized RBPs in HepG2 cells, HeLa cells, and NPCs. (FIG. 4B) IF images showing examples of RBP localization in untreated, NaAsO2 (AS)-treated, and heat-shock (HS)-treated HeLa cells. UBAP2L is a common hit in both stress conditions; NOLC1 and SF1 are specific to NaAsO2 and heat shock, respectively. Left panels are merged lower-resolution views, and right panels represent zoomed-in views of the indicated selection separately showing TIA-1 (red) or the test RBP (green). Arrowheads indicate co-localization of the test RBP with TIA1. (FIG. 4C) Venn diagram comparing SG proteins in HeLa cells treated with NaAsO2 versus heat shock. (FIG. 4D) Quantification of the mean granule penetrance of proteins with either constitutive (UBAP2L) or stress-type-specific (NOLC1 and SF1) SG localization. (FIG. 4E) IF images showing examples of RBP localization in untreated and NaAsO2-treated HeLa cells, HepG2 cells, or NPCs. UBAP2L is found in SGs in all three cell types, while SRSF9, EIF3A, and SRP68 are specific to HepG2 cells, HeLa cells, and NPCs, respectively. Top panels are merged lower-resolution views, while the bottom panels represent zoomed-in views of the indicated selection separately showing TIA-1 (red) or the test RBP (green). Arrowheads indicate examples of RBPs co-localized with TIA-1. (FIG. 4F) Venn diagram comparing SG proteins in HepG2, HeLa and NPCs treated with NaAsO2. (FIG. 4G) Mean granule penetrance of proteins with either cell-type-independent or cell-type-specific SG localization. Scale bars in (FIG. 4B) and (FIG. 4E), 20 Error bars in (FIG. 4D) and (FIG. 4G) represent SD. See also Table 4.

(FIG. 5A) IF images of SND1 and IGF2BP3 localization in unstressed or NaAsO2-treated iPS-MNs. Top panels are merged lower-resolution views, while the bottom panels represent zoomed-in views of the indicated selection separately showing G3BP1 (green) or the test RBP (red). Arrowheads indicate examples of RBPs co-localized with G3BP1. (FIG. 5B) Overview of RBPs whose localization in unstressed iPS-MNs is either restricted to the cell body or extends into neuronal projections. (FIG. 5C) Time-course analysis of SG formation in iPS-MNs from controls or from ALS patients bearing mutations in HNRNPA2B1 or C9orf72, respectively. (FIG. 5D) IF images of control and HNRNPA2B1 mutant iPS-MNs that were either untreated or stressed with puromycin. Top panels are merged lower-resolution views, while the bottom panels represent zoomed-in views of the indicated selection separately showing G3BP1 (green) or the test RBP (red). White and yellow arrowheads indicate examples of SGs formed in cell bodies or neurites, respectively. (FIG. 5E) Quantification of SG area and number in untreated or stressed control and HNRNPA2B1 mutant iPS-MNs. (FIG. 5F) Quantification of RBPs that localize to SGs in cell bodies or dendritic projections in control versus HNRNPA2B1 mutant cells. The RBPs exhibiting targeting to SGs in projections in HNRNPA2B1 mutant cells are highlighted in the panel on the right. Scale bars, 20 µm. Error bars in (FIG. 5C) and (FIG. 5E) represent SD. Statistical significance was calculated by 2-way ANOVA (FIG. 5C) or Student's t test (E). *p % 0.05; p % 0.01; *p % 0.001; ****p % 0.0001. See also FIG. 11 and Table 5.

(FIG. 6A) Venn diagram showing overlap between proteins identified in our combined APEX-IF approach, known SG proteins, and RBPs. (FIG. 6B) Protein domain enrichment analysis of 260 SG APEX-IF. (FIG. 6C) Gene ontology analysis for 260 APEX-IF hits. (FIG. 6D) Comparison of the proportion of amino acids in LCDs and IDRs between APEX-IF hits and background. (FIG. 6E) Heatmap for the 75 proteins most broadly represented across selected SG and neurodegeneration-relevant datasets. Heatmap indicates whether a protein is present (blue box) or absent (white box) from each dataset, and proteins are ranked by the number of datasets they are part of in descending order from left to right. (FIG. 6F) Images of Drosophila eye degeneration models crossed with the indicated strains. (FIG. 6G) Images and quantitation of the wing notching phenotype caused by poly(GR) toxicity in flies. w1118 flies were used as the control for genetic mutant alleles, while UAS-GFP served as the control for different UAS-RNAi lines. Numbers indicate Bloomington stock numbers for each mutant or RNAi line. (FIG. 6H) IF images of G3BP1 staining and quantification of SG numbers in HeLa cells treated with control siRNA or siRNA targeting UBAP2L. Data are presented as mean ±SEM, and statistical significance was determined by two-tailed unpaired t test. (FIG. 6I) IF images of 293FITR cells with inducible expression of either a full-length UBAP2L-mCherry fusion protein (top panel) or a truncated UBAP2L-mCherry fusion protein missing the N-terminal UBA domain (middle and bottom panels). Scale bars in (FIG. 6H) are 25 µm. See also FIG. 12.

(FIG. 7A) Model of the relationships among normally functioning, dynamic RBPs, transient SGs, and permanent pathological protein inclusions. (FIG. 7B) Schematic showing that neuronal SGs are diverse and contain proteins involved in protein quality control pathways. (FIG. 7C) Schematic showing altered SG dynamics, composition, and subcellular distribution in ALS mutant motor neurons.

(FIG. 8A) Schematic of CRISPR-Cas9-mediated endogenous tagging of the G3BP1 locus. (FIG. 8B) Schematic of generating a constitutive hPGK::NES-APEX2-GFP-expressing HEK293T cell line. (FIG. 8C) Schematic description of the SILAC experimental workflow. (FIG. 8D) Venn diagram showing overview of all proteins detected by MS in streptavidin affinity-purified samples, corresponding input samples in relation to a list of known SG proteins. (FIG. 8E) Flow chart depicting data analysis steps to identify candidate SG proteins.

(FIG. 9A) Venn diagrams showing overlap between proteins identified from HEK293T cells in biological replicate experiments. (FIG. 9B) Scatterplots showing correlation between log 2 H/L ratios for identified proteins from biological replicate experiments.

(FIG. 10A) Streptavidin staining of unstressed (top panel) and sodium arsenite-treated (middle and bottom panels) CV-B G3BP1-APEX2-GFP neural progenitor cells. Cells were either incubated in the presence (upper and middle panels) or absence (lower panel) of biotin phenol. (FIG. 10B) SG-APEX experimental designs used in NPCs. (FIG. 10C) Venn diagram showing overview of all proteins detected by MS in NPC input and IP samples and overlap with known SG proteins. (FIG. 10D) Venn diagram showing overlap of all proteins detected above fold-change cutoff in NPC stressed with either sodium arsenite or thapsigargin.

(FIG. 11A) IF staining of wild-type and HNRNPA2B1 mutant motor neurons showing expression of the motor neuron-specific phosphorylated neurofilament SMI-31 and the transcription factor ISL1/2. (FIG. 11B) IF staining of wild-type and HNRNPA2B1 mutant motor neurons that were either left untreated or stressed with puromycin, then co-labeled with G3BP1 (green) and a panel of RBP antibodies (red). Upper panels are merged views with lower resolution. In each panel, the indicated insets at the bottom are zoomed views of the same field showing G3BP1 (green) and the RBP (red). (FIG. 11C) Enrichment analysis for KEGG pathways and Biological Process Gene Ontology term as determined by the Enrichr gene enrichment analysis tool.

(FIG. 12A) Venn diagram showing overlap between SG proteins identified in our study, compared to the SG core proteome (Jain et al., 2016) and known SG proteins. (FIG. 12B) Heatmap for all 1312 proteins represented across selected SG and neurodegeneration-relevant datasets, indicating whether a protein is present (blue box) or absent (white box) from each dataset. Proteins are ranked by the number of datasets they are part of in descending order from top to bottom. (FIG. 12C) Quantitation of the wing notching phenotype caused by poly(GR) toxicity in flies. w1118 flies were used as the control for genetic mutant alleles, while UAS-GFP served as the control for different UAS-RNAi lines. The Bloomington stock numbers for each mutant or RNAi line are listed. (FIG. 12D) IF images of 293FITR cells with inducible expression of either a full-length UBAP2L-mCherry fusion protein (top) or a truncated UBAP2L-mCherry fusion protein missing the N-terminal UBA domain (bottom). (FIG. 12E) Graphs showing protein domains, distribution of low complexity domains and intrinsically disordered regions across the length of human UBAP2L protein.

Figures 1A, 1B, 1C, 1D, 1E:
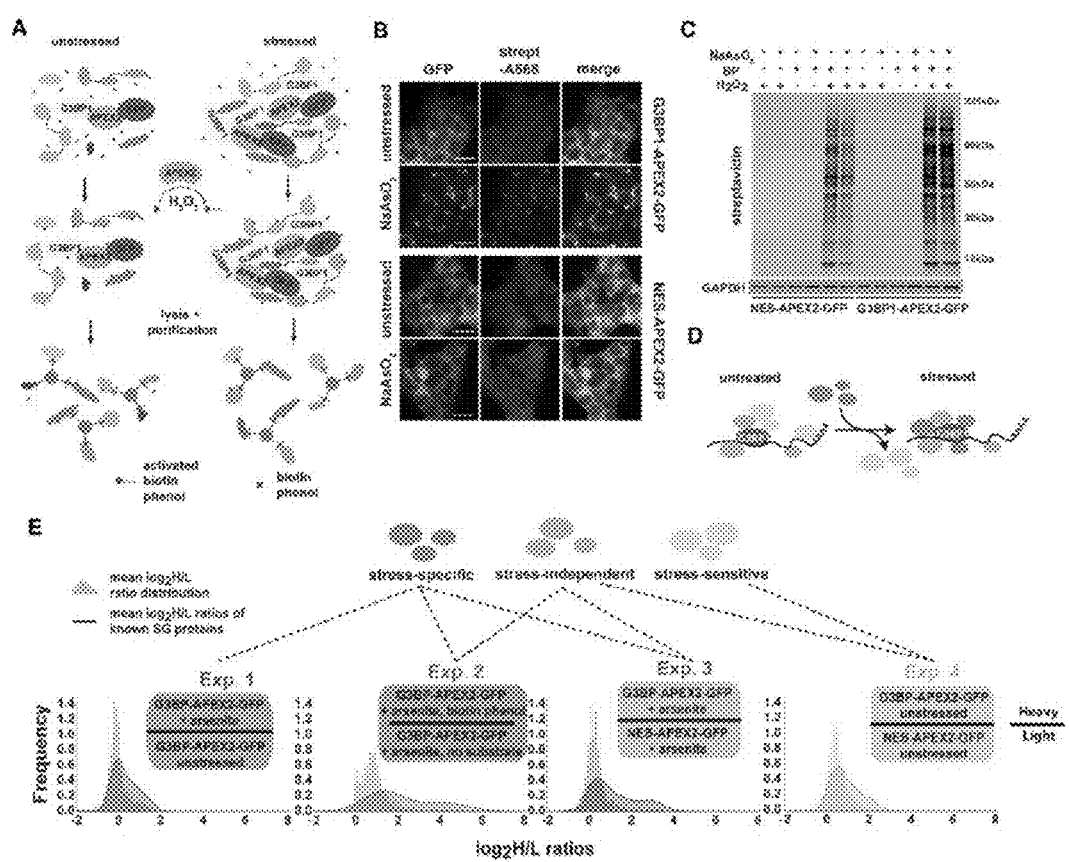
FIGS. 1A-1E: G3BP1-APEX2 Mediates Specific Biotinylation of Stress-Granule-Associated Proteins.

Table 1: Contains a literature-sourced, manually curated list of proteins previously found to associate with SGs.

Table 2: Contains a list of candidate SG proteins identified by mass spectrometry.

Table 3: Contains a list of RBPs found to co-localize with SGs by high-throughput immunofluorescence screening in different stress conditions.

Table 4: Contains a list of RBPs found to co-localize with SGs by high-throughput immunofluorescence screening in different cell types.

Table 5: Contains a list of RBPs localizing to SGs with different subcellular localizations in control and ALS mutant iPS-MNs.

Table 6: Contains a list of RBPs found to localize by immunofluorescence to the cell body or neuronal projections in unstressed iPS-MNs.

Table 7: Contains a list of oligonucleotides used for cloning and sequence verification of homology recombination donors, gRNA expression constructs and UBAP2L expression constructs. Table 7 also contains sequences of siRNAs used for UBAP2L knockdown.

Table 8: Contains a list of reagents, resources, and experimental models used in the examples.

Table 9: Contains a list of reagents, resources, oligonucleotides, recombinant DNA, software, and algorithms used in the examples.

DETAILED DESCRIPTION

Described herein is an ubiquitin associated protein 2-like (UBAP2L) protein that is involved in stress granule (SG) formation and the development and progression of neurodegenerative disorders. The inhibition of UBAP2L expression and/or activity prevents SG formation. Thus, provided herein are UBAP2L targeting agents and the use of such agents for inhibiting the formation stress granules, and treating a neurodegenerative disorder. In addition, methods of monitoring the progression of a neurodegenerative disorder and determining the efficacy of a neurodegenerative disorder therapy are disclosed herein.

Definitions

Throughout this disclosure, various publications, patents and published patent specifications are referenced by an identifying citation. The disclosures of these publications, patents and published patent specifications are hereby incorporated by reference into the present disclosure to more fully describe the state of the art to which this disclosure pertains.

Technical and scientific terms used herein have the meanings commonly understood by one of ordinary skill in the art to which the present disclosure pertains, unless otherwise defined.

As used herein, the singular forms "a," "an," and "the" designate both the singular and the plural, unless expressly stated to designate the singular only.

As used herein, "and/or" refers to and encompasses any and all possible combinations of one or more of the associated listed items, as well as the lack of combinations when interpreted in the alternative ("or").

As used herein, "subject" denotes any mammal, including humans.

The terms "administer," "administration," or "administering" as used herein refer to (1) providing, giving, dosing and/or prescribing, such as by either a health professional or his or her authorized agent or under his direction, and (2) putting into, taking or consuming, such as by a health professional or the subject.

The terms "treat", "treating" or "treatment", as used herein, include alleviating, abating or ameliorating a disease or condition or one or more symptoms thereof, whether or not the disease or condition is considered to be "cured" or "healed" and whether or not all symptoms are resolved. The terms also include reducing or preventing progression of a disease or condition or one or more symptoms thereof, impeding or preventing an underlying mechanism of a disease or condition or one or more symptoms thereof, and achieving any therapeutic and/or prophylactic benefit.

As used herein, the term "CRISPR" refers to a technique of sequence specific genetic manipulation relying on the clustered regularly interspaced short palindromic repeats pathway. CRISPR can be used to perform nucleic acid editing and/or regulation, as well as to simply target proteins to a specific genomic or mRNA location. Nucleic acid editing refers to a type of genetic engineering in which the nucleotide sequence of a target polynucleotide is changed through introduction of deletions, insertions, cleavages, or base substitutions to the polynucleotide sequence. In some aspects, CRISPR-mediated editing utilizes the pathways of nonhomologous end-joining (NHEJ) or homologous recombination to perform the edits. Nucleic acid regulation refers to increasing or decreasing the production of specific gene products such as protein or RNA.

The term "gRNA" or "guide RNA" as used herein refers to the guide RNA sequences used to target specific genes for correction employing the CRISPR technique. Techniques of designing gRNAs and donor therapeutic polynucleotides for target specificity are well known in the art. For example, Doench, J., et al. Nature biotechnology 2014; 32(12):1262-7, Mohr, S. et al. (2016) FEBS Journal 283: 3232-38, and Graham, D., et al. Genome Biol. 2015; 16: 260. In some embodiments, a gRNA comprises or alternatively consists essentially of, or yet further consists of a fusion polynucleotide comprising, or consisting essentially of, or yet further consisting of, CRISPR RNA (crRNA) and trans-activating CRIPSPR RNA (tracrRNA); or a polynucleotide comprising, or consisting essentially of, or yet further consisting of, CRISPR RNA (crRNA) and trans-activating CRIPSPR RNA (tracrRNA). In some embodiments, a gRNA is synthetic (Kelley, M. et al. (2016) J of Biotechnology 233 (2016) 74-83). In some embodiments, a gRNA comprises, or consists essentially of, or consists of, at least a first region that hybridizes to target polynucleotide; and a second region comprising, or consisting essentially of, or yet further consisting of, a gRNA scaffold (e.g., scaffold sequence).

The term "Cas9" refers to a CRISPR associated endonucleoase referred to by this name (UniProtKB G3ECR1 (CAS9_STRTR)) as well as orthologs and biological equivalents thereof. In some embodiments, Cas9 lacks endonuclease activity. For example, in some embodiments, Cas9 is deadCas-9 or dCas9, which lacks endonuclease activity but retains the ability to target a target polynucleotide in the presence of a gRNA. Orthologs of Cas9 include but are not limited to *Streptococcus pyogenes* Cas9 ("spCas9"); Cas9 from *Streptococcus thermophiles, Legionella pneumophilia, Neisseria lactamica, Neisseria meningitides, Francisella novicida*; and Cpf1 (which performs cutting functions analogous to Cas9) from various bacterial species including *Acidaminococcus* spp. and *Francisella novicida* U112. In some embodiments, the Cas9 is "split-Cas9" in which Cas9 is split into two halves—C-Cas9 and N-Cas9—and fused with a two intein moieties. See e.g. Volz et al. (2015) Nat Biotechnol. 33(2):139-42; Wright et al. (2015) PNAS 112 (10) 2984-89. A non-limiting exemplary split-Cas9 has a C-Cas9 comprising residues 574-1398 and N-Cas9 comprising residues 1-573. An exemplary split-Cas9 for dCas9 involves two domains comprising these same residues of dCas9, denoted dC-Cas9 and dN-Cas9.

The terms "gRNA scaffold" and "scaffold sequence" are used interchangeably and refer to a region with the guide RNA that is involved in the binding of a CRISPR associated endonuclease (e.g., Cas protein).

The term "RNA interference" (RNAi) refers to sequence-specific or gene specific suppression of gene expression (protein synthesis) that is mediated by short interfering RNA (siRNA) or microRNA (miRNA).

The term "short interfering RNA" (siRNA) refers to double-stranded RNA molecules (dsRNA), generally, from about 10 to about 30 nucleotides in length that are capable of mediating RNA interference (RNAi), or 11 nucleotides in length, 12 nucleotides in length, 13 nucleotides in length, 14 nucleotides in length, 15 nucleotides in length, 16 nucleotides in length, 17 nucleotides in length, 18 nucleotides in length, 19 nucleotides in length, 20 nucleotides in length, 21 nucleotides in length, 22 nucleotides in length, 23 nucleotides in length, 24 nucleotides in length, 25 nucleotides in length, 26 nucleotides in length, 27 nucleotides in length, 28 nucleotides in length, or 29 nucleotides in length. As used herein, the term siRNA includes short hairpin RNAs (shRNAs).

shRNAs comprise a single strand of RNA that forms a stem-loop structure, where the stem consists of the complementary sense and antisense strands that comprise a double-stranded siRNA, and the loop is a linker of varying size. The stem structure of shRNAs generally is from about 10 to about 30 nucleotides in length. For example, the stem can be 10-30 nucleotides in length, or alternatively, 12-28 nucleotides in length, or alternatively, 15-25 nucleotides in length, or alternatively, 19-23 nucleotides in length, or alternatively, 21-23 nucleotides in length.

The term "double stranded RNA" (dsRNA) refers to double stranded RNA molecules that may be of any length and may be cleaved intracellularly into smaller RNA molecules, such as siRNA. In cells that have a competent interferon response, longer dsRNA, such as those longer than about 30 base pair in length, may trigger the interferon response. In other cells that do not have a competent interferon response, dsRNA may be used to trigger specific RNAi.

Tools to assist siRNA design are readily available to the public. For example, a computer-based siRNA design tool is available on the internet at www.dharmacon.com, Ambion-www.ambion.com/jp/techlib/misc/siRNA_finder.html;ThermoScientific-Dharmacon-www.dharmacon.com/Design-Center/DesignCenterPage.aspx; Bioinformatics Research Center-sysbio.kribb.re.kr:8080/AsiDesigner/menuDesigner-.jsf;andInvitrogenrnaidesigner.invitrogen.com/rnaiexpress/.

The term "antisense oligonucleotide" (ASO) refers to a synthetic single strand of nucleic acids that bind to RNA, thereby altering or reducing the expression of the RNA. The ASO generally is from about 5 to about 70 nucleotides in length. For example, the ASO can be 5-50 nucleotides in length, or alternatively, 8-50 nucleotides in length, or alternatively, 15-40 nucleotides in length, or alternatively, 10-30 nucleotides in length, or alternatively, 8-40 nucleotides in length The term "cell" as used herein may refer to either a prokaryotic or eukaryotic cell, optionally obtained from a subject or a commercially available source.

As used herein, the term "comprising" is intended to mean that the compositions and methods include the recited elements, but do not exclude others. As used herein, the transitional phrase "consisting essentially of" (and grammatical variants) is to be interpreted as encompassing the recited materials or steps "and those that do not materially affect the basic and novel characteristic(s)" of the recited embodiment. See, *In re Herz,* 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising." "Consisting of" shall mean excluding more than trace elements of other ingredients and substantial method steps for administering the compositions disclosed herein. Aspects defined by each of these transition terms are within the scope of the present disclosure.

The term "encode" as it is applied to nucleic acid sequences refers to a oligonucleotide which is said to "encode" a polypeptide if, in its native state or when manipulated by methods well known to those skilled in the art, can be transcribed and/or translated to produce the mRNA for the polypeptide and/or a fragment thereof. The antisense strand is the complement of such a nucleic acid, and the encoding sequence can be deduced therefrom.

As used herein, the terms "nucleic acid sequence" and "oligonucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "protein", "peptide" and "polypeptide" are used interchangeably and in their broadest sense to refer to a compound of two or more subunits of amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The term "promoter" as used herein refers to any sequence that regulates the expression of a coding sequence, such as a gene. Promoters may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors. Non-limiting exemplary promoters include CMV promoter and U6 promoter.

The term "isolated" as used herein refers to molecules or biologicals or cellular materials being substantially free from other materials.

The term "tissue" is used herein to refer to tissue of a living or deceased organism or any tissue derived from or designed to mimic a living or deceased organism. The tissue may be healthy, diseased, and/or have genetic mutations. The biological tissue may include any single tissue (e.g., a collection of cells that may be interconnected) or a group of tissues making up an organ or part or region of the body of an organism. The tissue may comprise a homogeneous cellular material or it may be a composite structure such as that found in regions of the body including the thorax which for instance can include lung tissue, skeletal tissue, and/or muscle tissue. Exemplary tissues include, but are not limited to those derived from liver, lung, thyroid, skin, pancreas, blood vessels, bladder, kidneys, brain, biliary tree, duodenum, abdominal aorta, iliac vein, heart and intestines, including any combination thereof.

The term "specifically binds" refers to the binding specificity of a specific binding pair. For instance, hybridization by an ubiquitin associated protein 2-like (UBAP2L) targeting agent to a UBAP2L protein, mRNA, or gene in the presence of other proteins, mRNA sequences, or gene sequences is one characteristic of such binding. Specific binding may involve two different nucleic acid molecules wherein one of the nucleic acid molecules specifically hybridizes with the second nucleic acid molecule through chemical or physical means. The two nucleic acid molecules are related in the sense that their binding with each other is such that they are capable of distinguishing their binding partner from other assay constituents having similar characteristics. For instance, the UBAP2L targeting agent may comprise a CRISPR system, in which the gRNA of the CRISPR system specifically binds to the UBAP2L mRNA sequence.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, polypeptide or nucleic acid, intends those having minimal homology while still maintaining desired structure and/or functionality. Unless specifically recited herein, it is contemplated that any polynucleotide, polypeptide or protein mentioned herein also includes equivalents thereof. For example, an equivalent intends at least about 70% homology or identity, or at least 80% homology or identity and alternatively, or at least about 85%, or alternatively at least about 90%, or alternatively at least about 95%, or alternatively 98% percent homology or identity and exhibits substantially equivalent biological activity to the reference protein, polypeptide or nucleic acid. Alternatively, when referring to polynucleotides, an equivalent thereof can in one aspect, is a polynucleotide that hybridizes under stringent conditions to the reference polynucleotide or its complement.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PC reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

Inhibition of Stress Granule Formation

Stress granules (SGs) are transient ribonucleoprotein (RBP) aggregates that form during cellular stress and are increasingly implicated in human neurodegeneration. Example 1 has identified UBAP2L as an essential regulator of SG assembly. In addition, the results demonstrate that inhibition/depletion of UBAP2L reduces SG formation. Thus, disclosed herein are methods for inhibiting the formation of a toxic insoluble protein aggregate stress granule (SG) comprising, or consisting essentially of, or yet further consisting of, UBAP2L in a mammalian neuronal cell. Generally, the method comprises, or consists essentially of, or yet further consists of, contacting the cell with an effective amount of an ubiquitin associated protein 2-like (UBAP2L) targeting agent that specifically targets one or more regions within an UBAP2L protein, mRNA, or gene.

In some embodiments, the UBAP2L protein comprises, or consists essentially of, or yet further consists of, or has the amino acid sequence of SEQ ID NO: 6 or an equivalent thereof. In some embodiments, the UBAP2L mRNA comprises, or consists essentially of, or yet further consists of, or has the nucleotide sequence of SEQ ID NO: 5 or an equivalent thereof. In some embodiments, the UBAP2L gene comprises, or consists essentially of, or yet further consists of, or has the nucleotide sequence of NCBI Reference No. NC_000001.11 or an equivalent thereof.

In some embodiments, the UBAP2L targeting agent specifically targets one or more regions within bases 617 to 3889 of an UBAP2L messenger RNA (mRNA) molecule having a nucleotide sequence of SEQ ID NO: 5 or an equivalent thereof.

In some embodiments, the UBAP2L targeting agent does not bind to a region of the UBAP2L that corresponds to the ubiquitin associated (UBA) domain. In some embodiments, the UBA domain comprises, or consists essentially of, or yet further consists of, or has a nucleotide sequence of SEQ ID NO: 7 or an equivalent thereof. In some embodiments, the UBA domain comprises, or consists essentially of, or yet further consists of or has an amino acid sequence of SEQ ID NO: 8 or an equivalent thereof.

In some embodiments, the UBAP2L targeting agent does not bind to a region of the UBAP2L that corresponds to the glycine-rich motif (RGG domain). In some embodiments, the UBA domain comprises, or consists essentially of, or yet further consists of, or has a nucleotide sequence of SEQ ID NO: 9 or an equivalent thereof. In some embodiments, the UBA domain comprises, or consists essentially of, or yet further consists of, or has an amino acid sequence of SEQ ID NO: 10 or an equivalent thereof.

In some embodiments, the contacting is in vivo. Alternatively, the contacting is in vitro.

In some embodiments, the mammalian neuronal cell is a cell of the group of spinal group neuron and brain neuron. In some embodiments, the spinal group neuron is a neuron of the group of sensory, motor, and interneurons. In some embodiments, the spinal group neuron is a motor neuron.

In some embodiments, the method further comprises, or further consists essentially of, or further consists of, subjecting the cell to an environmental stressor. In some embodiments, the environmental stressor is selected from the group of temperature, exposure to a toxin, and mechanical damage. In some embodiments, the environmental stressor is an increase in temperature. In some embodiments, the temperature is increased by 5, 6, 7, 8, 9, 10, 11, 12, 13, 14, 15, 16, 17, 18, 19, or 20 or more degrees Celsius. In some embodiments, the environmental stresser is exposure to a toxin. In some embodiments, the toxin is selected from sodium arsenite and thapsigargin.

In some embodiments, the method further comprises, or further consists essentially of, or yet further consists of, detecting SG formation. In some embodiments, detecting SG formation comprises, or consists essentially of, or yet further consists of, immunofluorescence imaging. In some embodiments, detecting SG formation comprises, or consists essentially of, or yet further consists of, contacting the cell with an antibody that binds to a RNA binding protein (RBP). In some embodiments, the RBP is G3BP Stress Granule Assembly Factor 1 (G3BP1) or Fragile X Mental Retardation 1 (FMR1).

In some embodiments, the method further comprises, or further consists essentially of, or yet further consists of, detecting the expression level of UBAP2L. In some embodiments, the method further comprises, or further consists essentially of, or yet further consists of, detecting the expression level of one or more RNA binding proteins (RBPs).

In some embodiments, the expression level of UBAP2L or the RBPs is detected in a sample from the subject. In some embodiments, the sample comprises, or consists essentially of, or yet further consists of, a bodily fluid. Alternatively, the sample comprises, or consists essentially of, or yet further consists of, a tissue or cell.

In some embodiments, the ubiquitin associated protein 2-like (UBAP2L) targeting agent that specifically targets one or more regions within an UBAP2L protein, mRNA, or gene is selected from the group of: an antisense oligonucleotide (ASO) that hybridizes to a region within an UBAP2L messenger RNA (mRNA) molecule; a RNA interference (RNAi) molecule that hybridizes to a region within an UBAP2L messenger RNA (mRNA) molecule; and a Clustered Regularly Interspaced Short Palindromic Repeat (CRISPR) system that targets an UBAP2L messenger RNA (mRNA) molecule.

In some embodiments, the ubiquitin associated protein 2-like (UBAP2L) targeting agent that specifically targets one or more regions within an UBAP2L protein, mRNA, or gene is selected from the group of: an antisense oligonucleotide (ASO) that hybridizes to a region within an UBAP2L gene; a RNA interference (RNAi) molecule that hybridizes to a region within an UBAP2L gene; and a Clustered Regularly Interspaced Short Palindromic Repeat (CRISPR) system that targets a nucleic acid molecule comprising, or consisting essentially of, or yet further consisting of, a nucleotide sequence of NCBI Reference No. NC_000001.11 or an equivalent thereof.

In some embodiments, the UBAP2L gene comprises, or consists essentially of, or consists of, or has the nucleotide sequence of NCBI Reference No. NC_000001.11 or an equivalent thereof.

In some embodiments, the CRISPR system comprises, or consists essentially of, or yet further consists of: (a) an oligonucleotide encoding a CRISPR associated endonuclease (Cas) protein; and (b) an oligonucleotide comprising, or consisting essentially of, or yet further consisting of, (i) a first region that hybridizes to an ubiquitin associated protein 2-like (UBAP2L) gene; and (ii) a scaffold sequence.

Treating Neurodegenerative Disorders

As discussed herein, the formation of stress granules has been implicated in the development and progression of neurodegenerative disorders. Based on the role of UBAP2L as an essential regulator of SG formation, disclosed herein are methods for treating a neurodegenerative disorder in a subject in need thereof. Generally, the method comprises, or consists essentially of, or yet further consists of, administering to the subject an effective amount of an ubiquitin associated protein 2-like (UBAP2L) targeting agent that specifically targets one or more regions within an UBAP2L protein, mRNA, or gene.

In some embodiments, the UBAP2L protein comprises, or consists essentially of, or consists of, or has the amino acid sequence of SEQ ID NO: 6 or an equivalent thereof. In some embodiments, the UBAP2L mRNA comprises, or consists essentially of, or consists of, or has the nucleotide sequence of SEQ ID NO: 5 or an equivalent thereof. In some embodiments, the UBAP2L gene comprises, or consists essentially of, or consists of, or has the nucleotide sequence of NCBI Reference No. NC_000001.11 or an equivalent thereof.

In some embodiments, UBAP2L targeting agent specifically targets one or more regions within bases 617 to 3889 of an UBAP2L messenger RNA (mRNA) molecule having a nucleotide sequence of SEQ ID NO: 5 or an equivalent thereof.

In some embodiments, the UBAP2L targeting agent does not bind to a region of the UBAP2L that corresponds to the ubiquitin associated (UBA) domain. In some embodiments, the UBA domain comprises, or consists essentially of, or consists of, or has a nucleotide sequence of SEQ ID NO: 7 or an equivalent thereof. In some embodiments, the UBA domain comprises, or consists essentially of, or consists of, or has an amino acid sequence of SEQ ID NO: 8 or an equivalent thereof.

In some embodiments, the UBAP2L targeting agent does not bind to a region of the UBAP2L that corresponds to the glycine-rich motif (RGG domain). In some embodiments, the UBA domain comprises, or consists essentially of, or consists of, or has a nucleotide sequence of SEQ ID NO: 9 or an equivalent thereof. In some embodiments, the UBA domain comprises, or consists essentially of, or consists of, or has an amino acid sequence of SEQ ID NO: 10 or an equivalent thereof.

In some embodiments, the UBAP2L targeting agent is selected from the group of: an antisense oligonucleotide (ASO) that hybridizes to a region within an UBAP2L messenger RNA (mRNA) molecule comprising, or consisting essentially of, or yet further consisting of, SEQ ID NO: 5 or an equivalent thereof; a RNA interference (RNAi) molecule that hybridizes to a region within an UBAP2L messenger RNA (mRNA) molecule comprising, or consisting essentially of, or yet further consisting of, SEQ ID NO: 5 or an equivalent thereof; and a Clustered Regularly Interspaced Short Palindromic Repeat (CRISPR) system that targets a nucleic acid molecule comprising, or consisting essentially of, or yet further consisting of, a nucleotide sequence of SEQ ID NO: 5 or an equivalent thereof.

In some embodiments, the CRISPR system comprises, or consists essentially of, or yet further consists of: (a) an oligonucleotide encoding a CRISPR associated endonuclease (Cas) protein; and (b) an oligonucleotide comprising, or consisting essentially of, or yet further consisting of, (i) a first region that hybridizes to an ubiquitin associated protein 2-like (UBAP2L) gene; and (ii) a scaffold sequence.

In some embodiments, the ASO and/or RNAi molecule hybridizes to a region within bases 620 to 2500 of an UBAP2L messenger RNA (mRNA) molecule having the nucleotide sequence of SEQ ID NO: 5 or an equivalent thereof. In some embodiments, the ASO and/or RNAi molecule hybridizes to a region within bases 700 to 2200 of an UBAP2L messenger RNA (mRNA) molecule having the nucleotide sequence of SEQ ID NO: 5 or an equivalent thereof. In some embodiments, the ASO and/or RNAi molecule hybridizes to a region within bases 600 to 800 of an UBAP2L messenger RNA (mRNA) molecule having the nucleotide sequence of SEQ ID NO: 5 or an equivalent thereof. In some embodiments, the ASO and/or RNAi molecule hybridizes to a region within bases 600 to 700 of an UBAP2L messenger RNA (mRNA) molecule having the nucleotide sequence of SEQ ID NO: 5 or an equivalent thereof. In some embodiments, the ASO and/or RNAi molecule hybridizes to a region within bases 650 to 700 of an UBAP2L messenger RNA (mRNA) molecule having the nucleotide sequence of SEQ ID NO: 5 or an equivalent thereof. In some embodiments, the ASO and/or RNAi molecule hybridizes to a region within bases 2000 to 2200 of an UBAP2L messenger RNA (mRNA) molecule having the nucleotide sequence of SEQ ID NO: 5 or an equivalent thereof. In some embodiments, the ASO and/or RNAi molecule hybridizes to a region within bases 2100 to 2200 of an UBAP2L messenger RNA (mRNA) molecule having the nucleotide sequence of SEQ ID NO: 5 or an equivalent thereof. In some embodiments, the ASO and/or RNAi molecule hybridizes to a region within bases 2150 to 2200 of an UBAP2L messenger RNA (mRNA) molecule having the nucleotide sequence of SEQ ID NO: 5 or an equivalent thereof.

In some embodiments, the ASO and/or RNAi molecule do not hybridize to a region of the UBAP2L mRNA molecule that encodes for an ubiquitin associated (UBA) domain or arginine and glycine-rich motif (RGG domain). In some embodiments, the UBA domain comprises, or consists essentially of, or consists of, or has a nucleotide sequence of SEQ ID NO: 7 or an equivalent thereof. In some embodiments, the UBA domain comprises, or consists essentially of, or consists of, or has an amino acid sequence of SEQ ID NO: 8 or an equivalent thereof. In some embodiments, the UBA domain comprises, or consists essentially of, or consists of, or has a nucleotide sequence of SEQ ID NO: 9 or an equivalent thereof. In some embodiments, the UBA domain comprises, or consists essentially of, or consists of, or has an amino acid sequence of SEQ ID NO: 10 or an equivalent thereof.

In some embodiments, the RNAi molecule is selected from a microRNA (miRNA) or small interfering RNA (siRNA). In some embodiments, the RNAi molecule comprises, or consists essentially of, or consists of, or has the nucleotide sequence of SEQ ID NO: 1 or SEQ ID NO: 2.

In some embodiments, the agent is a CRISPR system. In some embodiments, the first region of the CRISPR system does not hybridize to a region of the UBAP2L gene that encodes for an ubiquitin associated (UBA) domain or arginine and glycine-rich motif (RGG domain). In some embodiments, the Cas protein is a Cas9 protein.

In some embodiments, the subject has been identified for treatment by detecting expression of UBAP2L in a neuronal sample isolated from the subject.

Monitoring Progression of a Neurodegenerative Disorder

Disclosed herein are methods of monitoring disease progression in a subject suffering from a neurodegenerative disorder. Generally, the method comprises, or consists essentially of, or consists of (a) analyzing at least two biological samples taken from the subject at different time points to detect level of expression of ubiquitin associated protein 2-like (UBAP2L); and (b) comparing the detected UBAP2L expression level in the biological samples taken at different time points.

In some embodiments, an increase in the detected UBAP2L expression level over time is indicative that the subject's neurodegenerative disorder is progressing. In some embodiments, an increase in the UBAP2L expression level by at least 5%, 10%, 15%, 20%, 25%, 30%, 35%, 40%, 45%, 50%, 55%, 60%, 65%, 70%, 75%, 80%, 85%, 90%, 95%, 100%, 110%, 115%, 120%, 125%, 130%, 135%, 140%, 145%, or 150% is indicative that the subject's neurodegenerative disorder is not progressing. In some embodiments, an increase in the UBAP2L expression level by at least 10% is indicative that the subject's neurodegenerative disorder is not progressing. In some embodiments, an increase in the UBAP2L expression level by at least 20% is indicative that the subject's neurodegenerative disorder is not progressing. In some embodiments, an increase in the UBAP2L expression level by at least 30% is indicative that the subject's neurodegenerative disorder is not progressing. In some embodiments, an increase in the UBAP2L expression level by at least 40% is indicative that the subject's neurodegenerative disorder is not progressing. In some embodiments, an increase in the UBAP2L expression level by at least about 1.5-fold, 2-fold, 2.5-fold, 3-fold, 3.5-fold, 4-fold, 4.5-fold, 5-fold, 6-fold, 7-fold, 8-fold, 9-fold, or 10-fold is indicative that the subject's neurodegenerative disorder is not progressing. In some embodiments, an increase in the UBAP2L expression level by at least 1.5-fold is indicative that the subject's neurodegenerative disorder is not progressing. In some embodiments, an increase in the UBAP2L expression level by at least 2-fold is indicative that the subject's neurodegenerative disorder is not progressing. In some embodiments, an increase in the UBAP2L expression level by at least 3-fold is indicative that the subject's neurodegenerative disorder is not progressing. In some embodiments, the increase in the UBAP2L expression level is based on a comparison of the subject's UBAP2L expression level before and after administration of a neurodegenerative therapy. In some embodiments, the increase in the UBAP2L expression level is based on a comparison of the subject's UBAP2L expression level during administration of a neurodegenerative therapy. In some embodiments, the increase in the UBAP2L expression level is based on a comparison of the subject's UBAP2L expression level before and after administration of an UBAP2L targeting agent. In some embodiments, the increase in the UBAP2L expression level is based on a comparison of the subject's UBAP2L expression level during administration of an UBAP2L targeting agent.

In some embodiments, a decrease in the detected UBAP2L expression level over time is indicative that the subject's neurodegenerative is not progressing. In some embodiments, a decrease in the UBAP2L expression level by at least 5%, 10%, 15%, 20%, 25%, 30%, 35%, 40%, 45%, 50%, 55%, 60%, 65%, 70%, 75%, 80%, 85%, 90%, 95%, 100%, 110%, 115%, 120%, 125%, 130%, 135%, 140%, 145%, or 150% is indicative that the subject's neurodegenerative disorder is not progressing. In some embodiments, a decrease in the UBAP2L expression level by at least 10% is indicative that the subject's neurodegenerative disorder is not progressing. In some embodiments, a decrease in the UBAP2L expression level by at least 20% is indicative that the subject's neurodegenerative disorder is not progressing. In some embodiments, a decrease in the UBAP2L expression level by at least 30% is indicative that the subject's neurodegenerative disorder is not progressing. In some embodiments, a decrease in the UBAP2L expression level by at least 40% is indicative that the subject's neurodegenerative disorder is not progressing. In some embodiments, a decrease in the UBAP2L expression level by at least about 1.5-fold, 2-fold, 2.5-fold, 3-fold, 3.5-fold, 4-fold, 4.5-fold, 5-fold, 6-fold, 7-fold, 8-fold, 9-fold, or 10-fold is indicative that the subject's neurodegenerative disorder is not progressing. In some embodiments, a decrease in the UBAP2L expression level by at least 1.5-fold is indicative that the subject's neurodegenerative disorder is not progressing. In some embodiments, a decrease in the UBAP2L expression level by at least 2-fold is indicative that the subject's neurodegenerative disorder is not progressing. In some embodiments, a decrease in the UBAP2L expression level by at least 3-fold is indicative that the subject's neurodegenerative disorder is not progressing. In some embodiments, the decrease in the UBAP2L expression level is based on a comparison of the subject's UBAP2L expression level before and after administration of a neurodegenerative therapy. In some embodiments, the decrease in the UBAP2L expression level is based on a comparison of the subject's UBAP2L expression level during administration of a neurodegenerative therapy. In some embodiments, the decrease in the UBAP2L expression level is based on a comparison of the subject's UBAP2L expression level before and after administration of an UBAP2L targeting agent. In some embodiments, the decrease in the UBAP2L expression level is based on a comparison of the subject's UBAP2L expression level during administration of an UBAP2L targeting agent.

In some embodiments, the method further comprises, or further consists essentially of, or further consists of, administering a neurodegenerative disorder therapy. Alternatively, or additionally, the method further comprises, or further consists essentially of, or further consists of, increasing the dose or dosing frequency of the neurodegenerative disorder therapy if the neurodegenerative disorder is progressing. In some embodiments, the method further comprises, or further consists essentially of, or further consists of, reducing the dose or dosing frequency of the neurodegenerative disorder therapy if the neurodegenerative disorder is not progressing.

Determining Efficacy of a Neurodegenerative Disorder Therapy

Disclosed herein are methods of determining the efficacy of a neurodegenerative disorder therapy in a subject suffering from a neurodegenerative disorder. Generally, the method comprises, or consists essentially of, or consists of, (a) administering an effective amount of the neurodegenerative disorder therapy; and (b) analyzing at least two biological samples taken from the subject before and after administration of the neurodegenerative therapy for the level of expression of ubiquitin associated protein 2-like (UBAP2L).

In some embodiments, an increase in the detected UBAP2L expression level over time is indicative that the subject's neurodegenerative disorder is progressing. In some embodiments, an increase in the UBAP2L expression level by at least 5%, 10%, 15%, 20%, 25%, 30%, 35%, 40%, 45%, 50%, 55%, 60%, 65%, 70%, 75%, 80%, 85%, 90%, 95%, 100%, 110%, 115%, 120%, 125%, 130%, 135%, 140%, 145%, or 150% is indicative that the subject's neurodegenerative disorder is progressing. In some embodiments, an increase in the UBAP2L expression level by at least 10% is indicative that the subject's neurodegenerative disorder is progressing. In some embodiments, an increase in the UBAP2L expression level by at least 20% is indicative that the subject's neurodegenerative disorder is progressing. In some embodiments, an increase in the UBAP2L expression level by at least 30% is indicative that the subject's neurodegenerative disorder is progressing. In some embodiments, an increase in the UBAP2L expression level by at least 40% is indicative that the subject's neurodegenerative disorder is progressing. In some embodiments, an increase in the UBAP2L expression level by at least about 1.5-fold, 2-fold, 2.5-fold, 3-fold, 3.5-fold, 4-fold, 4.5-fold, 5-fold, 6-fold, 7-fold, 8-fold, 9-fold, or 10-fold is indicative that the subject's neurodegenerative disorder is progressing. In some embodiments, an increase in the UBAP2L expression level by at least 1.5-fold is indicative that the subject's neurodegenerative disorder is progressing. In some embodiments, an increase in the UBAP2L expression level by at least 2-fold is indicative that the subject's neurodegenerative disorder is progressing. In some embodiments, an increase in the UBAP2L expression level by at least 3-fold is indicative that the subject's neurodegenerative disorder is progressing. In some embodiments, the increase in the UBAP2L expression level is based on a comparison of the subject's UBAP2L expression level before and after administration of a neurodegenerative therapy. In some embodiments, the increase in the UBAP2L expression level is based on a comparison of the subject's UBAP2L expression level during administration of a neurodegenerative therapy. In some embodiments, the increase in the UBAP2L expression level is based on a comparison of the subject's UBAP2L expression level before and after administration of an UBAP2L targeting agent. In some embodiments, the increase in the UBAP2L expression level is based on a comparison of the subject's UBAP2L expression level during administration of an UBAP2L targeting agent.

In some embodiments, a decrease in the detected UBAP2L expression level over time is indicative that the subject's neurodegenerative is not progressing. In some embodiments, a decrease in the UBAP2L expression level by at least 5%, 10%, 15%, 20%, 25%, 30%, 35%, 40%, 45%, 50%, 55%, 60%, 65%, 70%, 75%, 80%, 85%, 90%, 95%, 100%, 110%, 115%, 120%, 125%, 130%, 135%, 140%, 145%, or 150% is indicative that the subject's neurodegenerative disorder is not progressing. In some embodiments, a decrease in the UBAP2L expression level by at least 10% is indicative that the subject's neurodegenerative disorder is not progressing. In some embodiments, a decrease in the UBAP2L expression level by at least 20% is indicative that the subject's neurodegenerative disorder is not progressing. In some embodiments, a decrease in the UBAP2L expression level by at least 30% is indicative that the subject's neurodegenerative disorder is not progressing. In some embodiments, a decrease in the UBAP2L expression level by at least 40% is indicative that the subject's neurodegenerative disorder is not progressing. In some embodiments, a decrease in the UBAP2L expression level by at least about 1.5-fold, 2-fold, 2.5-fold, 3-fold, 3.5-fold, 4-fold, 4.5-fold, 5-fold, 6-fold, 7-fold, 8-fold, 9-fold, or 10-fold is indicative that the subject's neurodegenerative disorder is not progressing. In some embodiments, a decrease in the UBAP2L expression level by at least 1.5-fold is indicative that the subject's neurodegenerative disorder is not progressing. In some embodiments, a decrease in the UBAP2L expression level by at least 2-fold is indicative that the subject's neurodegenerative disorder is not progressing. In some embodiments, a decrease in the UBAP2L expression level by at least 3-fold is indicative that the subject's neurodegenerative disorder is not progressing. In some embodiments, the decrease in the UBAP2L expression level is based on a comparison of the subject's UBAP2L expression level before and after administration of a neurodegenerative therapy. In some embodiments, the decrease in the UBAP2L expression level is based on a comparison of the subject's UBAP2L expression level during administration of a neurodegenerative therapy. In some embodiments, the decrease in the UBAP2L expression level is based on a comparison of the subject's UBAP2L expression level before and after administration of an UBAP2L targeting agent. In some embodiments, the decrease in the UBAP2L expression level is based on a comparison of the subject's UBAP2L expression level during administration of an UBAP2L targeting agent.

In some embodiments, the method further comprises, or further consists essentially of, or further consists of, administering one or more additional neurodegenerative disorder therapies. Alternatively, or additionally, the method further comprises, or further consists essentially of, or further consists of, increasing the dose or dosing frequency of the neurodegenerative disorder therapy if the neurodegenerative disorder is progressing. In some embodiments, the method further comprises, or further consists essentially of, or further consists of, reducing the dose or dosing frequency of the neurodegenerative disorder therapy if the neurodegenerative disorder is not progressing.

Neurodegenerative Disorders and Neurodegenerative Disorder Therapies

In some embodiments, the methods described herein are directed to treating a subject suffering from a neurodegenerative disorder, monitoring the progression of a neurodegenerative disorder in a subject, and/or determining the efficacy of a neurodegenerative disorder therapy. In some embodiments, the neurodegenerative disorder is characterized by the formation of stress granules. In some embodiments, the neurodegenerative disorder is amyotrophic lateral sclerosis (ALS) or dementia. In some embodiments, the dementia is selected from Alzheimer's disease (AD), frontotemporal lobar degeneration (FTLD), or Lewy body dementia (LBD). In some embodiments, the LBD is selected from dementia with Lewy bodies and Parkinson's disease (PD) dementia.

In some embodiments, the neurodegenerative disorder therapy (NDT) comprises, or consists essentially of, or consists of, any of the ASOs, RNAi molecules, CRISPR systems, RNA molecules, vectors, and cells described herein. Alternatively, or additionally, the NDT is a known therapy specific to the neurodegenerative disorder. For instance, the NDT is a therapy specific for the treatment of ALS or dementia. In some embodiments, the NDT is an anti-ALS therapy selected from riluzole (i.e., rilutek) or edaravone (i.e., radicava).

In some embodiments, the NDT treats a symptom of Alzheimer's disease. For instance, the NDT treats one or more cognitive symptoms of AD. In some embodiments, the NDT is selected from a cholinesterase inhibitor and memantine. Examples of cholinesterase inhibitors include, but are not limited to, Aricept (i.e., donepezil), Exelon (i.e., rivastigmine), and Razadyne (i.e., galantamine). Examples of memantine include Namenda. In some embodiments, the NDT comprises, or consists essentially of, or consists of, a choliserase inhibitor and memantine. In some embodiments, the NDT comprises, or consists essentially of, or consists of, donepezil and namzaric.

In some embodiments, the NDT treats FTLD. In some embodiments, the NDT is selected from a selective serotonin reuptake inhibitor (SSRI), antipsychotic agent, antianxiety drug, and a psychostimulant. Examples of SSRIs include, but are not limited to, citalopram (Celexa), escitalopram (Lexapro), fluoxetine (Prozac), paroxetine (Paxil, Pexeva), sertraline (Zoloft), and vilazodone (Viibryd). Examples of antipsychotic agents include, but are not limited to, olanzapine (Zyprexa) and quetiapine (Seroquel). Examples of antianxiety drugs include, but are not limited to, benzodiazapenes, such as lorazepam (Ativan®); alprazolam (Xanax®); clonazepam (Klonopin®); and diazepam (Valium®). Examples of psychostimulants include, but are not limited to, methylphenidate (Ritalin) and dextroamphetamine (Dexedrine).

In some embodiments, the NDT treats PD. In some embodiments, the NDT is selected from carbidopa-levodopa, dopamine agonists, MAO-B inhibitors, Catechol-O-methyltransferase (COMT) inhibitors, anticholinergics, and amantadine. Examples of dopamine agonists include, but are not limited to, pramipexole (Mirapex), ropinirole (Requip) and rotigotine (given as a patch, Neupro). Examples of MAO-B inhibitors include, but are not limited to, selegiline (Eldepryl, Zelapar) and rasagiline (Azilect). Examples of COMT inhibitors include, but are not limited to, entacapone (Colman) and tolcapone (Tasmar). Examples of anticholinergics include, but are not limited to, benztropine (Cogentin) and trihexyphenidyl.

In some embodiments, the NDT is administered in a composition. In some embodiments, the composition comprises, or consists essentially of, or consists of, the NDT and a naturally-occurring or non-naturally-occurring carrier, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri-, tetra-oligosaccharides, and oligosaccharides; derivatized sugars such as aldi-tols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like.

Subject

In some embodiments, the subject described herein is a mammal. In some embodiments, the mammal is of the group of human, non-human primate, rat, mouse, cow, pig, rabbit, horse, and goat. In some embodiments, the mammal is a human.

Samples

In some embodiments, the methods disclosed herein comprise analyzing one or more samples from a subject. In some embodiments, the sample is selected from blood, cerebrospinal fluid (CSF) or saliva. In some embodiments, the sample is a tissue sample. In some embodiments, the sample is blood. In some embodiments, the blood is peripheral blood, serum, or plasma.

In some embodiments, the sample is taken from the subject prior to the subject receiving a neurodegenerative disorder therapy (NDT). In other embodiments, the sample is taken from the subject after the subject has received a NDT.

In some embodiments, 1, 2, 3, 4, 5, 6, 7, 8, 9, or 10 or more samples are taken from the subject. In some embodiments, two or more samples are taken from the subject. In some embodiments, three or more samples are taken from the subject.

In some embodiments, the samples are taken from the subject once every week, 2 weeks, 3 weeks, 4 weeks, 5 weeks, 6 weeks, 2 months, 3 months, 4 months, 5 months or 6 months or more. In some embodiments, the samples are taken from the subject for a period of at least 2 weeks, 3 weeks, 1 month, 2 months, 3 months, 4 months, 5 months, or 6 months or more.

Antisense Oligonucleotides (ASOs)

Disclosed herein are UBAP2L targeting agents that reduce the expression level or inhibit the activity of UBAP2L. In some embodiments, the UBAP2L targeting agent is an antisense oligonucleotide (ASO).

In some embodiments, the ASO hybridizes to a region within a mRNA encoding an ubiquitin associated protein 2-like (UBAP2L) protein. In some embodiments, the ASO targets a mRNA encoding an ubiquitin associated protein 2-like (UBAP2L) protein.

Alternatively, or additionally, the ASO hybridizes to a region within a mRNA encoding an ubiquitin associated protein 2-like (UBAP2L) protein, wherein the ASO does not hybridize to a region of the mRNA that encodes for an ubiquitin associated (UBA) domain or arginine and glycine-rich motif (RGG domain). In some embodiments, the UBA domain comprises, or consists essentially of, or consists of, or has a nucleotide sequence of SEQ ID NO: 7 or an equivalent thereof. In some embodiments, the UBA domain comprises, or consists essentially of, or consists of, or has an amino acid sequence of SEQ ID NO: 8 or an equivalent thereof. In some embodiments, the RGG domain comprises, or consists essentially of, or consists of, or has a nucleotide sequence of SEQ ID NO: 9 or an equivalent thereof. In some embodiments, the RGG domain comprises, or consists essentially of, or consists of, or has an amino acid sequence of SEQ ID NO: 10 or an equivalent thereof.

In some embodiments, the ASO hybridizes to one or more regions within bases 617 to 3889 of an UBAP2L messenger RNA (mRNA) molecule having a nucleotide sequence of SEQ ID NO: 5 or an equivalent thereof.

In some embodiments, the ASO hybridizes to a region within a gene encoding an ubiquitin associated protein 2-like (UBAP2L) protein. In some embodiments, the ASO targets a gene encoding an ubiquitin associated protein 2-like (UBAP2L) protein.

Alternatively, or additionally, the ASO hybridizes to a region within a geneencoding an ubiquitin associated protein 2-like (UBAP2L) protein, wherein the ASO does not hybridize to a region of the gene that encodes for an ubiquitin associated (UBA) domain or arginine and glycine-rich motif (RGG domain). In some embodiments, the UBA domain comprises, or consists essentially of, or consists of, or has a nucleotide sequence of SEQ ID NO: 7 or an equivalent thereof. In some embodiments, the UBA domain comprises, or consists essentially of, or consists of, or has an amino acid sequence of SEQ ID NO: 8 or an equivalent thereof. In some embodiments, the RGG domain comprises, or consists essentially of, or consists of, or has a nucleotide sequence of SEQ ID NO: 9 or an equivalent thereof. In some embodiments, the RGG domain comprises, or consists essentially of, or consists of, or has an amino acid sequence of SEQ ID NO: 10 or an equivalent thereof.

In some embodiments, the ASO is 5 to 70 nucleotides in length. In some embodiments, the ASO is 5-60, 5-50, 8-50, 8-40, 5-30, 8-30, or 10-30 nucleotides in length.

RNAi Molecules

In some embodiments, the UBAP2L targeting agent is a RNA interference (RNAi) molecule. In some embodiments, the RNAi molecule targets a mRNA encoding a UBAP2L protein. In some embodiments, the RNAi molecule targets a gene encoding a UBAP2L protein.

In some embodiments, the RNAi molecule comprises, or consists essentially of, or consists of, or has the oligonucleotide sequence of SEQ ID NO: 1 or SEQ ID NO: 2 or an equivalent of each thereof.

Alternatively, or additionally, the RNAi molecule hybridizes to a region within a mRNA encoding an ubiquitin associated protein 2-like (UBAP2L) protein, wherein the RNAi molecule does not hybridize to a region of the mRNA that encodes for an ubiquitin associated (UBA) domain or arginine and glycine-rich motif (RGG domain). In some embodiments, the UBA domain comprises, or consists essentially of, or consists of, or has a nucleotide sequence of SEQ ID NO: 7 or an equivalent thereof. In some embodiments, the UBA domain comprises, or consists essentially of, or consists of, or has an amino acid sequence of SEQ ID NO: 8 or an equivalent thereof. In some embodiments, the RGG domain comprises, or consists essentially of, or consists of, or has a nucleotide sequence of SEQ ID NO: 9 or an equivalent thereof. In some embodiments, the RGG domain comprises, or consists essentially of, or consists of, or has an amino acid sequence of SEQ ID NO: 10 or an equivalent thereof.

In some embodiments, the RNAi molecule targets one or more regions within bases 617 to 3889 of an UBAP2L messenger RNA (mRNA) molecule having a nucleotide sequence of SEQ ID NO: 5 or an equivalent thereof.

In some embodiments, the RNAi molecule hybridizes to a region within a gene encoding an ubiquitin associated protein 2-like (UBAP2L) protein, wherein the RNAi molecule does not hybridize to a region of the gene that encodes for an ubiquitin associated (UBA) domain or arginine and glycine-rich motif (RGG domain). In some embodiments, the UBA domain comprises, or consists essentially of, or consists of, or has a nucleotide sequence of SEQ ID NO: 7 or an equivalent thereof. In some embodiments, the UBA domain comprises, or consists essentially of, or consists of, or has an amino acid sequence of SEQ ID NO: 8 or an equivalent thereof. In some embodiments, the RGG domain comprises, or consists essentially of, or consists of, or has a nucleotide sequence of SEQ ID NO: 9 or an equivalent thereof. In some embodiments, the RGG domain comprises, or consists essentially of, or consists of, or has an amino acid sequence of SEQ ID NO: 10 or an equivalent thereof.

In some embodiments, the RNAi molecule is 5 to 70 nucleotides in length. In some embodiments, the RNAi molecule is 5-60, 5-50, 8-50, 8-40, 5-30, 8-30, 10-30, 10-25, 15-25, or 20-25 nucleotides in length.

CRISPR Systems

In some embodiments, the UBAP2L targeting agent is a Clustered Regularly Interspaced Short Palindromic Repeat (CRISPR) system. In the CRISPR system, a guide-RNA (gRNA), in complex with the Cas protein, targets genomic sequences homologous to the gRNA. The gRNA sequence may be modified to target specific genes or regions of genes, thus enabling many targeted genome editing and regulation capabilities. In some embodiments, the CRISPR system comprises, or consists essentially of, or consists of, one or more gRNAs.

In some embodiments, the CRISPR system comprises, or consists essentially of, or consists of: (a) an oligonucleotide encoding a CRISPR associated endonuclease (Cas) protein; and (b) an oligonucleotide comprising, or consisting essentially of, or yet further consisting of, (i) a first region that hybridizes to an ubiquitin associated protein 2-like (UBAP2L) gene; and (ii) a scaffold sequence.

In some embodiments, the CRISPR system comprises, or consists essentially of, or consists of: (a) CRISPR associated endonuclease (Cas) protein; and (b) an oligonucleotide comprising, or consisting essentially of, or yet further consisting of, (i) a first region that hybridizes to an ubiquitin associated protein 2-like (UBAP2L) gene; and (ii) a scaffold sequence.

Further disclosed herein is a RNA molecule comprising, or consisting essentially of, or yet further consisting of, a Clustered Regularly Interspaced Short Palindromic Repeat (CRISPR) system comprising, or consisting essentially of, or yet further consisting of: (a) an oligonucleotide encoding a CRISPR associated endonuclease (Cas) protein; and (b) an oligonucleotide comprising, or consisting essentially of, or yet further consisting of, (i) a first region that hybridizes to an ubiquitin associated protein 2-like (UBAP2L) gene; and (ii) a scaffold sequence. In some embodiments, the RNA molecule is encapsulated in a nanoparticle.

In some embodiments, the first region of the CRISPR system comprises, or consists essentially of, or consists of, an oligonucleotide sequence of SEQ ID NO: 3 or SEQ ID NO: 4 or an equivalent thereof. Alternatively, or additionally, in some embodiments, the first region does not hybridize to a region of the UBAP2L gene that encodes for an ubiquitin associated (UBA) domain or arginine and glycine-rich motif (RGG domain). In some embodiments, the UBA domain comprises, or consists essentially of, or consists of, or has a nucleotide sequence of SEQ ID NO: 7 or an equivalent thereof. In some embodiments, the UBA domain comprises, or consists essentially of, or consists of, or has an amino acid sequence of SEQ ID NO: 8 or an equivalent thereof. In some embodiments, the UBA domain comprises, or consists essentially of, or consists of, or has a nucleotide sequence of SEQ ID NO: 9 or an equivalent thereof. In some embodiments, the UBA domain comprises, or consists essentially of, or consists of, or has an amino acid sequence of SEQ ID NO: 10 or an equivalent thereof.

In some embodiments, the first region of the CRISPR system comprises, or consists essentially of, or consists of, an oligonucleotide sequence that hybridizes to one or more regions within bases 617 to 3889 of an UBAP2L messenger RNA (mRNA) molecule having a nucleotide sequence of SEQ ID NO: 5 or an equivalent thereof.

In some embodiments, the oligonucleotide comprising, or consisting essentially of, or yet further consisting of, the first and second regions is referred to as a guide RNA (gRNA).

In some embodiments, the oligonucleotide comprises, or consists essentially of, or consists of RNA.

In some embodiments, the Cas protein is a Cas9 protein.

Vectors

Disclosed herein are vectors comprising, or consisting essentially of, or yet further consisting of, any of the ASOs, RNAi molecules, CRISPR systems, and RNA molecules disclosed herein.

In some embodiments, the vector comprises, or consists essentially of, or consists of, an ASO that hybridizes to a region within a mRNA encoding an ubiquitin associated protein 2-like (UBAP2L) protein, wherein the ASO is optionally linked to expression and/or regulatory elements.

In some embodiments, the vector comprises, or consists essentially of, or consists of, an ASO that hybridizes to a region within a mRNA encoding an ubiquitin associated protein 2-like (UBAP2L) protein, wherein the ASO does not hybridize to a region of the mRNA that encodes for an ubiquitin associated (UBA) domain or arginine and glycine-rich motif (RGG domain), wherein the ASO is optionally linked to expression and/or regulatory elements.

In some embodiments, the vector comprises, or consists essentially of, or consists of, an ASO that hybridizes to a region within a gene encoding an ubiquitin associated protein 2-like (UBAP2L) protein, wherein the ASO is optionally linked to expression and/or regulatory elements.

In some embodiments, the vector comprises, or consists essentially of, or consists of, an ASO that hybridizes to a region within a gene encoding an ubiquitin associated protein 2-like (UBAP2L) protein, wherein the ASO does not hybridize to a region of the gene that encodes for an ubiquitin associated (UBA) domain or arginine and glycine-rich motif (RGG domain), wherein the ASO is optionally linked to expression and/or regulatory elements.

In some embodiments, the vector comprises, or consists essentially of, or consists of, a RNAi molecule comprising, or consisting essentially of, or yet further consisting of, the oligonucleotide sequence of SEQ ID NO: 1 or SEQ ID NO: 2 or an equivalent of each thereof, wherein the RNAi molecule is optionally linked to expression and/or regulatory elements.

In some embodiments, the vector comprises, or consists essentially of, or consists of, a RNAi molecule that hybridizes to a region within a mRNA encoding an ubiquitin associated protein 2-like (UBAP2L) protein, wherein the RNAi molecule does not hybridize to a region of the mRNA that encodes for an ubiquitin associated (UBA) domain or arginine and glycine-rich motif (RGG domain), wherein the RNAi molecule is optionally linked to expression and/or regulatory elements.

In some embodiments, the vector comprises, or consists essentially of, or consists of, a RNAi molecule that hybridizes to a region within a gene encoding an ubiquitin associated protein 2-like (UBAP2L) protein, wherein the RNAi molecule is optionally linked to expression and/or regulatory elements.

In some embodiments, the vector comprises, or consists essentially of, or consists of, a RNAi molecule that hybridizes to a region within a gene encoding an ubiquitin associated protein 2-like (UBAP2L) protein, wherein the RNAi molecule does not hybridize to a region of the gene that encodes for an ubiquitin associated (UBA) domain or arginine and glycine-rich motif (RGG domain), wherein the RNAi molecule is optionally linked to expression and/or regulatory elements.

In some embodiments, the vector comprises, or consists essentially of, or consists of, a Clustered Regularly Interspaced Short Palindromic Repeat (CRISPR) system comprising, or consisting essentially of, or yet further consisting of: (a) an oligonucleotide encoding a CRISPR associated endonuclease (Cas) protein; and (b) an oligonucleotide comprising, or consisting essentially of, or yet further consisting of, (i) a first region that hybridizes to an ubiquitin associated protein 2-like (UBAP2L) gene; and (ii) a scaffold sequence, wherein one or more of the oligonucleotides of the CRISPR system is optionally linked to expression and/or regulatory elements.

Cells

Disclosed herein are host cells comprising, or consisting essentially of, or yet further consisting of, any of the ASOs, RNAi molecules, CRISPR systems, RNA molecules, and vectors disclosed herein.

In some embodiments, the isolated host cells comprise one or more of: (a) an antisense oligonucleotide (ASO) that hybridizes to a region within a mRNA encoding an ubiquitin associated protein 2-like (UBAP2L) protein, (b) an antisense oligonucleotide (ASO) that hybridizes to a region within a mRNA encoding an ubiquitin associated protein 2-like (UBAP2L) protein, wherein the ASO does not hybridize to a region of the mRNA that encodes for an ubiquitin associated (UBA) domain or arginine and glycine-rich motif (RGG domain), (c) a RNA interference (RNAi) molecule comprising, or consisting essentially of, or yet further consisting of, the oligonucleotide sequence of SEQ ID NO: 1 or SEQ ID NO: 2 or an equivalent of each thereof, (d) a RNA interference (RNAi) molecule that hybridizes to a region within a mRNA encoding an ubiquitin associated protein 2-like (UBAP2L) protein, wherein the RNAi molecule does not hybridize to a region of the mRNA that encodes for an ubiquitin associated (UBA) domain or arginine and glycine-rich motif (RGG domain), or (e) a vector comprising, or consisting essentially of, or yet further consisting of, (i) the ASO of (a) or (b); or (ii) the RNAi molecule of (c) or (d), wherein the ASO or RNAi molecule is optionally linked to expression and/or regulatory elements.

In some embodiments, the isolated host cells comprise one or more of: (a) an antisense oligonucleotide (ASO) comprising, or consisting essentially of, or yet further consisting of, the oligonucleotide sequence that hybridizes to a region within a gene encoding an ubiquitin associated protein 2-like (UBAP2L) protein, (b) an antisense oligonucleotide (ASO) that hybridizes to a region within a gene encoding an ubiquitin associated protein 2-like (UBAP2L) protein, wherein the ASO does not hybridize to a region of the gene that encodes for an ubiquitin associated (UBA) domain or arginine and glycine-rich motif (RGG domain), (c) a RNA interference (RNAi) molecule that hybridizes to a region within a gene encoding an ubiquitin associated protein 2-like (UBAP2L) protein, (d) a RNA interference (RNAi) molecule that hybridizes to a region within a gene encoding an ubiquitin associated protein 2-like (UBAP2L) protein, wherein the RNAi molecule does not hybridize to a region of the gene that encodes for an ubiquitin associated (UBA) domain or arginine and glycine-rich motif (RGG domain), or (e) a vector comprising, or consisting essentially of, or yet further consisting of, (i) the ASO of (a) or (b); or (ii) the RNAi molecule of (c) or (d), wherein the ASO or RNAi molecule is optionally linked to expression and/or regulatory elements.

In some embodiments, the isolated host cells comprise A) a Clustered Regularly Interspaced Short Palindromic Repeat (CRISPR) system comprising, or consisting essentially of, or yet further consisting of: (i) an oligonucleotide encoding a CRISPR associated endonuclease (Cas) protein; and (ii) an oligonucleotide comprising, or consisting essentially of, or yet further consisting of, (a) a first region that hybridizes to an ubiquitin associated protein 2-like (UBAP2L) gene; and (b) a scaffold sequence, (B) a RNA molecule comprising, or consisting essentially of, or yet further consisting of, the CRISPR system of (A), or (C) a vector comprising, or consisting essentially of, or yet further consisting of, the CRISPR system of (A).

In some embodiments, the cell is a prokaryotic cell. In some embodiments, the prokaryotic cell is a gram-positive bacteria. In some embodiments, the prokaryotic cell is a gram-negative bacteria. In some embodiments, the prokaryotic cell is an *Escherichia coli* (*E. coli*) cell.

In some embodiments, the cell is a eukaryotic cell. In some embodiments, the eukaryotic cell is a mammalian cell. In some embodiments, the mammalian cell is a human cell. In some embodiments, the human cell is a human embryonic kidney (HEK) cell. In some embodiments, the eukaryotic cell is an insect cell. In some embodiments, the eukaryotic cell is a yeast cell. In some embodiments, the yeast cell is a *Saccharomyces cerevisiae* cell.

Kits

Disclosed herein are kits comprising, or consisting essentially of, or yet further consisting of, any of the ASOs, RNAi molecules, CRISPR systems, RNA molecules, vectors, and/or host cells disclosed herein.

In some embodiments, the kit comprises, or consists essentially of, or consists of, (a) an antisense oligonucleotide (ASO) that hybridizes to a region within a mRNA encoding an ubiquitin associated protein 2-like (UBAP2L) protein and (b) instructions for use.

In some embodiments, the kit comprises, or consists essentially of, or consists of, (a) an antisense oligonucleotide (ASO) that hybridizes to a region within a mRNA encoding an ubiquitin associated protein 2-like (UBAP2L) protein, wherein the ASO does not hybridize to a region of the mRNA that encodes for an ubiquitin associated (UBA) domain or arginine and glycine-rich motif (RGG domain); and (b) instructions for use.

In some embodiments, the kit comprises, or consists essentially of, or consists of, (a) a vector comprising, or consisting essentially of, or yet further consisting of, an antisense oligonucleotide (ASO) that hybridizes to a region within a mRNA encoding an ubiquitin associated protein 2-like (UBAP2L) protein, wherein the ASO is optionally linked to expression and/or regulatory elements; and (b) instructions for use.

In some embodiments, the kit comprises, or consists essentially of, or consists of, (a) a vector comprising, or consisting essentially of, or yet further consisting of, an antisense oligonucleotide (ASO) that hybridizes to a region within a mRNA encoding an ubiquitin associated protein 2-like (UBAP2L) protein, wherein the ASO does not hybridize to a region of the mRNA that encodes for an ubiquitin associated (UBA) domain or arginine and glycine-rich motif (RGG domain), wherein the ASO is optionally linked to expression and/or regulatory elements; and (b) instructions for use.

In some embodiments, the kit comprises, or consists essentially of, or consists of, (a) a vector comprising, or consisting essentially of, or yet further consisting of, a RNAi molecule comprising, or consisting essentially of, or yet further consisting of, the oligonucleotide sequence of SEQ ID NO: 1 or SEQ ID NO: 2 or an equivalent of each thereof, wherein the RNAi molecule is optionally linked to expression and/or regulatory elements; and (b) instructions for use.

In some embodiments, the kit comprises, or consists essentially of, or consists of, (a) a vector comprising, or consisting essentially of, or yet further consisting of, a RNAi molecule that hybridizes to a region within a mRNA encoding an ubiquitin associated protein 2-like (UBAP2L) protein, wherein the RNAi molecule does not hybridize to a region of the mRNA that encodes for an ubiquitin associated (UBA) domain or arginine and glycine-rich motif (RGG domain), and wherein the RNAi molecule is optionally linked to expression and/or regulatory elements; and (b) instructions for use.

In some embodiments, the kit comprises, or consists essentially of, or consists of, (A) a vector comprising, or consisting essentially of, or yet further consisting of, a CRISPR system comprising, or consisting essentially of, or yet further consisting of: (i) an oligonucleotide encoding a CRISPR associated endonuclease (Cas) protein; and (ii) an oligonucleotide comprising, or consisting essentially of, or yet further consisting of, (a) a first region that hybridizes to an ubiquitin associated protein 2-like (UBAP2L) gene; and (b) a scaffold sequence, and wherein the CRISPR system is optionally linked to expression and/or regulatory elements; and (B) instructions for use. In some embodiments, the first region comprises, or consists essentially of, or consists of, an oligonucleotide sequence of SEQ ID NO: 3 or SEQ ID NO: 4 or an equivalent of each thereof. Alternatively, or additionally, in some embodiments, the first region does not hybridize to a region of the UBAP2L gene that encodes for an ubiquitin associated (UBA) domain or arginine and glycine-rich motif (RGG domain).

In some embodiments, the kit comprises, or consists essentially of, or consists of, (a) a RNA interference (RNAi) molecule comprising, or consisting essentially of, or yet further consisting of, the oligonucleotide sequence of SEQ ID NO: 1 or SEQ ID NO: 2 or an equivalent of each thereof; and (b) instructions for use.

In some embodiments, the kit comprises, or consists essentially of, or consists of, (a) a RNA interference (RNAi) molecule that hybridizes to a region within a mRNA encoding an ubiquitin associated protein 2-like (UBAP2L) protein, wherein the RNAi molecule does not hybridize to a region of the mRNA that encodes for an ubiquitin associated (UBA) domain or arginine and glycine-rich motif (RGG domain); and (b) instructions for use.

In some embodiments, the kit comprises, or consists essentially of, or consists of, (a) an antisense oligonucleotide (ASO) that hybridizes to a region within a gene encoding an ubiquitin associated protein 2-like (UBAP2L) protein and (b) instructions for use.

In some embodiments, the kit comprises, or consists essentially of, or consists of, (a) an antisense oligonucleotide (ASO) that hybridizes to a region within a gene encoding an ubiquitin associated protein 2-like (UBAP2L) protein, wherein the ASO does not hybridize to a region of the gene that encodes for an ubiquitin associated (UBA) domain or arginine and glycine-rich motif (RGG domain); and (b) instructions for use.

In some embodiments, the kit comprises, or consists essentially of, or consists of, (a) a vector comprising, or consisting essentially of, or yet further consisting of, an antisense oligonucleotide (ASO) that hybridizes to a region within a gene encoding an ubiquitin associated protein 2-like (UBAP2L) protein, wherein the ASO is optionally linked to expression and/or regulatory elements; and (b) instructions for use.

In some embodiments, the kit comprises, or consists essentially of, or consists of, (a) a vector comprising, or consisting essentially of, or yet further consisting of, an antisense oligonucleotide (ASO) that hybridizes to a region within a gene encoding an ubiquitin associated protein 2-like (UBAP2L) protein, wherein the ASO does not hybridize to a region of the gene that encodes for an ubiquitin associated (UBA) domain or arginine and glycine-rich motif (RGG domain), wherein the ASO is optionally linked to expression and/or regulatory elements; and (b) instructions for use.

In some embodiments, the kit comprises, or consists essentially of, or consists of, (a) a vector comprising, or consisting essentially of, or yet further consisting of, a RNAi molecule that hybridizes to a region within a gene encoding an ubiquitin associated protein 2-like (UBAP2L) protein, wherein the RNAi molecule is optionally linked to expression and/or regulatory elements; and (b) instructions for use.

In some embodiments, the kit comprises, or consists essentially of, or consists of, (a) a vector comprising, or consisting essentially of, or yet further consisting of, a RNAi molecule that hybridizes to a region within a gene encoding an ubiquitin associated protein 2-like (UBAP2L) protein, wherein the RNAi molecule does not hybridize to a region of the gene that encodes for an ubiquitin associated (UBA) domain or arginine and glycine-rich motif (RGG domain), and wherein the RNAi molecule is optionally linked to expression and/or regulatory elements; and (b) instructions for use.

In some embodiments, the kit comprises, or consists essentially of, or consists of, (a) an isolated host cell comprising, or consisting essentially of, or yet further consisting of, one or more of: (i) antisense oligonucleotide (ASO) that hybridizes to a region within a mRNA encoding an ubiquitin associated protein 2-like (UBAP2L) protein; (ii) an antisense oligonucleotide (ASO) that hybridizes to a region within a mRNA encoding an ubiquitin associated protein 2-like (UBAP2L) protein, wherein the ASO does not hybridize to a region of the mRNA that encodes for an ubiquitin associated (UBA) domain or arginine and glycine-rich motif (RGG domain); (iii) a RNA interference (RNAi) molecule comprising, or consisting essentially of, or yet further consisting of, the oligonucleotide sequence of SEQ ID NO: 1 or SEQ ID NO: 2 or an equivalent of each thereof; (iv) a RNA interference (RNAi) molecule that hybridizes to a region within a mRNA encoding an ubiquitin associated protein 2-like (UBAP2L) protein, wherein the RNAi molecule does not hybridize to a region of the mRNA that encodes for an ubiquitin associated (UBA) domain or arginine and glycine-rich motif (RGG domain); or (v) a vector comprising, or consisting essentially of, or yet further consisting of, any of (i)-(iv); and (b) instructions for use.

In some embodiments, the kit comprises, or consists essentially of, or consists of, (a) an isolated host cell comprising, or consisting essentially of, or yet further consisting of, one or more of: (i) antisense oligonucleotide (ASO) that hybridizes to a region within a gene encoding an ubiquitin associated protein 2-like (UBAP2L) protein; (ii) an antisense oligonucleotide (ASO) that hybridizes to a region within a gene encoding an ubiquitin associated protein 2-like (UBAP2L) protein, wherein the ASO does not hybridize to a region of the gene that encodes for an ubiquitin associated (UBA) domain or arginine and glycine-rich motif (RGG domain); (iii) a RNA interference (RNAi) molecule that hybridizes to a region within a gene encoding an ubiquitin associated protein 2-like (UBAP2L) protein; (iv) a RNA interference (RNAi) molecule that hybridizes to a region within a gene encoding an ubiquitin associated protein 2-like (UBAP2L) protein, wherein the RNAi molecule does not hybridize to a region of the gene that encodes for an ubiquitin associated (UBA) domain or arginine and glycine-rich motif (RGG domain); or (v) a vector comprising, or consisting essentially of, or yet further consisting of, any of (i)-(iv); and (b) instructions for use.

In some embodiments, the kit comprises, or consists essentially of, or consists of, (I) an isolated host cell comprising, or consisting essentially of, or yet further consisting of, one or more of: (A) one or more of: (i) a Clustered Regularly Interspaced Short Palindromic Repeat (CRISPR) system comprising, or consisting essentially of, or yet further consisting of: (a) an oligonucleotide encoding a CRISPR associated endonuclease (Cas) protein; and (b) an oligonucleotide comprising, or consisting essentially of, or yet further consisting of, (1) a first region that hybridizes to an ubiquitin associated protein 2-like (UBAP2L) gene; and (2) a scaffold sequence; (ii) a RNA molecule comprising, or consisting essentially of, or yet further consisting of, the CRISPR system of (i); or (iii) a vector comprising, or consisting essentially of, or yet further consisting of, (i) or (ii); and (II) instructions for use. In some embodiments, the first region comprises, or consists essentially of, or consists of, an oligonucleotide sequence of SEQ ID NO: 3 or SEQ ID NO: 4 or an equivalent of each thereof. Alternatively, or additionally, in some embodiments, the first region does not hybridize to a region of the UBAP2L gene that encodes for an ubiquitin associated (UBA) domain or arginine and glycine-rich motif (RGG domain).

In some embodiments, the kit comprises, or consists essentially of, or consists of, (A) a Clustered Regularly Interspaced Short Palindromic Repeat (CRISPR) system comprising, or consisting essentially of, or yet further consisting of: (i) CRISPR associated endonuclease (Cas) protein; and (ii) an oligonucleotide comprising, or consisting essentially of, or yet further consisting of, (a) a first region that hybridizes to an ubiquitin associated protein 2-like (UBAP2L) gene; and (b) a scaffold sequence; and (B) instructions for use. In some embodiments, the first region comprises, or consists essentially of, or consists of, an oligonucleotide sequence of SEQ ID NO: 3 or SEQ ID NO: 4 or an equivalent of each thereof. Alternatively, or additionally, in some embodiments, the first region does not hybridize to a region of the UBAP2L gene that encodes for an ubiquitin associated (UBA) domain or arginine and glycine-rich motif (RGG domain). In some embodiments, the oligonucleotide comprises, or consists essentially of, or consists of RNA.

In some embodiments, the kit comprises, or consists essentially of, or consists of, (A) an RNA molecule comprising, or consisting essentially of, or yet further consisting of, (i) a Clustered Regularly Interspaced Short Palindromic Repeat (CRISPR) system comprising, or consisting essentially of, or yet further consisting of: (a) an oligonucleotide encoding a CRISPR associated endonuclease (Cas) protein; and (b) an oligonucleotide comprising, or consisting essentially of, or yet further consisting of, (1) a first region that hybridizes to an ubiquitin associated protein 2-like (UBAP2L) gene; and (2) a scaffold sequence; and (B) instructions for use. In some embodiments, the first region comprises, or consists essentially of, or consists of, an oligonucleotide sequence of SEQ ID NO: 3 or SEQ ID NO: 4 or an equivalent of each thereof. Alternatively, or additionally, in some embodiments, the first region does not hybridize to a region of the UBAP2L gene that encodes for an ubiquitin associated (UBA) domain or arginine and glycine-rich motif (RGG domain). In some embodiments, the RNA molecule is encapsulated in a nanoparticle.

EXAMPLES

In this study, Applicant uses a combination of ascorbate peroxidase (APEX)-mediated in vivo proximity labeling (Rhee et al., 2013) with quantitative mass spectrometry (MS) and an RBP-focused immunofluorescence (IF) approach to comprehensively and significantly expand the repertoire of known SG proteins across different cell types, stress conditions, and disease states. Applicant shows that SG proteins form a dense protein interaction network (PIN) in unstressed cells that is poised to enable rapid SG assembly in response to stress. In addition, Applicant finds that SGs in neuronal cells are particularly diverse in composition and contain numerous protein quality control (PQC) factors. Applicant reveals aberrant composition, behavior, and subcellular localization of SGs in motor neurons derived from stem cell models harboring ALS-associated mutations in HNRNPA2B1 and C9orf72. By systematically integrating our refined SG proteome with published neurodegeneration-relevant datasets, Applicant provides a framework for further investigations into the molecular underpinnings of SG biology and how it relates to human disease. To underscore the potential of identifying unexpected disease-relevant factors among SG proteins, Applicant shows that known and previously unknown SG components modify neurotoxicity in Drosophila models of FUS-, TDP-43-, and C9orf72-mediated degeneration. Applicant characterizes one of these, UBAP2L, as an essential, disordered, and highly aggregation-prone SG protein that can modulate ALS phenotypes in vivo.

Example 1

UBAP2L and Stress Granule Formation

Stress granules (SGs) are transient ribonucleoprotein (RBP) aggregates that form during cellular stress and are increasingly implicated in human neurodegeneration. To study the proteome and compositional diversity of SGs in different cell types and in the context of neurodegeneration-linked mutations, Applicant used ascorbate peroxidase (APEX) proximity labeling, mass spectrometry, and immunofluorescence to identify ~150 previously unknown human SG components. A highly integrated, pre-existing SG protein interaction network in unstressed cells facilitates rapid coalescence into larger SGs. Approximately 20% of SG diversity is stress or cell-type dependent, with neuronal SGs displaying a particularly complex repertoire of proteins enriched in chaperones and autophagy factors. Strengthening the link between SGs and neurodegeneration, Applicant demonstrates aberrant dynamics, composition, and subcellular distribution of SGs in cells from amyotrophic lateral sclerosis (ALS) patients. Using three Drosophila ALS/FTD models, Applicant identifies SG-associated modifiers of neurotoxicity in vivo. Altogether, our results highlight SG proteins as central to understanding and ultimately targeting neurodegeneration.

Figures 8A, 8B, 8C, 8D, 8E:
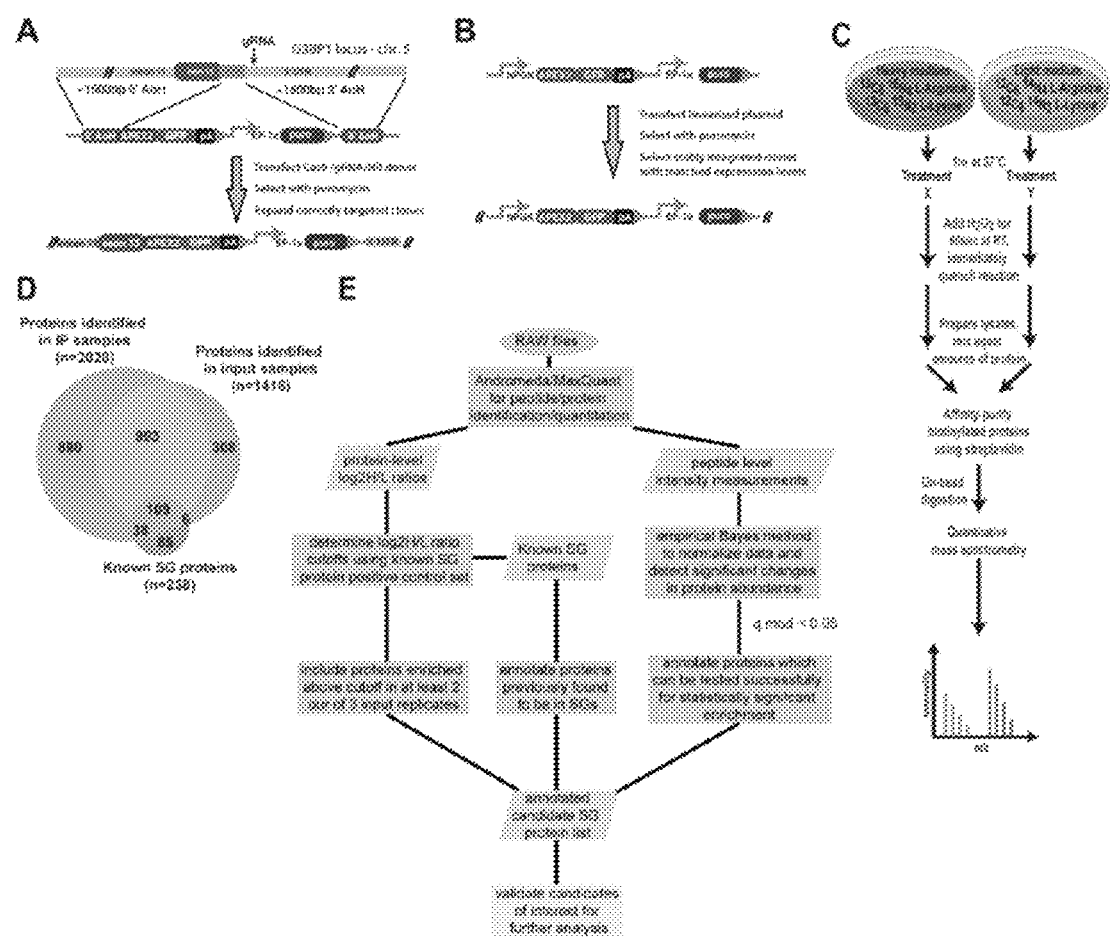
FIGS. 8A-8E: APEX Cell Line Generation, MS Experimental Design, and Data and Analysis, Related to FIG. 1.

Endogenously Tagged G3BP1-APEX-GFP Allows for Specific Biotin Labeling of SG Proteins To investigate the protein composition of SGs in living cells, Applicant performed proximity labeling using an engineered ascorbate peroxidase (APEX2) fused to the well-characterized SG protein G3BP1 (FIG. 1A). Applicant used CRISPR/Cas9-directed genome engineering to insert APEX2-GFP into the endogenous G3BP1 locus in HEK293T cells (FIG. 8A). The resulting G3BP1APEX2-GFP fusion protein allows visualization of SGs upon sodium arsenite ($NaAsO_2$) exposure, as well as robust and rapid biotin labeling of SG proteins in the presence of biotin-phenol (BP) and hydrogen peroxide ($H_2O_2$) (FIG. 1B and FIG. 1C). As a specificity control, cells with constitutive expression of cytoplasmic-localized APEX2 (NES-APEX2-GFP) (FIG. 8B) show a diffuse GFP signal and a biotinylation pattern that is unaffected by $NaAsO_2$ (FIG. 1B and FIG. 1C).

Identification of Stress-Dependent and Independent SG Proteomes Using Quantitative Proteomics Since G3BP1 is essential for SG formation and robustly localizes to SGs, Applicant reasoned that defining the interactome proximal to G3BP1 under stress conditions approximates the SG proteome. Applicant employed a series of quantitative proteomics experiments (FIG. 8C) to systematically identify three classes of G3BP1 interacting proteins in stressed and unstressed cells: (1) stress-independent interactors, which associate with G3BP1 independently of stress; (2) stress-dependent partners, which associate with G3BP1 only under stress; and (3) stress-sensitive interactors, whose association with G3BP1 is lost or weakened during stress (FIG. 1D).

Figures 2A, 2B, 2C, 2D, 2E:
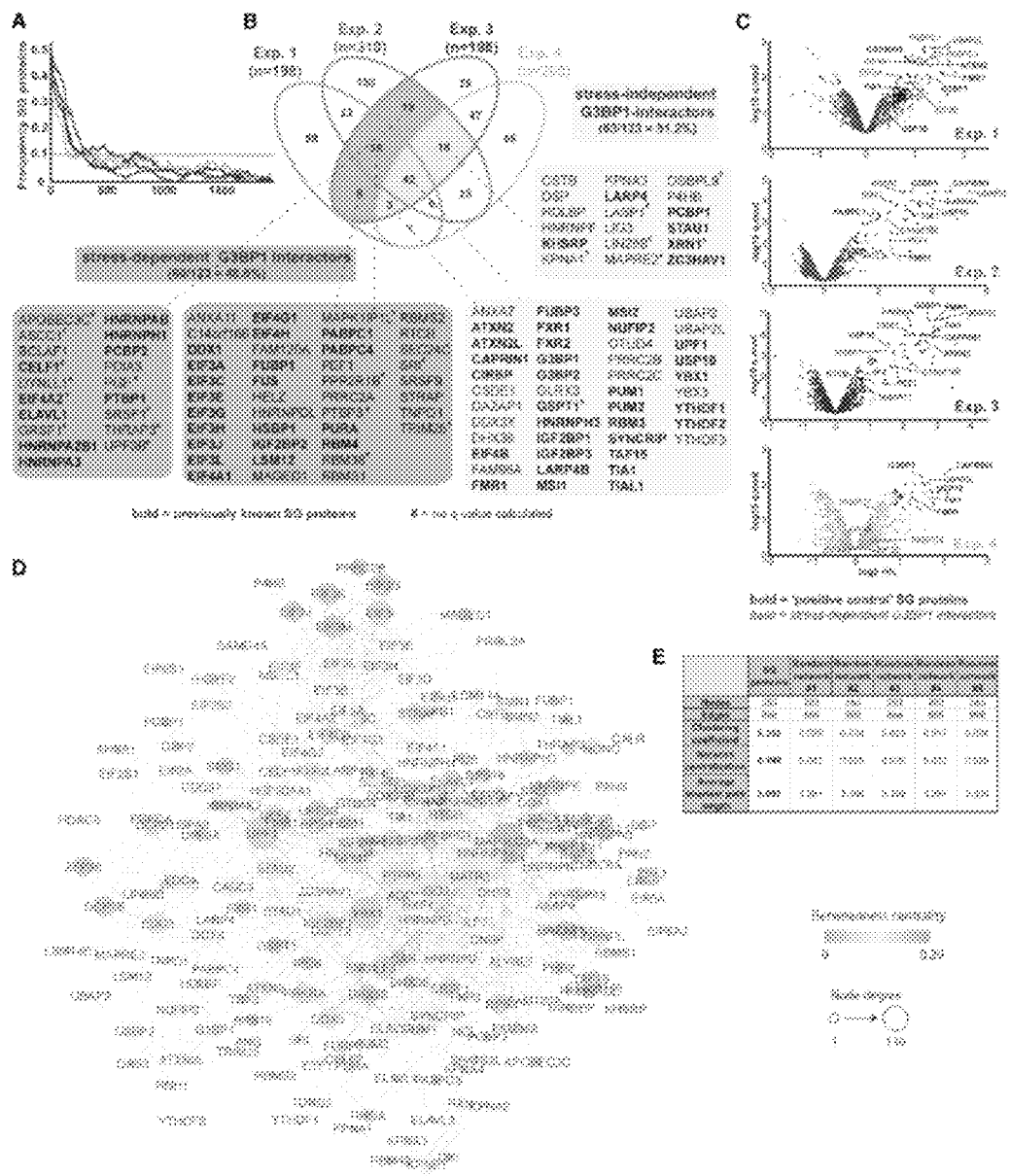
FIGS. 2A-2E: SG-APEX Identifies Known and Previously Unknown SG Proteins within a Dense Interaction Network.
Figures 9A, 9B:
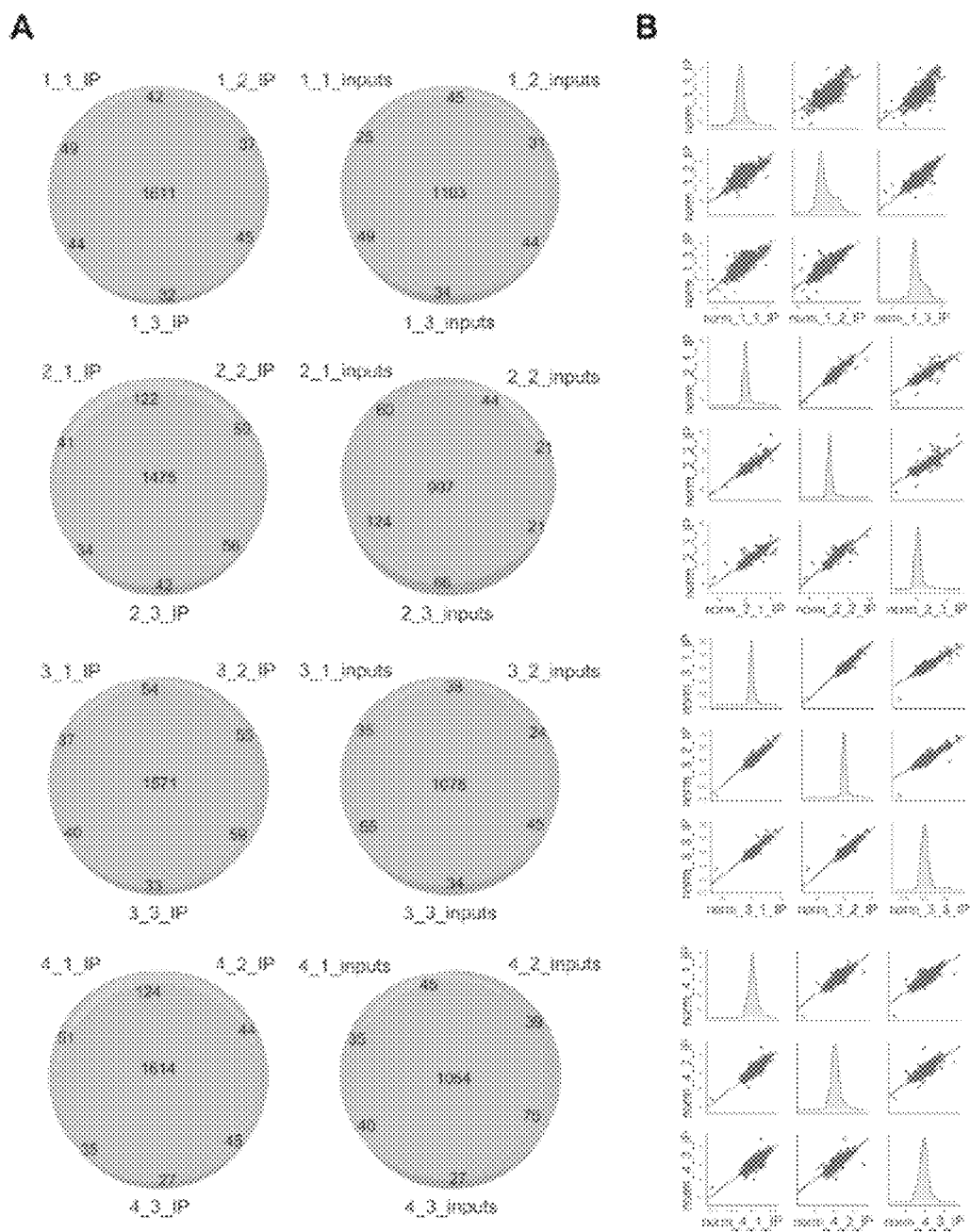
FIGS. 9A-9B: Reproducibility of Protein Identification and Quantitation across Replicates, Related to FIG. 1.

To distinguish these interactors, Applicant pursued four experimental schemes (FIG. 1E). First, to identify stress-dependent G3BP1 interactors, Applicant characterized biotinylated proteins in stressed versus unstressed G3BP1-APEX2-GFP cells (experiment 1). Next, Applicant compared lysates from stressed G3BP1-APEX2-GFP cells incubated with BP to lysates of identically treated cells for which the BP substrate was omitted (experiment 2). Third, to control for diffuse cytoplasmic labeling by G3BP1-APEX2-GFP, Applicant also compared lysates from stressed G3BP1-APEX2-GFP and NES-APEX2-GFP cells (experiment 3). Last, to define stress-independent as well as stress-sensitive G3BP1 interactors, Applicant profiled lysates from unstressed G3BP1-APEX2-GFP and NES-APEX2-GFP cells (experiment 4). For each approach, Applicant conducted biologically independent triplicate labeling reactions followed by mixing of lysates and streptavidin purification of biotinylated proteins. Affinity-purified samples and the corresponding input samples were analyzed by quantitative MS. In total, Applicant detected 1,416 proteins across all input samples and 2,020 proteins across all streptavidin enrichments (FIG. 8D), accounting for 64% (153) of a manually curated list of 238 annotated SG proteins (Table 1). Protein identification and quantification of heavy to light (H/L) ratios were highly reproducible across replicate experiments (FIG. 9). Applicant compared the enrichment of known SG proteins to the background distribution of all detected proteins (FIG. 1E and FIG. 2A). Known SG proteins were significantly enriched across all four approaches, with the greatest shift in logγ H/L ratios detected in experiments 2 and 3. Interestingly, Applicant observed attenuated enrichment of known SG proteins in experiment 1 and that even in the absence of stress (experiment 4), known SG proteins appeared to be enriched in the IP samples (FIG. 1E and FIG. 2A).

G3BP1-APEX2-Mediated Biotinylation Identifies SG Proteins with High Specificity

Applicant used a series of analysis steps to identify candidate SG proteins from our quantitative proteomics data (FIG. 8E). Applicant first leveraged our curated list of annotated SG proteins to determine logy H/L ratio cutoffs in a non-parametric approach similar to previous ratiometric SILAC APEX experiments (Hung et al., 2014). Applicant ranked identified proteins in each replicate by their logy H/L ratio and calculated the frequency distribution of known SG proteins across the ranked lists (FIG. 2A). Applicant chose as a conservative cutoff the ratio at which the frequency of known SG proteins in a moving window fell below 2-fold the frequency across all detected proteins. In parallel, Applicant applied an empirical Bayes method (Kammers et al., 2015) to identify proteins that were significantly enriched in heavy over light samples. This method is based on the linear models for microarray data (LIMMA) approach (Smyth, 2004), which is also applicable to quantitative proteomics data (Margolin et al., 2009). It uses the actual observed data to moderate individual protein variances through an estimated global sample variance, and thus enables a more robust identification of significant changes in protein abundance than ordinary t-statistics. The resulting moderated p values are corrected for multiple hypothesis testing using a modified Benjamini-Hochberg false discovery rate (FDR) approach to determine a moderated q-value (q.mod).

For the final list of SG candidates, Applicant initially selected all proteins that were above the ratio cutoff in at least 2 out of 3 IP replicates. Applicant defined a set of 123 proteins from the overlapping sets as shown in FIG. 2B (shaded in gray). Of these, 80% (99/123) are also statistically significantly enriched (q.mod <0.05) in at least one experiment. For most of the remaining 24 proteins, no significance values could be determined due to missing data in one of the biological replicates. However, as ~25% of these proteins were previously known SG proteins, Applicant chose to retain them in our final list (marked by # in FIG. 2B). Table 2 provides a detailed overview of all hit candidates across all four experimental designs.

Underscoring the robustness of the approach, many well-characterized SG proteins (e.g., G3BP1, TIA1, CAPRIN1, PABPC1, FMR1, and ATXN2) were identified as highly significant interactors across multiple experiments (FIG. 2C). In summary, nearly 80% (96/123) of hits are known SG proteins (69/123), were verified by IF (13/123), or have additional data supporting SG association, such as closely related family members or interactions with known SG proteins (14/100; e.g., HNRNPDL, YTHDF3). For example, the DEAD-box helicase ("DEAD" disclosed as SEQ ID NO: 29) DDX1 is known to localize to SGs and was shown to form an RNA transport complex with C14ORF166, FAM98A/B, and RTCB (Pérez-González et al., 2014), all of which Applicant identify as SG candidates (FIG. 2B and FIG. 2C). Interestingly, our SG protein set also contains ANXA11, its closest paralog ANXA7, and their interactor PEF1 (FIG. 2B and FIG. 2C). While none of these proteins had previously been implicated in SG biology, ANXA11 was recently shown to harbor ALS-associated mutations leading to abnormal protein aggregation (Smith et al., 2017). In summary, Applicant demonstrates that APEX proximity labeling can be applied to dynamic RBP granules to identify known and previously unknown SG proteins with relevance to neurodegenerative disease.

Proximity Labeling Reveals a Pre-existing Network of SG Protein Interactions

Visible SGs only coalesce in response to cellular stress; however, our data suggested an enrichment of SG proteins in the G3BP1 interactome even in unstressed cells. Indeed, Applicant found that less than half (48.8% [60/123]) of SG-APEX hits were stress-dependent interactors (FIG. 2B), including 11 (out of 12 detected) individual subunits of the EIF3 and EIF4 translation initiation factors, which are thought to accumulate in stalled pre-initiation complexes in SGs. Remarkably, 51.2% (63/123) of APEX hits, including many well-studied SG proteins (e.g., CAPRIN1, FMR1, TIA1, and USP10), interact with G3BP1 in the absence of stress (FIG. 2B and FIG. 2C).

To expand on these findings, Applicant also retrieved publicly available direct protein-protein interaction (PPI) data for all proteins either detected by SG-APEX in HEK293T cells or previously annotated as SG proteins. The resulting SG-PIN contains 283 nodes and 866 non-redundant edges (FIG. 2D) and is more densely connected than PINs built from an equal number of randomly selected nodes and edges (FIG. 2E). In combination with our SG-APEX data, this suggests a pre-existing steadystate network of protein interactions that likely facilitates the rapid coalescence of microscopically visible SGs upon exposure of cells to environmental stress.

Figures 3A, 3B, 3C, 3D, 3E, 3F, 3G, 3H:
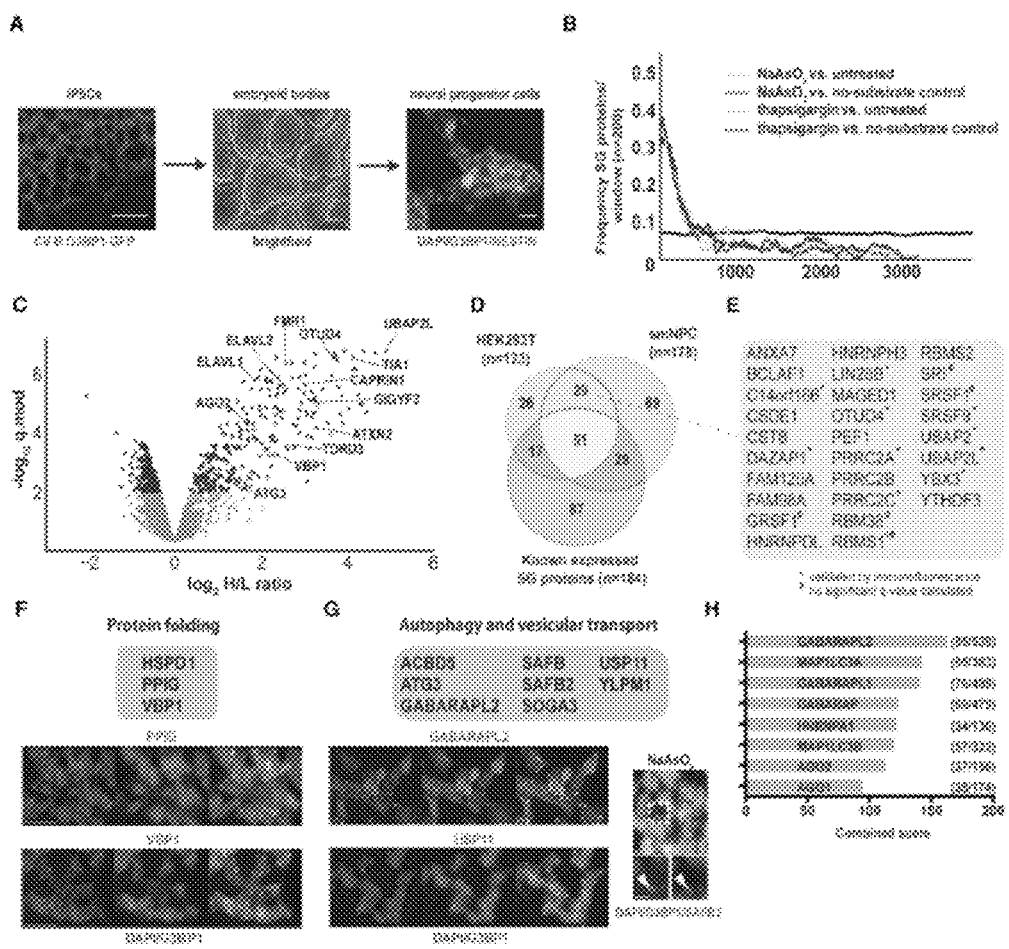
FIGS. 3A-3H: NPCs and HEK293T Cells Contain Distinct but Overlapping Sets of SG Proteins.
Figures 10A, 10B, 10C, 10D:
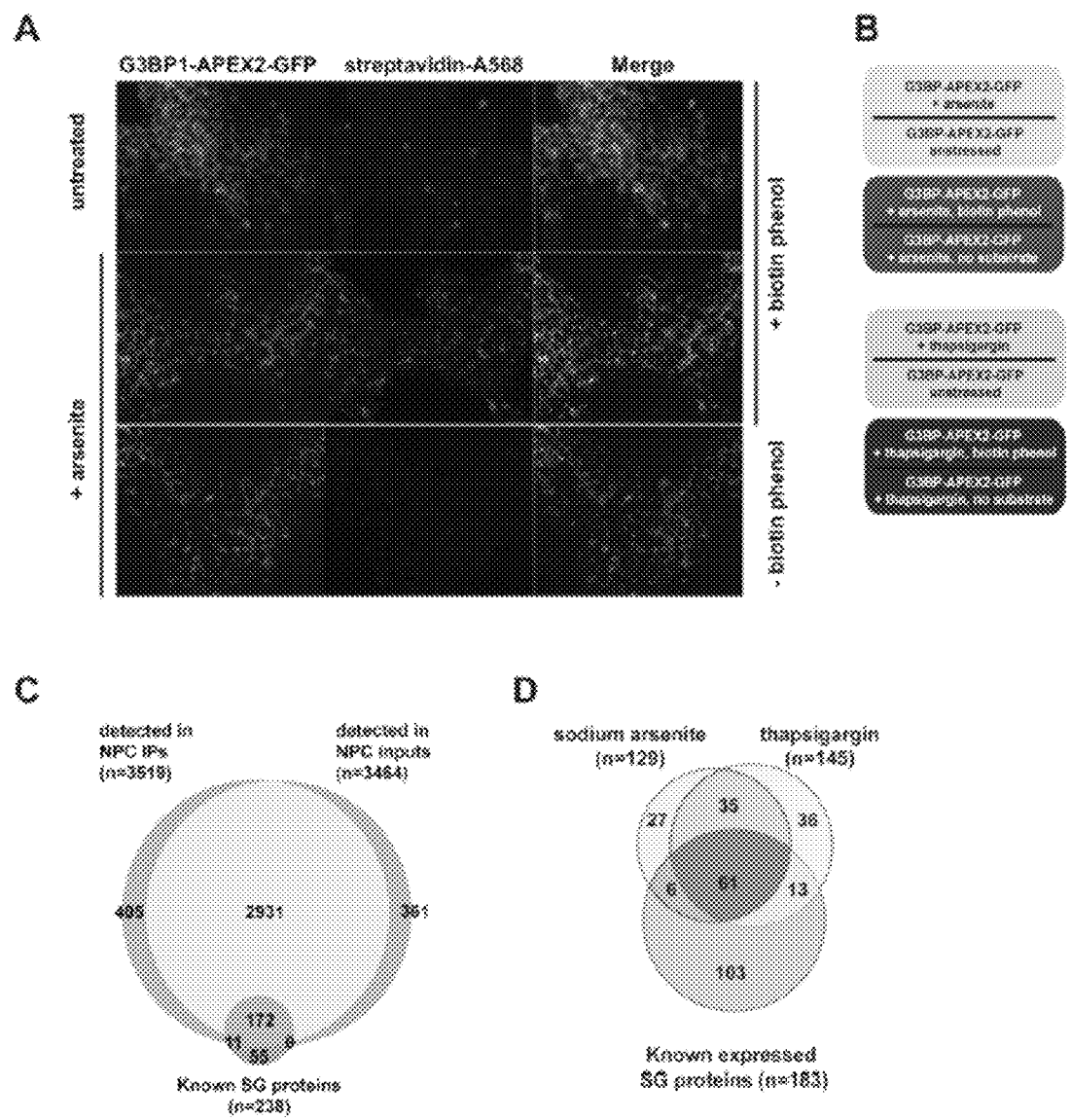
FIGS. 10A-10D: APEX-Mediated Biotinylation, Experimental Design, and Detected Proteins in Neural Progenitor Cells, Related to FIG. 3.

G3BP1-APEX2 Proximity Labeling in Human Neuronal Cells Reveals Cell-Type and Stress-Specific SG Proteins To enable analysis of SGs in more neurodegeneration-relevant cell types, Applicant used CRISPR/Cas9-mediated genome engineering to generate G3BP1-APEX2-GFP-expressing human induced pluripotent stem cells (iPSCs). Upon differentiation to neural progenitor cells (NPCs) (FIG. 3A), G3BP1-APEX2-GFP robustly localized to SGs upon NaAsO2 treatment and streptavidin staining overlapped well with the GFP signal (FIG. 10A). Applicant then used quantitative proteomics to compare $NaAsO_2$-treated and unstressed G3BP1-APEX2-GFP expressing NPCs, as well as $NaAsO_2$-treated G3BP1-APEX2-GFP cells with and without substrate (FIG. 10B). To compare the effects of different stressors, Applicant used thapsigargin in parallel experiments. In total, Applicant detected 3,880 proteins across all streptavidin enrichments and input samples that account for 77% (183/238) of known SG proteins (FIG. 10C). Analysis of logy H/L ratio distributions and enrichment of known SG proteins in the data gave similar results to those observed in HEK293T cells, with high enrichment of known SG proteins in all experiments (FIG. 3B, FIG. 3C). Using a similar analysis strategy as in HEK293T cells, Applicant designated 178 proteins from experiments with both stressors as candidate SG proteins in NPCs (FIG. 10D). Of these, 45.5% (81/178) are known SG proteins and another 21.3% (38/178) were either closely related to known SG proteins, also identified as SG candidates in HEK293T cells, or independently validated by IF (FIG. 3D and FIG. 3E). Interestingly, of the combined 221 SG-APEX hits from NPCs and HEK293T cells, 64% (141/221) were identified in only one cell type (FIG. 3D). Many of these proteins identified in only one cell type were not detected in sufficient experiments in the other cell line, likely due to incomplete capture of lowly expressed proteins and differences in protein abundance between cell types. Nevertheless, these findings suggested a potentially larger than anticipated cell-type-specific diversity of SG composition and called for further examination through complementary approaches.

Neuronal SG Proteins Function in Cellular Pathways Relevant to Neurodegeneration Applicant next wanted to evaluate whether the seemingly greater complexity of neuronal SG composition might contribute to rendering these cell types especially vulnerable to environmental stress and subsequent protein aggregation. As expected, several proteins with known neuronal expression and links to neurodegeneration (e.g., CELF2/3, ELAVL2/3/4, and GIGYF1/2) were among the neuronal SG proteins. In addition, Applicant validated the SG association of several previously unknown candidates involved in the regulation of protein folding (HSPD1, PPIG, and VBP1) (FIG. 3F). A second pillar of proteostasis is clearance of aggregates, and Applicant identified numerous factors that function in autophagy and related vesicular transport processes (FIG. 3G) among our neuronal SG proteins. Several of these (GABARAPL2, YLPM1, and SAFB2) cluster in the ULK-AMPK (AMP-activated protein kinase) subnetwork of the human autophagy system (Behrends et al., 2010), which also contains constitutive SG proteins (G3BP1, USP10, and CDC37) and may integrate aging and the cellular stress response (Salminen and Kaarniranta, 2012). The extent to which SG proteins are surveilled by autophagy factors is further highlighted by the finding that 5 of the 6 proteins with the highest connectivity to an extended list of SG candidates comprising all 361 APEX hits and previously known SG proteins are members of the ATG8 family of small ubiquitin-like modifiers (FIG. 3H). Indeed, ~16% of all GABARAPL2 (85/539) and 17% of all MAP1LC3A (65/383) interactions are with SG proteins, which together represent ~2.5% (361/14,352) of all proteins in the PPI dataset (FIG. 3H), suggesting that tight surveillance of SG proteins through interactions with ATG8 proteins may facilitate the important role of autophagy in SG clearance (Buchan et al., 2013).

Figures 4A, 4B, 4C, 4D, 4E, 4F, 4G:
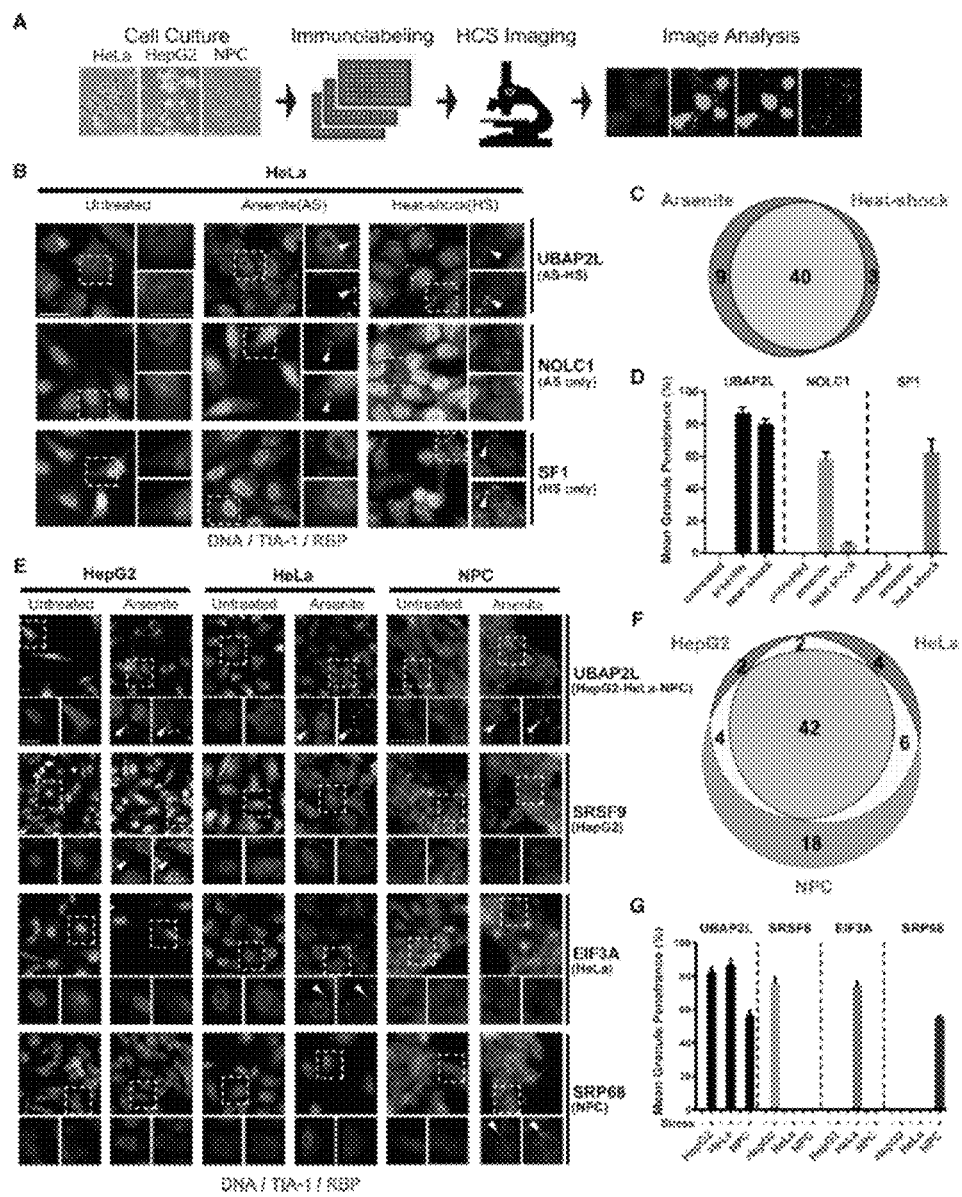
FIGS. 4A-4G: An RBP-Centered Imaging Screen Identifies Stress- and Cell-Type-Specific SG Components.

High-Throughput Imaging of RBPs Reveals Stress- and Cell-Type-Specific SG Composition As SG proteins are strongly enriched for RBPs, highly validated antibodies against >300 human RBPs (Sundararaman et al., 2016) were combined with a screening pipeline involving systematic IF labeling followed by high-content microscopy and image analysis (FIG. 4A) to further characterize the repertoire of SG-associated RBPs. SGs have been known to exhibit stress-dependent variability in composition (Aulas et al., 2017), but to our knowledge, the extent of this variability has not been comprehensively evaluated. To systematically determine the degree to which SG composition varies by stress type, Applicant exposed HeLa cells to either $NaAsO_2$ or heat shock (30 min at 42° C.) and performed a screen with our RBP antibody collection. Of the 313 RBP antibodies tested, 17% (52 RBPs) localized to SGs. Among these, 77% (40/52) localized to SGs under both stress conditions, while 23% (12/52) exhibited stress-type-specific SG targeting (FIGS. 4B-4D; Table 3). For example, UBAP2L robustly localized to SGs in both stress conditions, while SG-association of NOLC1 and SF1 was specific to $NaAsO_2$ or heat shock, respectively (FIGS. 4B and 4D). Applicant next conducted parallel screens in three different cell types (HepG2, HeLa, and NPCs) treated with $NaAsO_2$. Applicant identified a total of 77 SG-RBPs, with over half of these (42/77) localizing to SGs in all three cell types and the remaining 35/77 proteins exhibiting varying degrees of cell-type specificity (FIGS. 4E-4G; Table 4). For example, UBAP2L co-localized with SGs in all cell types, while SRSF9, EIF3A and SRP68 were selectively targeted to SGs in HepG2 cells, HeLa cells, or NPCs, respectively (FIGS. 4E and 4G). Notably, consistent with our APEX results, Applicant found that about one third (28/77) of SG-RBPs localized to SGs in NPCs but failed to do so in at least one of the other cell types tested. To summarize, 120 proteins were found to associate with SGs in NPCs but were absent from SGs in at least one other cell type. While these proteins may not be exclusive to SGs in neuronal cells, Applicant refers to them as neuronal SG proteins here because they show a neuronal preference due to either higher expression levels or cell-type-specific SG targeting. This systematic survey of cell-type-specific SG-RBPs further extends our SG compendium and shows that neuronal cells exhibit a greater diversity in SG composition than non-neuronal cells. The observation that 75% (90/120) of neuronal SG proteins had not previously been associated with SGs further highlights that past studies using common immortalized cell lines have missed potentially important neuronal SG proteins.

Figures 5A, 5B, 5C, 5D, 5E, 5F:
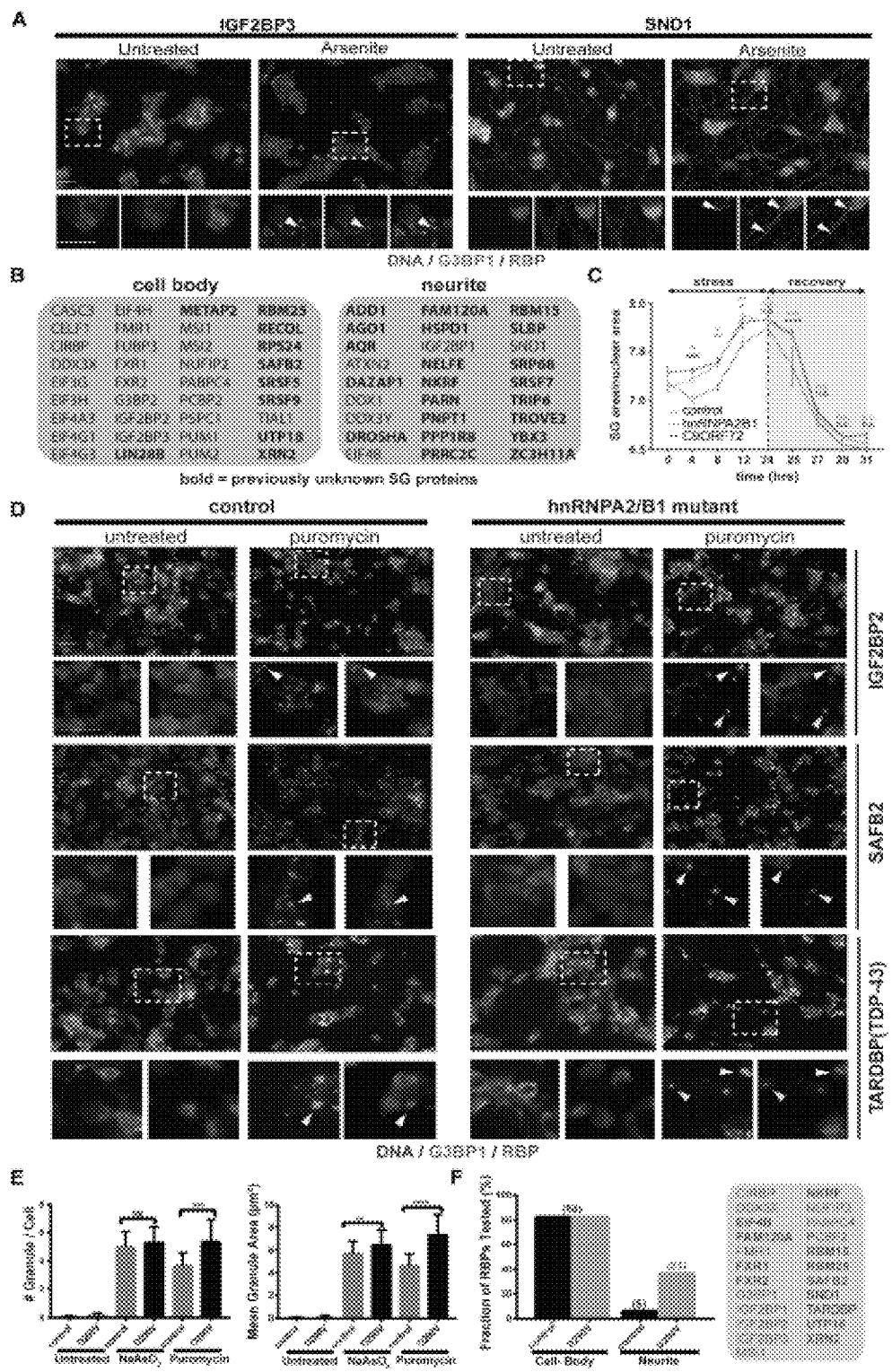
FIGS. 5A-5F: SG Composition and Subcellular Distribution Is Altered in ALS-Patient-Derived iPS-MNs.
Figures 11A, 11B, 11C:
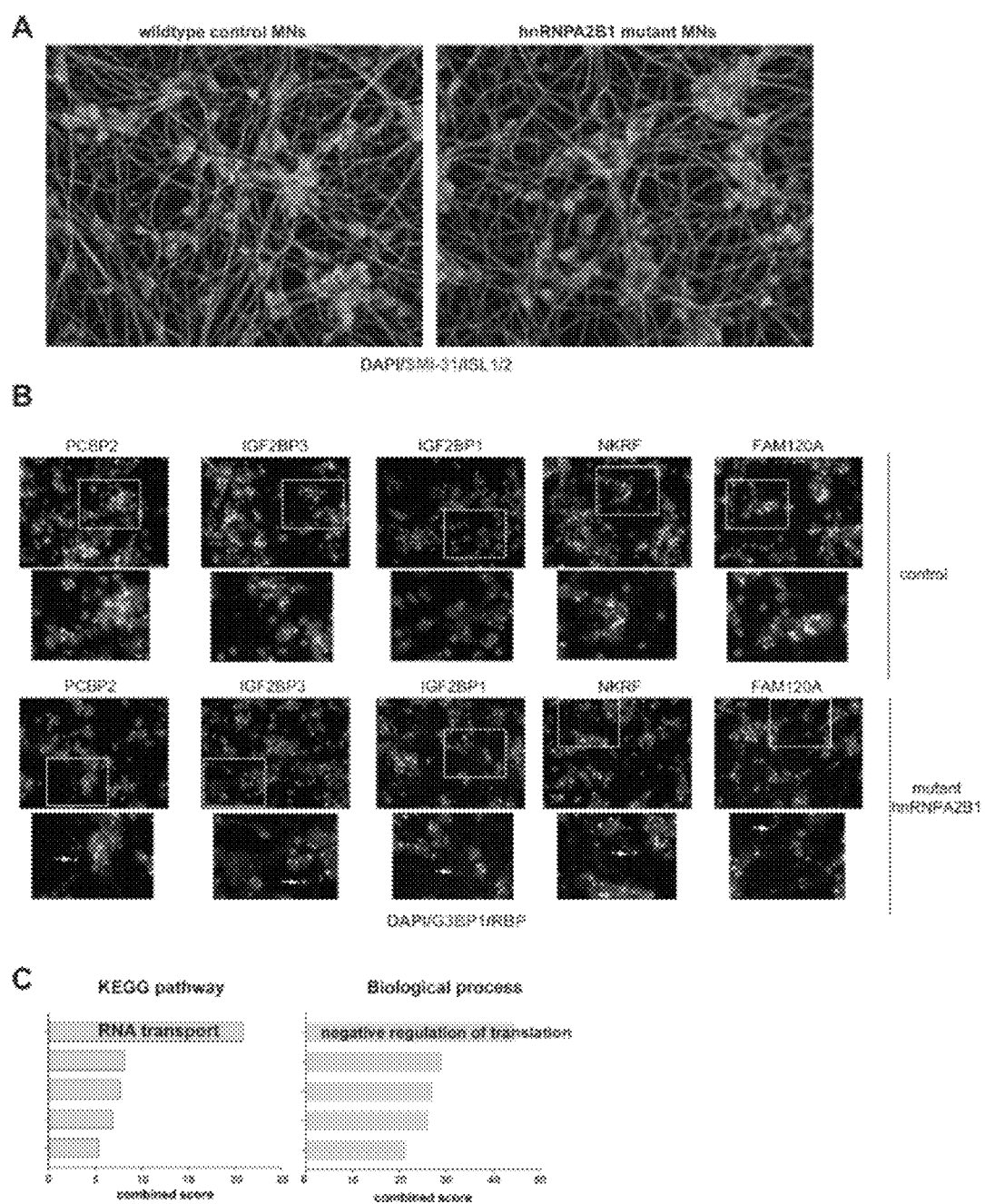
FIGS. 11A-11C: Expression of Cell-Type-Specific Markers and Neurite-Localized Granules in iPSC-Derived Motor Neurons, Related to FIG. 5.

SGs Vary in Composition and Subcellular Localization in iPSC-Derived Motor Neurons The components of SGs, as well as the molecular interactions that determine SG dynamics are increasingly implicated in human neurological disorders, including ALS. As motor neurons (MNs) are the most severely affected cell type in ALS, Applicant next characterized the SG-targeting behavior of RBPs in iPSC derived MNs (iPS-MNs; FIG. 11A). Applicant first carried out IF staining for 63 (of 77) SG-RBP hits in control iPS-MNs that were either untreated or treated with $NaAsO_2$ or puromycin, which robustly induces SGs in iPS-MNs after a 24-hr treatment without overt toxicity (Martinez et al., 2016). In unstressed iPS-MNs, 57% (36/63) of RBPs localized primarily to cell bodies (e.g., IGF2BP3; FIGS. 5A and 5B), whereas 43% (27/63) of RBPs also showed clear localization to projecting neurites (e.g., SND1; FIGS. 5A and 5B). Following stress treatments, Applicant identified 51 RBPs that co-localized with G3BP1-labeled SGs (Table 5), most of which (49/51) localized to SGs in both $NaAsO_2$ or puromycin treated cells, while two (DAZAP1, ZC3H11A) were selectively targeted in response to puromycin. Both SND1 and IGF2BP3 colocalized with G3BP1-labeled SGs in cell bodies, while SND1 was also present in granules along neurites (FIG. 5A). Applicant conclude that stress-induced granules of varying composition form in a subcellular compartment-specific manner in human iPS-MNs.

SG Composition and Subcellular Distribution Are Affected in iPSC Models of ALS

ALS-associated mutant versions of FUS, hnRNPA2/B1, and TIA1, as well as dipeptide repeats (DPRs) derived from an expanded GGGGCC ($G_4C_2$) repeat in C9orf72, were recently reported to affect rate and dynamics of SG formation (Boeynaems et al., 2017; Lee et al., 2016; Lin et al., 2016; Mackenzie et al., 2017; Martinez et al., 2016; Murakami et al., 2015; Patel et al., 2015). Expanding on our previous study using iPS-MNs carrying the ALS-associated D290V mutation in HNRNPA2B1 (Martinez et al., 2016), Applicant observed an increased rate of formation as well as impaired early clearance of puromycin-induced G3BP1-positive SGs in both HNRNPA2B1 and C9orf72 mutant iPS-MNs (FIG. 5C). Surprisingly, in addition to an increased propensity to form SGs (FIG. 5E), screening of HNRNPA2B1 mutant iPS-MNs with our SG-RBP antibodies also revealed mutation-specific differences in the subcellular distribution of SG-RBPs (FIGS. 5D and 5F). In control cells, most analyzed RBPs localize primarily to SGs in the cell body upon puromycin treatment. In contrast, almost half (23/50) of SG-RBPs also localized to prominent granules in neurites in HNRNPA2B1 mutant cells (such as IGF2BP1/2/3, SAFB2, PCBP2, NKRF, and FAM120A; shown in FIGS. 5D and 5F; FIG. 11B). Additionally, even for proteins that were found in neurite-localized granules in both control and mutant cells (such as the ALS-associated protein TDP-43), their localization to neurite-localized SGs appeared more pronounced in HNRNPA2B1 mutant cells (FIG. 5D). The RBPs found in neurite-localized SGs were enriched in functions such as RNA transport and translational suppression (FIG. 11C), which is consistent with and extends previous studies reporting that axonal transport is impaired in ALS motor neurons (Alami et al., 2014; Yasuda and Mili, 2016). Altogether, our findings confirm aberrant SG dynamics across ALS-associated mutations and highlight abnormal SG distribution and composition in the projections of HNRNPA2B1 mutant iPS-MNs, which provide further insights into ALS pathogenesis.

Cross-Comparison with Related Datasets Identifies Disease Relevant SG Proteins

Figures 6A, 6B, 6C, 6D, 6E, 6F, 6G:
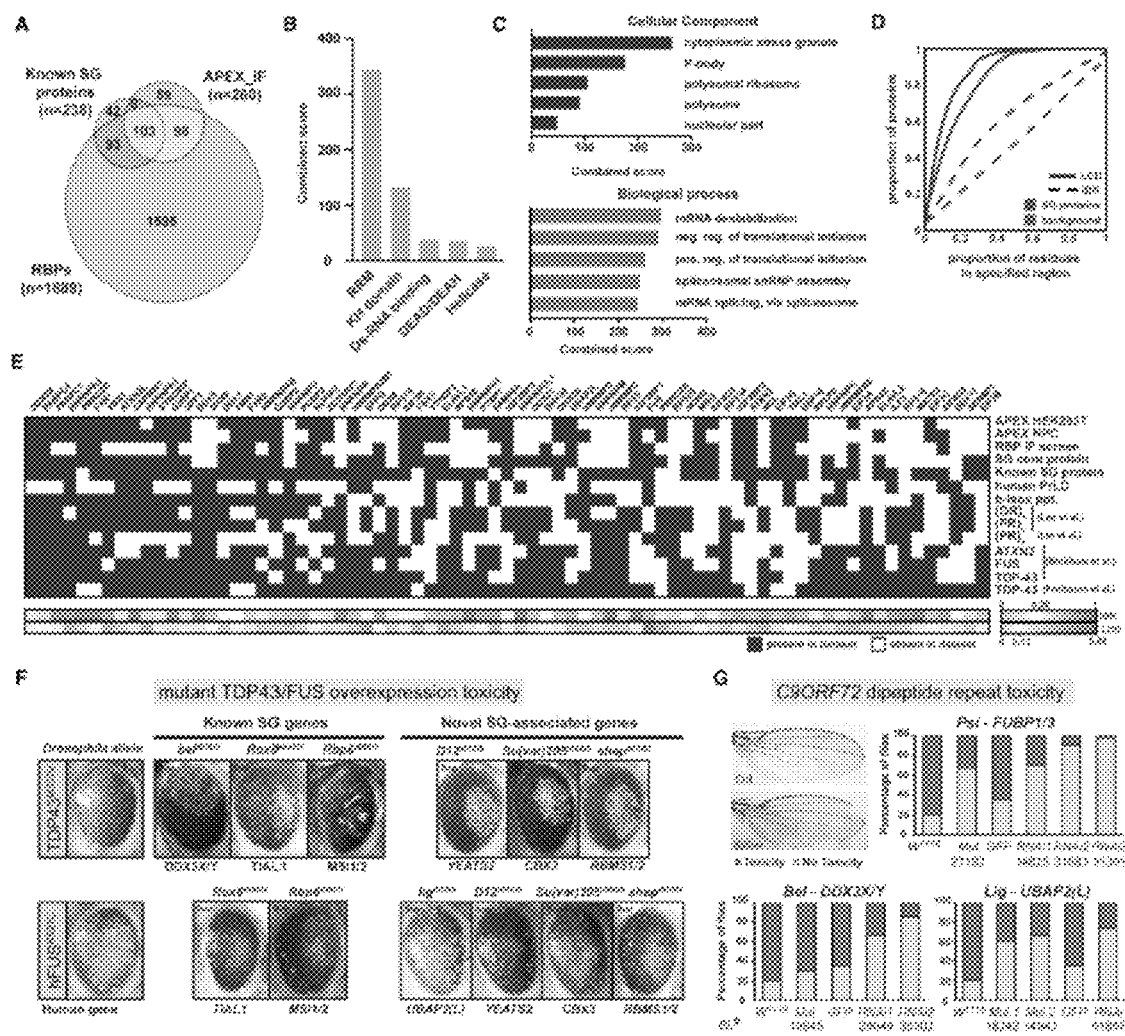
FIGS. 6A-6I: Integrative Data Analysis Highlights Potential Disease-Relevant Proteins.

Together, our APEX and IF screening approaches identified 260 SG proteins, including ~150 candidates that had not previously been associated with SGs. Consistent with known SG proteins, our hits are enriched for RBPs (201/260 [77.3%]; FIG. 6A) with a range of RNA-binding domains (FIG. 6B) and gene ontology (GO) terms associated with RNA metabolism and translational control (FIG. 6C). They also contain a significantly higher proportion of amino acid residues in IDRs and LCDs (FIG. 6D) than the background proteome, consistent with LLPS being a driver of SG assembly. To place in context how individual SG proteins might be connected to disease, Applicant integrated our SG compendium with 11 published datasets related to protein aggregation in neurodegeneration (FIG. 6E) (Blokhuis et al., 2016; Freibaum et al., 2010; Jain et al., 2016; Kato et al., 2012; Lee et al., 2016; Lin et al., 2016; March et al., 2016). While these diverse datasets are not expected to overlap completely, their cross-comparison can nevertheless be useful for situating each individual study into a greater context. Furthermore, ranking the proteins by how frequently they occur across all datasets can help identify features of the most consistently observed proteins and prioritize candidate genes for follow-up studies.

Of the 1,312 proteins found across the 14 datasets, almost two thirds (840/1,312) were present in only a single dataset (FIG. 12B) and only 5% (71/1,312) were found in at least half of the datasets. Remarkably, all of these 71 proteins and indeed 96% (192/200) of the top 200 proteins are RBPs, many with higher proportions of LCDs and IDRs (FIG. 6E) than the background proteome. Many well-studied SG proteins with roles in neurodegeneration (e.g., FUS, ATXN2, and FMR1) are broadly represented, as are several less well-characterized and previously unknown SG proteins that warrant further investigation.

SG Components Modify Disease Protein Toxicity in Drosophila ALS/FTD Models

Figures 12A, 12B, 12C, 12D, 12E:
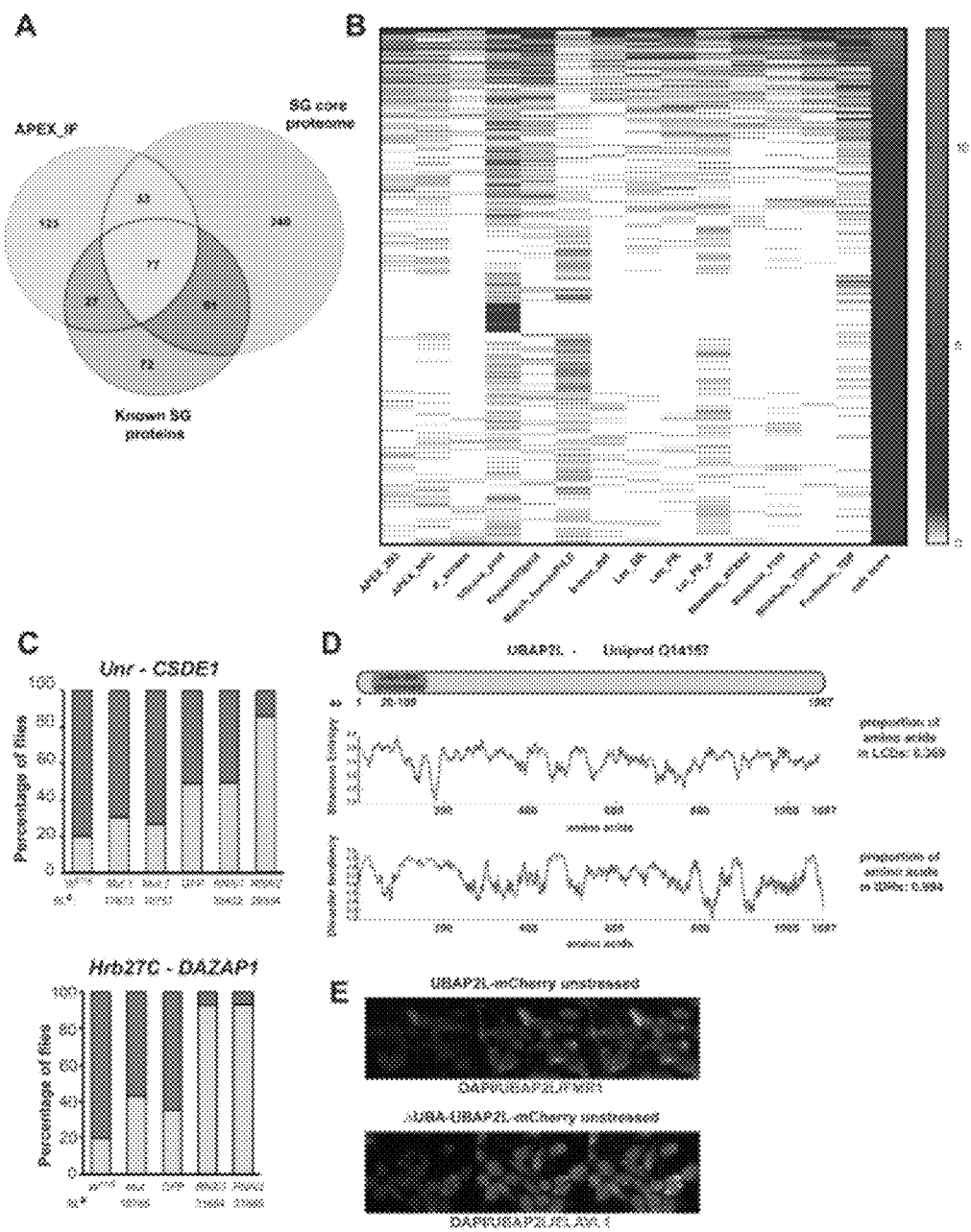
FIGS. 12A-12E: Extended Dataset Cross-Comparison, Additional Fly Modifiers, UBAP2L Protein Structure and Co-localization with Stress Granule Proteins, Related to FIG. 6.

To further confirm the disease-relevance of known and previously unidentified SG proteins in vivo, Applicant used several Drosophila models of ALS/FTD to examine disease protein toxicity in both neuronal and non-neuronal cells. Mis-expression of ALS-linked mutated hTDP-43$^{M337V}$ or hFUS$^{R521C}$, respectively, causes a neurodegenerative rough eye phenotype (unpublished data; Lanson et al., 2011; Ritson et al., 2010). Applicant recently carried out a genome-wide screen for genetic modifiers of TDP-43 and FUS toxicity (unpublished data), which Applicant intersected with our SG protein data. Not unexpectedly, Applicant identified several SG-RBPs as modifiers of TDP-43 and FUS-mediated toxicity (FIG. 6F). In addition to the TDP-43 and FUS models, Applicant performed genetic interaction studies to test several selected SG proteins for their ability to modify toxicity caused by overexpression of a C9orf72-ALS/FTD associated poly(GR) in the Drosophila wing (Yang et al., 2015). Applicant tested 9 candidate genes, either by multiple RNAi knockdown or through genetic mutant alleles, and found that partial loss of activity for more than half (5/9) significantly rescued poly (GR) toxicity (FIG. 6G; FIG. 12C). Although the detailed mechanisms underlying these genetic interactions remain to be further investigated, our Drosophila results identify several previously unknown SG proteins, such as CBX3, CSDE1, RBMS1/2, UBAP2(L), and YEATS2, as potentially disease-relevant factors (FIG. 6F and FIG. 6G), underscoring again that alterations in SG components can affect neurodegenerative phenotypes.

Figures 6H, 6I:
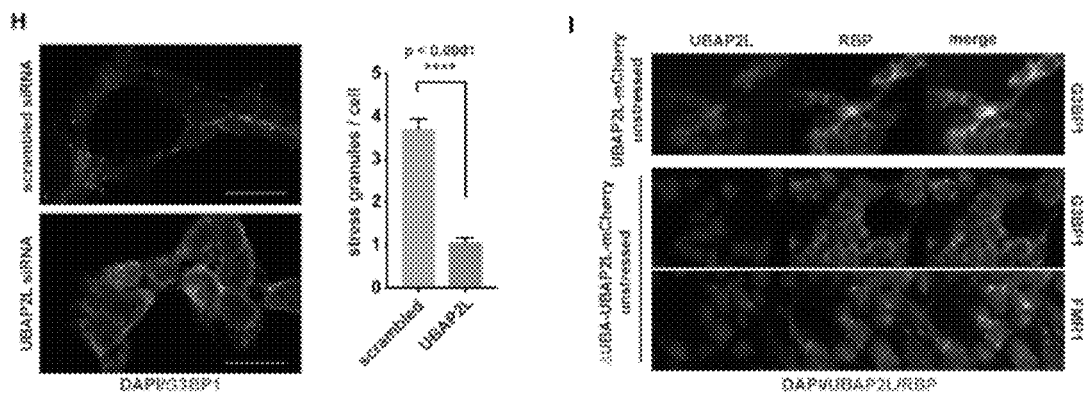

Applicant selected one of these previously unknown SG-associated disease-modifiers, UBAP2L, for evaluation in human cells, as it was consistently among the most robustly SG-associated proteins by both SG-APEX and IF across all cell types and stress conditions tested (FIGS. 4B and 4E). Applicant found that depletion of UBAP2L by small interfering RNA (siRNA) in HeLa cells almost completely abolished NaAsO$_2$-induced SG formation (FIG. 6H), establishing UBAP2L as an essential regulator of SG assembly. It is among the most disordered proteins in the human proteome, with 99.4% of its 1,087 amino acids considered to fall within IDRs (FIG. 12D), suggesting a potential for UBAP2L to undergo LLPS. Interestingly, while inducible expression of an UBAP2L-mCherry fusion protein recapitulated endogenous UBAP2L localization, a truncated version lacking the N-terminal ubiquitin-associated UBA domain (ΔUBA_UBAP2L-mCherry) led to widespread formation of aggregates containing the SG proteins G3BP1, FMR1, and ELAVL1 even in the absence of stress (FIG. 6I; FIG. 12E). Applicant's findings reveal UBAP2L as an excellent future candidate to study how protein aggregation might be regulated both in the absence or presence of cellular stress.

Discussion

In this study, Applicant extend the application of in vivo APEX proximity labeling combined with quantitative proteomics to the study of highly dynamic, non-membranous RBP granules. In combination with an RBP-focused IF screen, Applicant identify ~150 proteins not previously known to associate with SGs. Applicant estimate that up to 20% of components may be recruited to SGs in a cell-type or stress-type-specific manner. Interestingly, neuronal cells appear to contain compositionally more diverse SGs, and many of the components have reported functions in PQC pathways such as chaperone-assisted protein folding and aggregate clearance by autophagy. Defects in PQC have been implicated in the development of neurodegeneration (Ciechanover and Kwon, 2017), and our observation might help explain why neuronal cells are especially dependent on accurate regulation of protein homeostasis. Applicant implemented the SG-APEX approach by tagging the endogenous G3BP1 locus in iPSCs, which not only minimizes potential artifacts from G3BP-APEX2-GFP overexpression but also opens the possibility of studying SGs in a wide range of differentiated cell types from a constant genetic background. Future studies using a combination of different APEX2-tagged proteins can make it possible to further dissect the molecular architecture of RBPs and enable the distinction of closely related subtypes of RBP granules such as P-bodies, as well as the characterization of cell-type-specific granules such as neuronal transport granules.

Figures 7A, 7B, 7C:
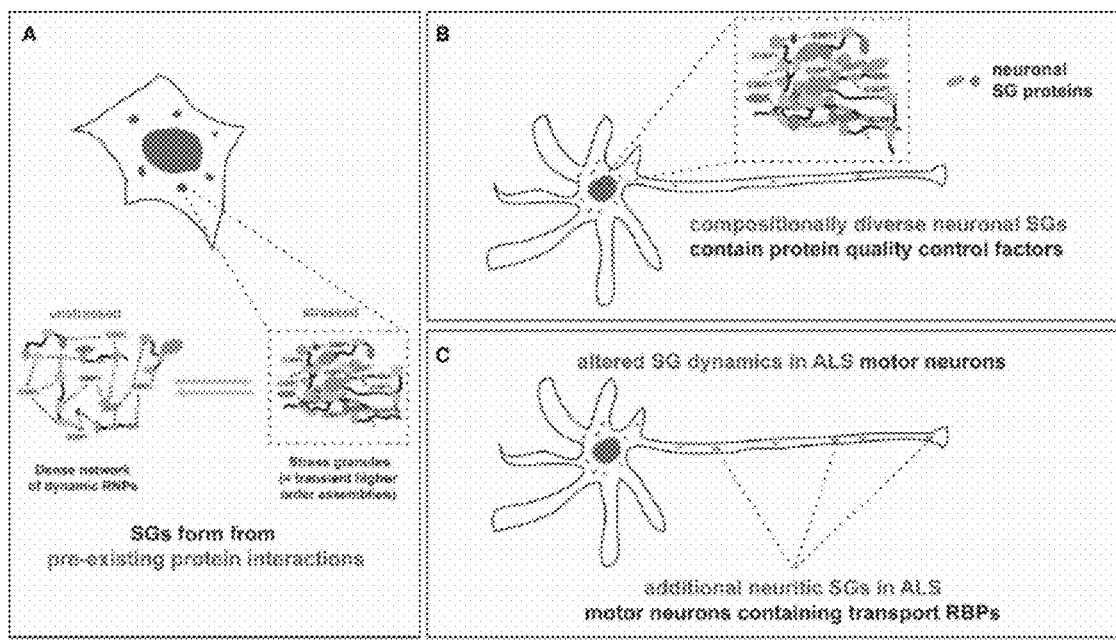
FIGS. 7A-7C: SG Form from Pre-existing PPIs Are Especially Diverse in Neuronal Cells and Display Aberrant Characteristics in ALS Mutant Cells.

In addition to providing a resource of nearly 150 previously unknown candidate SG proteins for further validation, this study links many known and previously unidentified SG proteins to human disease and provides unexpected and exciting insights into SG biology and how it relates to neurodegeneration (FIG. 7). First, our SG-APEX data in stressed and unstressed cells, combined with independent PPI data, show that much of the underlying network of SG protein interactions already exists in unstressed cells. This finding sharpens the picture of a highly evolved and dense network of RBPs that integrates the many steps of gene expression regulation. As a result, although SGs appear to form de novo in response to stress, their emergence represents a moderate and transient shift in a tightly controlled equilibrium of protein-protein and protein-RNA interactions (FIG. 7A). Allocating high local concentrations of processing factors and substrates into interconnected RBP assemblies enables highly efficient processing to take place but at the same time increases the risk of uncontrolled protein aggregation. As a result, cells have evolved mechanisms for efficiently resolving transient higher-order RBP assemblies, especially in the context of a temporary stress response. Our results highlight how SG proteins are tightly integrated with PQC pathways, most strikingly through close surveillance by the ATG8 family of autophagy mediators. Interestingly, neuronal cells display a greater diversity in SG composition compared to non-neuronal cells, and numerous PQC factors localize specifically to neuronal SGs, potentially providing an explanation to why neurons are especially vulnerable to environmental stresses (FIG. 7B). Lastly, Applicant demonstrate that iPS-MNs harboring ALS-associated mutations in HNRNPA2B1 form SGs more readily and that mutant cells are more prone to forming SGs along neuronal projections, which differ in their composition from SGs found in the soma (FIG. 7C). These neurite-localized SGs are enriched in proteins involved in RNA transport and translational repression, suggesting a mechanism by which genetic mutations could interact with environmental factors to widely impair axonal transport and contribute to axon degeneration in ALS.

Much attention is currently being focused on understanding how exactly the known ALS-linked mutations in multifunctional RBPs alter the structure and function of these proteins to result in aberrant protein aggregation. However, as emphasized by the late onset and cell-type specificity of disease symptoms, these genetic factors only result in pathology once other components of the regulatory system that normally prevent long-lived RBP aggregation begin to fail. Future work should focus on identifying the critical factors and mechanisms in this system. The SG protein compendium Applicant present here suggests possible future directions and provides a framework for identifying previously unknown important regulators. Applicant present the example of UBAP2L, which is not only essential for SG formation but also can seed spontaneous protein aggregates when the ubiquitin associated region of the protein is removed. It is likely that modulation of UBAP2L levels can have a similar effect as reduction of ATXN2, which was recently shown to ameliorate TDP-43 toxicity in mice (Becker et al., 2017). Beyond UBAP2L, many poorly characterized proteins with potential relevance to aggregation can be identified and prioritized from our cross-comparison of more than a dozen SG and neurodegeneration-associated PPI datasets, combined with the added biological context of whether a specific RBP localizes to aberrant SG in ALS mutant iPS-MNs or can modify neurodegenerative phenotypes in flies.

In summary, it is critical to recognize that broad inhibition of the PPIs that underlie SG formation will also affect the dense RBP network in unstressed cells. Promising therapeutic strategies will therefore likely need to specifically target those mechanisms that only result in aberrant insoluble protein inclusions. This work represents a step along this path, which so far has been hindered by a sparsity of promising targets as well as a lack of robust disease-associated phenotypes in living cells.

Experimental Model and Subject Details

Immortalized human cell lines and human pluripotent stem cells (hiPSCs) were utilized in this study. The Lenti-X HEK293T cell line is derived from human female tissue, the HepG2 cell line is derived from human male hepatocellular carcinoma tissue and HeLa S3 cells are derived from human female cervical adenocarcinoma tissue. HEK293T and HeLa cells were maintained in DMEM and HepG2 cells in Hyclone growth medium both supplemented with 10% fetal bovine serum and 1% penicillin/streptomycin at 37° C. in a humidified incubator under 5% $CO_2$. hiPSCs were maintained under feeder-free conditions in mTeSR1 medium (Stem Cell Technologies) and propagated either by single-cell passaging using Accutase or clump-passaging using enzyme-free dissociation buffer (EDTA). Flies were reared on standard yeast-agar-cornmeal medium and crosses were performed at 25° C. The degenerative eye phenotype was assessed two weeks after the crosses were performed, while the wing margin notching phenotype was scored in 3-5 days old adult flies of the F1 generation.

Generation and Maintenance of Neural Progenitor Cells

Small molecule neural progenitor cells (smNPCs) were grown in medium consisting of DMEM/F12+Glutamax, 1:200 N2 supplement, 1:100 B27 supplement, penicillin/streptomycin (Life technologies), 100 µM ascorbic acid (Sigma, A4544), 3 µM CHIR99021 (CHIR, Tocris 4423) and 0.5 mM Purmorphamine (PMA) (Tocris 4551 and passaged using Accutase. Generation of smNPCs from iPSCs was adapted from (Reinhardt et al., 2013). Briefly, human iPSCs at 70%-80% confluency were dissociated using accutase and resuspended at $1\times10^{6}$ cells/ml in N2B27 medium (DMEM/F12+Glutamax, 1:200 N2 supplement, 1:100 B27 supplement, 150 µM ascorbic acid and 1% Penicillin/Streptomycin) supplemented with 1 µM Dorsomorphin, 10 µM SB431542, 3 µM CHIR99021, 0.5 µM Purmorphamine (PMA) and 5 µM Rock inhibitor (Y-26732). 3 million cells were transferred into one well of an uncoated 6-well tissue culture plate and incubated at 37° C., 5% CO2 on a shaker at 90 rpm. Uniform small EBs formed within 24 h and increased in size over the following days. After 48 h a full media change was performed with N2B27 medium supplemented with D, SB, CHIR and PMA. At this time, about 2/3 of EBs were either discarded or EBs were split across 3 wells of a 6-well plate to reduce the high cell density required initially to ensure uniform formation of embryoid bodies. On days 3-5, half medium changes were performed with fresh N2B27+D, SB, CHIR and PMA. On day 6, dorsomorphin and SB were withdrawn and a full medium change with smNPC medium (N2B27+3 µM CHIR+0.5mM PMA) was performed. At this stage, neuroepithelial folds were clearly visible in all EBs. On day 8, EBs were triturated by pipetting 10-15 times with a P1000 pipette and plated onto matrigel-coated 6-well or 10 cm plates (~1 well of a 6-well plate per 10 cm plate). After 3-4 days, attached EB fragments and outgrown cells were dissociated to single cells with accutase and split at a 1:6 to 1:8 ratio onto matrigel. After the first passage, cells were passaged at a 1:10 to 1:15 ratio every 3-6 days. For the first few passages, large flat non-smNPCs could be observed between smNPC colonies, but progressively disappeared no later than passages 3-6 in almost all cell lines.

Generation of iPSC-Derived Motor Neurons

Motor neurons were differentiated from iPSCs as described in (Martinez et al., 2016). Briefly, human iPSCs were grown plated into matrigel-coated 6-well plates or 10 cm culture dishes to reach 70%-90% conflency in mTeSR1 medium within 2-3 days. On day 1 of the differentiation protocol, medium was changed to N2B27 medium (DMEM/F12+Glutamax, 1:200 N2 supplement, 1:100 B27 supplement, 150 µM ascorbic acid and 1% Penicillin/Streptomycin) supplemented with 1 µM Dorsomorphin, 10 µM SB431542, 3 µM CHIR99021. Cells were maintained with daily medium changes in the same medium for 6 days. On day 7, medium was changed to N2B27 medium (DMEM/F12+Glutamax, 1:200 N2 supplement, 1:100 B27 supplement, 150 µM ascorbic acid and 1% Penicillin/Streptomycin) supplemented with 1 µM Dorsomorphin, 10 µM SB431542, 200 nM Smoothened Agonist (SAG) and 1.5 uM retinoic acid (RA). Medium was changed daily with increasing volumes to adjust for cell density until day 18. At day 18 of differentiation, cells were dissociated using Accutase and either plated directly for continued differentiation or optionally expanded in motor neuron progenitor (MNP) medium as described in (Du et al., 2015). Optionally, after dissociation, cells were plated onto matrigel-coated 10 cm plates at a density of 3-5 million cells per plate into N2B27 medium supplemented with 3 µM CHIR99021, 2 µM DMH1, 2 µM SB431542, 0.1 µM RA, 0.5 µM Purmorphamine and 0.5 mM valproic acid (VPA). Cells were maintained for no more than 5 passages under these conditions with weekly splitting using Accutase at 1:8-1:12 before final differentiation. For continued differentiation, cells were plated at a density of ~10 million cells per plate into 10 cm plates plate serially coated with 0.001% (=0.01mg/ml) poly-D-lysine (PDL, Sigma, P6407) and poly-L-ornithine (PLO, Sigma, P3655) followed by 20 ug/ml laminin (Life technologies, 23017015). Cells were plated into N2B27 medium supplemented with 200 nM SAG and 1.5 uM RA and 10 uM rock inhibitor. Medium was changed on day 20 and cells transferred into N2B27 medium supplemented with 2 uM DAPT on day 22. For imaging, cells were dissociated again at day 23 and plated into PDL/PLO/laminin-coated 96-well plates. Medium as changed into N2B27 medium without additional small molecules on day 25 and cells were maintained with medium changes every 2-3 days thereafter. Cells were stressed and fixed between days 29-32 of differentiation.

Plasmid Construction

To generate the donor vectors used to tag the endogenous G3BP1 locus in human cells, Applicant modified the HR120PA-1 targeting vector (System Biosciences (SBI)) by replacing GFP with an APEX2-(GGGGS)$_2$-GFP fusion protein ("(GGGGS)$_2$" disclosed as SEQ ID NO: 30). ~1.5 kb arms of homology were amplified from genomic DNA using primers that introduced ~35 bp overhangs with the targeting vector template on each end. The final G3BP1-targeting vector was assembled by Gibson assembly. G3BP1-APEX2-GFP was co-transfected with Cas9 expression vector px458 (gift from Feng Zhang, Addgene plasmid #48138) into HEK293T cells using lipofectamine 2000 or electroporated into CV-B iPS cells using an Amaxa Nucleofector with Stem Cell Kit 1 and pulse setting B-016. 48-72h post-transfection, puromycin was added to the medium at 1 ug/ml and cells kept in selective medium for 2-4 days. After 10-14 days, homogeneously green fluorescent single-cell derived colonies were manually picked under a stereomicroscope, expanded and tested for APEX2 activity.

For UBAP2L overexpression experiments, full-length and ΔUBA-UBAP2L-mCherry fusion constructs were cloned into pLIX_403 (gift from David Root, Addgene plasmid #41395) and packaged into lentiviral particles. MNPs were transduced and selected with 2 µg/ml puromycin (Life technologies, A1113803) for 7 days starting 2 days post-transduction. Expression was induced by adding 100 ng/ml doxyxycline for 24 h. To induce SG formation, cells were treated with 250 µM (NPCs, MNs) or 500 µM (HEK293T, HeLa, HepG2 cells) NaAsO$_2$ for 30 min (HeLa cells) or 1 h (NPCs, MNs, HEK293T and HepG2 cells). Alternatively, SG formation was induced by treatment with 10 ug/ml puromycin for 24 h (MNs), 500 nM thapsigargin (NPCs) or by heat shock for 30 min at 45° C. (HeLa, HepG2 cells).

SILAC Labeling with Isotopically Modified Amino Acids

For SILAC experiments, DMEM without L-arginine and L-lysine (Pierce catalog no. PI88420) was supplemented with 10% dialyzed FBS (Pierce, PI88440), penicillin/streptomycin, and 0.4 mM and 0.8 mM, respectively, of either unlabeled L-Lysine:HCL and L-Arginine:HCl (Sigma, cat no. L8662 and A6969) or isotopically labeled L-Lysine: 2HCl ($^{13}C_6$, $^{15}N_2$) and L-Arginine:HCl ($^{13}C_6$, $^{15}N_4$) (Cambridge Isotope laboratories, cat no. CNLM-291 and CNLM-539). Both heavy and light medium were additionally supplemented with 200 mg/ml L-Proline (Sigma, cat no. P5607).

For SILAC labeling of smNPCs, DMEM/F12 without L-arginine and L-lysine (Pierce catalog no. PI88215) was used instead of regular DMEM/F12 and supplemented with 0.7 mM and 0.5 mM, respectively, of either unlabeled L-Lysine:HCL and L-Arginine:HCl (Sigma, cat no. L8662 and A6969) or isotopically labeled L-Lysine: 2HCl ($^{13}C_6$, $^{15}N_2$) and L-Arginine:HCl ($^{13}C_6$, $^{15}N_4$) (Cambridge Isotope laboratories, cat no. CNLM-291 and CNLM-539).

APEX-Mediated Biotinylation

HEK293Ts and NPCs were grown in heavy or light SILAC medium for at least 5 passages prior to APEX labeling and isotope label incorporation efficiency was confirmed to be above 98%. Cells were seeded in 10 cm culture dishes one day prior to labeling to be ~80% confluent the following day and either left unstressed or treated with either 250 µM (NPCs) or 500 µM (HEK293T) NaAsO$_2$ or 500 nM thapsigargin for 1 h at 37° C. 500 µM biotin-phenol (BP) was added to the medium at the same time as stressors except for the no-substrate control samples. APEX labeling was performed by adding hydrogen peroxide to a final concentration of 1mM for 60 s before quenching the biotinylation reaction by adding Trolox ((+/−)-6-Hydroxy-2,5,7, 8-tetramethylchromane-2-carboxylic acid, Sigma 238813) and sodium L-ascorbate (Sigma A4034) to a final concentration of 5 and 10 mM, respectively. Samples were washed once with cold PBS, collected using cell scrapers, pelleted for 3 min at 300 g and immediately suspended in cold lysis buffer (8M urea, 150 mM NaCl, 20 mM Tris-HCl pH 8.0, Protease Inhibitor Cocktail Set III, EDTA-Free (EMD Millipore, cat no. 539134), 5 mM Trolox and 10 mM sodium L-ascorbate). Samples were sonicated and cleared by centrifugation at 12000 rpm for 10 min at 4° C. Protein concentration was determined using by 660 nm protein assay (Pierce, PI22660) and equal amounts of protein from corresponding light and heavy labeled samples were mixed for a total of 2-4 mg of protein. Samples were diluted to 2M urea by adding 3 volumes of 150 mM NaCl, 20 mM TrisHCl pH 8.0 with protease inhibitors and quenchers. For affinity purification, ~100 ul of streptavidin magnetic beads (Pierce, PI88817) were washed once in 2M urea buffer, resuspended directly in the sample, incubated for 2 h at room temperature and washed 8 times in 2M urea buffer. Following the washes, beads were centrifuged at 240 RCF for 5 min at 4° C. The supernatant was removed and a volume of 50 mM Ammonium bicarbonate buffer equal to the volume of the beads was added. For the on-bead digestion of the IP samples, the ammonium bicarbonate buffer was removed and replaced with an equal volume of 20 mM Tris pH8.0 with endoproteinase Lys-C (Wako) at a 1:100 (w/w) enzyme substrate ratio. Samples were incubated for 1 hr at 37° C. Following the Lys-C digestion, $CaCl_2$ was added to a final concentration of 1 mM along with 500 ng sequencing grade trypsin (Promega). The corresponding input samples for each IP were diluted to a final urea concentration of 1M using 50 mM Ammonium bicarbonate. Lys-C digestion was done as described above for the IP samples followed by trypsin digestion with a 1:100 (enzyme: protein) ratio. After trypsin addition, all samples were incubated at 37° C. for overnight with agitation. After the digestion, an equal volume of 5% formic acid was added to the digestion mixture and incubated at room temperature for 10 minutes. The supernatant was transferred to a new 1.5 mL tube and the elution step was repeated one more time. The trypsin-digested input and IP samples were concentrated and desalted using the Stage-Tip method and reconstituted in a 5% Formic acid/5% acetonitrile for MS analysis.

IF, Imaging and Image Analysis

Cells were fixed for 20 min in 4% formaldehyde, 1× PBS, followed by permeabilization for 10 min with 0.5% Triton, 1× PBS. Cells were rinsed with 1× PBS and blocked with blocking buffer (1× PBS, 2% BSA, 0.02% Triton). Cells were incubated with the primary antibodies against SG marker like TIA1 (TIA1, dilution 1:100, cat.# sc-1751, Santacruz) and antibodies against RBPs Sundararaman et al., 2016) diluted in blocking buffer for 2 hour at room temperature or overnight at 4° C. Then, the cells were thoroughly washed with 1× PBS, 0.2% Tween 20, and incubated for 2 hour with secondary antibodies (Alexa Fluor 647, cat. #A21447, Alexa Fluor 594, cat. #A21207, Life technologies and Alexa Fluor 488, cat. #111-546-144, JacksonImmuno, dilution 1:500) diluted in blocking buffer. Cells were washed, incubated for 5 min with DAPI and washed again. Cells were stored in the dark at 4° C. in 1× PBS or 50% glycerol/PBS for long-term storage. All images were taken using high content screen microscopy, ImageXpress Micro.

Drosophila Genetics

Flies were reared on standard yeast-agar-cornmeal medium and crosses were performed at 25° C. Drosophila transgenic strains carrying GAL4 inducible human ALS disease causing alleles of FUS/TLS and TDP-43 were previously described (Lanson et al., 2011; Ritson et al., 2010). Standard genetic procedures were used to generate the GMR-GAL4/CyO, tub-GAL80; UAS-FUS-hR521C/TM6B, Tb and GMR-GAL4, UAS-TDP-43-hM337V/CyO, tub-GAL80 transgenic strains (Periz et al., 2015). Drosophila strains containing the Exelixis insertional disruptions are publically available from the Department of Cell Biology, Harvard Medical School include $Rox8^{e04432}$, $Rbp6^{d08411}$, $lig^{f03269}$, $CG2889^{d07154}$, $D12^{e01238}$, $Su(var)205^{c06825}$ and $shep^{d07053}$. The dominant effect of the introduction of these inserts on degenerative eye phenotypes of GMR-GAL4; UAS-FUS-hR521C and GMR-GAL4, UAS-TDP-43-hM337V was assessed two weeks after the crosses were performed. Qualitative changes in pigmentation, ommatidial structure and glossiness phenotypes were monitored for enhancement or suppression.

UAS-$(GR)_{80}$ transgenic fly lines were generated previously (Yang et al., 2015). Vg-Gal4/Cyo; UAS-$(GR)_{80}$/TM6B flies were crossed with individual genetic mutant or UAS-RNAi lines for a specific gene, which were obtained from the Bloomington Drosophila Stock Center. For crosses with genetic mutant alleles, $w^{1118}$ flies were used as the control. For crosses with UAS-RNAi lines, UAS-GFP served as the control. After the cross, 3-5 days old adult flies of the F1 generation were scored under the dissecting microscope. The number of flies with or without the wing margin notching phenotype was counted.

Protein Interaction Network Analysis

To retrieve protein interaction data and build protein-protein interaction networks, Applicant queried the Proteomics Standard Initiative Common Query InterfaCe (PSICQUIC) web portal (www.ebi.ac.uk/Tools/webservices/psicquic/view/main.xhtml) for PPI data form the mentha, IntAct and MINT databases. Applicant restricted results to only human interactors that had been experimentally validated in AP-MS experiments (i.e., search terms MI:0006: anti bait coimmunoprecipitation and MI:0007: anti tag coimmunoprecipitation). The resulting data were combined with the most recently available dataset based on AP-MS interactions of ~5000 bait proteins from the Bioplex website (bioplex.hms.harvard.edu). Applicant used Cytoscape to visualize the resulting PPI dataset consisting of 14,352 nodes and 102,551 non-redundant edges. Applicant extracted PPI data for 361 SG proteins and used the Prefuse Force Directed Layout to visualize the network. The internal Cytoscape Network Analyzer plugin was used to calculate and visualize network parameters.

Protein Domain and Gene Ontology Analysis

Domain analysis was done by retrieving PFAM domains through the NCBI Conserved Domains Database (www.ncbi.nlm.nih.gov/Structure/cdd/cdd.shtml). Low complexity domains and intrinsically disordered regions were calculated as previously described (Beckmann et al., 2015; Conrad et al., 2016). Gene ontology enrichment analysis and PPI hub analysis was performed through the Enrichr Gene Ontology enrichment tool (amp.pharm.mssm.edu/Enrichr/) (Kuleshov et al., 2016). Results were ranked by the 'combined score', which combines p value and z-score by multiplication: c=log(p)*z.

Quantification and Statistical Analyses

MS Data Collection and Analysis

Samples were analyzed in triplicate using a Q-Exactive mass spectrometer (Thermo Scientific, San Jose, Calif.) with essentially the same nHPLC and instrument method as described previously (Gendron et al., 2016) with the following modifications: For input samples, peptides were eluted using a 60 min ACN gradient (45 minute 2%-30% ACN gradient, followed by a 5 minute 30%-60% ACN gradient, a 2 minute 60%95% gradient, with a final 8 minute isocratic step at 0% ACN) at a flow rate of 250 nl/min. A dynamic exclusion time of 20 s was used and singly charged ions, charge states above 6 and unassigned charge states were excluded. For IP samples, peptides were eluted using a 120 min ACN gradient (100 minute 2%-30% ACN gradient, followed by a 5 minute 30%-60% ACN gradient, a 5 minute 60%95% gradient, with a final 10 minute isocratic step at 0% ACN) at a flow rate of 250 nl/min. A dynamic exclusion time of 40 s was used and singly charged ions, charge states above 6 and unassigned charge states were excluded. The resultant RAW files were analyzed using Andromeda/MaxQuant (version 1.6.0.16) (Cox and Mann, 2008). Data were searched against a concatenated target-decoy database comprised of forward and reversed sequences from the reviewed UniprotKB/Swiss-Prot FASTA Human database (2015) with GFP and common contaminants appended (~22,000 entries). $Arg^{10}$ and $Lys^8$ were selected as isotope labels and trypsin was specified for protein digestion. Variable modifications for methionine oxidation and protein N terminus acetylation and a fixed modification for cysteine carbamidomethylation were allowed. A mass accuracy of ±50 ppm was specified for the first search and ±4.5 ppm for the main search. A maximum of 2 missed cleavages and 5 modifications were allowed per peptide and the maximum charge was set to 7. The minimum allowed peptide length was 7 amino acids and matching between runs was enabled for data obtained from the same cell line. The data were filtered using protein, peptide and site level false discovery rates of 0.01. Unique and razor peptides were used for quantification. Matches to common contaminants, reverse identifications and identifications based only on site-specific modifications were removed prior to further analysis.

To determine $\log_2$ H/L ratio cutoffs, proteins in each experimental replicate were ranked by descending $\log_2$ H/L ratios and the fraction of known SG proteins in a rolling window (size=200) was calculated. A cutoff was determined to be the point at which the frequency of known SG proteins fell below 2 times the background frequency. For each experimental design in HEK293T cells, proteins with logy H/L ratios above the cutoff in at least 2/3 (Exp. 2-4) or all 3 replicates (Exp.1) were retained as candidates. A final list of 123 candidate SG proteins in HEK293T cells was assembled from all hit candidates in Exp. 3 (stressed G3BP1-APEX2-GFP versus stressed NES-APEX2-GFP) that overlapped with hit candidates from Exp.1 (stressed G3BP1-APEX2-GFP versus unstressed G3BP1-APEX2-GFP) or Exp. 2 (stressed G3BP1-APEX2-GFP versus stressed G3BP1-APEX2-GFP without biotin phenol).

In parallel, individual peptide intensities were analyzed by an empirical Bayes approach (Kammers et al., 2015) using an adaption of the original R script (www.biostat.jhsph.edu/~kkammers/software/eupa/R_guide.html) suitable for SILAC data. Briefly, individual heavy and light peptide intensities were $\log_2$-transformed and protein-level intensities were calculated from the median of all peptides identified and quantified for each protein. Global median intensity levels were normalized and a moderated two-sample t test was performed, comparing heavy and light intensities for each protein. The resulting moderated p values are corrected for multiple hypothesis testing using a modified Benjamini-Hochberg false discovery rate (FDR) approach to determine a moderated q-value (q.mod) (Storey and Tibshirani, 2003). Proteins identified at a false-discovery rate (moderated q-value) of 0.05 were annotated as significantly different in abundance.

For neural progenitor cells (NPCs), Applicant only performed Exp.1 and 2 in biological duplicates, but using two different stressors ($NaAsO_2$ or thapsigargin) for each experiment. To identify candidate SG proteins in NPCs, Applicant determined logy H/L ratio cutoffs for each experimental replicate using an identical procedure to that used in HEK293T cells. For each stressor, a candidate list was compiled from proteins with ratios above the cutoff in 3 out of 4 combined replicates of Exps. 1 and 2. The resulting lists were combined to yield an exploratory list of 178 NPC SG candidates. To obtain sufficient power for statistical testing, Applicant combined all 4 replicates of each experimental design obtained with the two stressors. Only proteins with peptide intensity measurements across all 4 replicates were considered in the analysis, somewhat limiting the number of proteins for which statistical significance could be assessed.

Image Analysis

MetaXpress v3.1 software was used for all image analysis and quantifications were carried out using an in-house script (see Methods S1).

Data and Software Availability

The accession number for the proteomics data reported in this paper is Massive MS data repository (massive.ucsd.edu/ProteoSAFe/static/massive.jsp): MSV000081554.

Example 2

Use of UBAP2L Antisense Oligonucleotide to Treat Amyotrophic Lateral Sclerosis (ALS)

This example describes an exemplary method for treating amyotrophic lateral sclerosis (ALS) in a subject. A subject suffering from ALS is administered an antisense oligonucleotide (ASO) that hybridizes to a region within an UBAP2L messenger RNA (mRNA) molecule. The ASO does not hybridize to a region of the UBAP2L mRNA molecule that encodes for an ubiquitin associated (UBA) domain or arginine and glycine-rich motif (RGG domain).

Example 3

Monitoring Progression of Alzheimer's Disease (AD)

This example describes an exemplary method for monitoring the progression of Alzheimer's disease (AD) in a subject. A subject suffering from AD is administered a daily dose of a small interfering RNA (siRNA) comprising the nucleotide sequence of SEQ ID NO: 1 and/or SEQ ID NO: 2. A blood sample is obtained from the subject two weeks and four weeks after the administration of the siRNA. The blood samples are analyzed for the expression level of UBAP2L. If the UBAP2L expression level decreases over time (e.g., expression level of UBAP2L in the two week sample is higher than the expression level of UBAP2L in the four week sample), then the subject's AD is determined to be not progressing or worsening over time. In addition, the dose or dosing frequency of the siRNA may be maintained and/or decreased.

Example 4

Determining the Efficacy of a Neurodegenerative Disorder Therapy

This example describes an exemplary method for determining the efficacy of a neurodegenerative disorder therapy. A subject suffering from frontotemporal lobar degeneration (FTLD) is administered a daily dose of a neurodegenerative disorder therapy comprising a CRISPR system comprising: (a) an oligonucleotide encoding a CRISPR associated endonuclease (Cas) protein; and (b) an oligonucleotide comprising (i) a first region that hybridizes to an ubiquitin associated protein 2-like (UBAP2L) gene; and (ii) a scaffold sequence. A blood sample is obtained from the subject one and two months after the administration of the siRNA. The blood samples are analyzed for the expression level of UBAP2L. If the UBAP2L expression level decreases over time (e.g., expression level of UBAP2L in the one month sample is higher than the expression level of UBAP2L in the two month sample), then neurodegenerative disorder therapy is determined to be effective.

Example 5

Detection of Stress Granule Formation by Immunofluorescence

This example describes an exemplary method for detecting stress granule formation by immunofluorescence. The exemplary method comprises the following steps:

Grow cells to 50-80% confluent (appropriate coating to maximize adhesion)

Wash once with 1× PBS, fix in 4% PFA/PBS for 20-30min at room temperature.

Alternatively, for small volumes or fragile cells, add an equal amount of 8% PFA directly to media.

Wash once with 1× PBS.

Permeabilize with PBS+0.25% Triton-X for 10-15 min at room temperature (this step may be varied depending on the type of antigens to be detected, e.g., nuclear vs surface antigens).

Wash twice with 1× PBS.

Cells can be stored in 1× PBS for several days at 4° C. For longer storage, add 0.05% sodium azide or gentamicin (1:1000) to prevent contamination.

Incubate in blocking solution (PBS+5% goat serum+ 0.01% Tween-20) for 30-60 min at room temperature.

Dilute primary antibody to appropriate concentration in blocking solution and incubate overnight at 4° C. or 2-4 h at RT (depending on 1° antibody).

Wash four times in 1× PBST for 5 min each at room temperature.

Dilute secondary antibody to appropriate concentration in blocking solution (usually 1:500 for goat anti-mouse/rabbit Alexa488, Alexa555, Alexa568 etc) and incubate 1 h at room temperature.

Wash four times in 1× PBS for 5 min each at RT (include DAPI at 1:1000 in $2^{nd}$ wash for 10 min if not mounting slides or coverslips.

Mount in mounting media (e.g. ProLong Gold antifade with DAPI)

Let dry overnight at room temperature, seal with nail polish.

Store slides or plates at 4° C. Add 0.05% sodium azide or gentamicin (1:1000) for long-term storage.

Example 6

Detection of Stress Granule Formation by Granule Core Isolation

This example describes an exemplary method for detecting stress granule formation by granule core isolation. The exemplary method comprises the following steps:

HEK293T cells and CV-B smNPCs expressing G3BP1-GFP were grown to 75-90% confluency and stressed with sodium arsenite (500 uM and 250 uM for 60 min, respectively).

The culture media was aspirated.

Cells were washed once with 1× PBS at room temperature.

Cells were lysed for 10 minutes on ice with ice-cold lysis buffer (use 1.5-3.0 mL per well of 6 well; scale up 4 fold for 10 cm dish and 8 fold for 15 cm dish).

Cells were scraped off and collected in 15 mL centrifuge tubes in aliquots of 3 mL.

Lysates in these tubes were sonicated in an ice-cold water bath, 2× 10 s on low power and 1× 10 s on high power. Between sonication rounds, lysates in tubes were incubated on ice for 20 s.

Following sonication, the lysates were centrifuged at 1000 g for 5 min at 4° C. to remove nuclei. The supernatants were then transferred to new tubes and centrifuged at 18000 g for 20 min at 4° C. to pellet stress granules.

After decanting the supernatant, the pellet was resuspended in $\frac{1}{10}^{th}$ volume ice-cold lysis buffer by trituration.

The resuspended sample was finally centrifuged at 850 g for 2 min at 4° C. to pellet insoluble debris. The supernatant was collected as the stress granule enriched fraction. The same fractionation procedure was applied to unstressed cells as negative controls.

SG core lysis buffer:
Per 200 mL:
10 mL 1M Tris HCL pH 7.4
20 mL 1M potassium acetate
400 uL 1M magnesium acetate
1 mL 0.1M DTT
1 mL 10 mg/mL heparin
1 mL Nonidet P-40 or IGEPAL CA630
40 uL antifoam B
4 tabs edta free protease inhib (roche cat 05056489001); add fresh one tab per 50 mL
(total vol before water: 33.5 mL; divided by 20 is 1.675 mL)
166.5 mL water (×2=333 mL).

As an alternative, stress granule formation can also be detected by the stress granule core isolation protocol described in Jain et al., *Cell* (2016) 164(3): 487-498, which is incorporated by reference in its entirety.

Example 7

Detection of Stress Granule Formation by Fractionation

This example describes an exemplary method for detecting stress granule formation by fractionation. Briefly, the method comprises biochemically fractionating proteins based on their solubility in various detergents and buffers. This method comprises preparing cell lysates in a standard lysis buffer (e.g., RIPA) and pelleting the insoluble material (e.g., spin 10 min @15000 g). The insoluble pellet is then resuspended and triturated in more aggressive buffers (e.g., urea-thiourea-CHAPS, or buffers containing higher amounts of detergents, such as 1-2% SDS or Triton-X). The insoluble pellet, which is the insoluble protein aggregate (e.g., stress granule) is subsequently spun (10 min @15000 g) and assessed by western blotting.

Equivalents

The disclosure illustratively described herein can suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Thus, it should be understood that although the present disclosure has been specifically disclosed by preferred embodiments and optional features, modification, improvement and variation of the disclosure embodied therein herein disclosed can be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. Several references are identified by author name and date. The full bibliographic citation for each is provided in the reference section below. In case of conflict, the present specification, including definitions, will control.

SEQUENCE LISTING

| Description | Sequence | SEQ ID NO: |
|---|---|---|
| UBAP2L-sh3 (siRNA) | CCGGGCCAATACTGATGATAACTATCTCGAGATAGTTATCATCAGTATTGGCTTTTT | 1 |
| UBAP2L-sh4 (siRNA) | CCGGCGCAGCAGAATACCCTTTCATCTCGAGATGAAAGGGTATTCTGCTGCGTTTTT | 2 |
| UBAP2L-gRNA1 | CCTCAAAGTCAGCATCATTA | 3 |
| UBAP2L-gRNA2 | AAGCAATCACACATTCATCC | 4 |
| UBAP2L (NCBI Ref. Sequence: NM_014847.2) | GAGACTGAGTATTCTACCTTGTAAATACTGTTATTTGTATATACTGTAAATGATGACATCGGTGGGCACTAACCGAGCCCGGGGAAACTGGGAACAACCTCAAAACCAAAACCAGACACAGCACAAGCAGCGGCCACAGGCCACTGCAGAACAAATTAGACTTGCACAGATGATTTCGGACCATAATGATGCTGACTTTGAGGAGAAGGTGAAACAATTGATTGATATTACAGGCAAGAACCAGGATGAATGTGTGATTGCTTTGCATGACTGCAATGGAGATGTCAACAGAGCTATCAATGTTCTTCTGGAAGGAAACCCAGACACGCATTCCTGGGAGATGGTCGGGAAGAAGAAGGGAGTCTCAGGCCAGAAGGATGGTGGCCAGACGGAATCCAATGAGGAAGGCAAAGAAAATCGAGACCGGGACAGAGACTATAGTCGGCGACGTGGTGGGCCACCAAGACGGGGGAGAGGTGCCAGCCGTGGACGAGAGTTTCGAGGTCAGGAAAATGGATTGGATGGCACCAAGAGTGGAGGGCCTTCTGGAAGAGGAACAGAAAGAGGCAGAAGGGGCCGTGGCCGAGGCAGAGGTGGCTCTGGTAGGCGAGGAGGAAGGTTTTCTGCTCAAGGAATGGGAACCTTTAACCCAGCTGATTATGCAGAGCCAGCCAATACTGATGATAACTATGGCAATAGCAGCGGCAATACGTGGAACAACACTGGCCACTTTGAACCAGATGATGGGACGAGTGCATGGAGGACTGCAACAGAGGAGTGGGGGACTGAAGATTGGAATGAAGATCTTTCTGAGACCAAGATCTTCACTGCCTCTAATGTGTCTTCAGTGCCTCTGCCTGCGGAGAATGTGACAATCACTGCTGGTCAGAGAATTGACCTTGCTGTTCTGCTGGGGAAGACACCATCTACAATGGAGAATGATTCATCTAATCTGGATCCGTCTCAGGCTCCTTCTCTGGCCCAGCCTCTGGTGTTCAGTAATTCGAAGCAGACTGCCATATCACAGCCTGCTTCAGGGAACACATTTTCTCATCACAGTAGTGGTGAGCATGTTAGGGAAAGGATTTGGTGATGTCGGTGAAGCTAAAGGCGGCAGTACTACAGGCTCCCAGTTCTTGGAGCAATTCAAGACTGCCCAAGCCCTGGCTCAGTTGGCAGCTCAGCATTCTCAGTCTGGAAGCACCACCACCTCCTCTTGGGACATGGGCTCGACGACACAATCCCCATCACTGGTGCAGTATGATTTGAAGAACCCAAGTGATTCAGCAGTGCACAGCCCCTTTACAAAGCGCCAGGCTTTTACCCCATCTTCAACCATGATGGAGGTGTTCCTTCAGGAGAAGTCACCTGCAGTGGCTACCTCCACAGCTGCACCTCCACCTCCGTCTTCTCCTCTGCCAAGCAAATCCACATCGGCTCCACAGATGTCGCCTGGATCTTCAGACAACCAGTCCTCTAGCCCTCAGCCGGCTCACCAGAAACTGAAACAGCAGAAGAAAAAAGCCTCCTTGACTTCTAAGATTCCTGCTCTGGCTGTGGAGATGCCTGGCTCAGCAGATATCTCAGGGCTAAACCTGCAGTTTGGGGCATTGCAGTTTGGGTCAGAGCCTGTCCTTTCTGATTATGAGTCCACCCCCACCACGAGCGCCTCTTCAAGCCAGGCTCCAAGTAGCCTGTATACCAGCACGGCCAGTGAATCATCCTCTACAATTTCATCTAACCAGAGTCAGGAGTCTGGTTATCAGAGCGGCCCAATTCAGTCGACAACCTATACCTCCCAAAATAATGCTCAGGGCCCTCTTTATGAACAGAGATCCACACAGACTCGGCGGTACCCCAGCTCCATCTCTTCATCACCCCAAAAGGACCTGACTCAGGCAAAGAATGCTTCAGTTCTGTGCAGGCCACGCAGTTACAGACCACACAATCTGTTGAAGGTGCTACAGGCTCTG | 5 |

SEQUENCE LISTING

| Description | Sequence | SEQ ID NO: |
|---|---|---|
| | CAGTGAAATCTGATTCACCTTCCACTTCTAGCATCCCCCCTCTCAA<br>TGAAACGGTATCTGCAGCTTCCTTACTGACGACAACCAATCAGCA<br>TTCATCCTCCTTGGGTGGCTTGAGCCACAGTGAGGAGATTCCAAA<br>TACTACCACCACAACACAGCAGCACGTTATCTACGCAGCAGAA<br>TACCCTTTCATCATCAACATCTTCTGGGCGCACTTCGACATCCACT<br>CTTTTGCACACAAGTGTGGAGAGTGAGGCGAATCTCCATTCTTCC<br>TCCAGCACTTTTTCCACCACATCCAGCACAGTCTCTGCACCTCCCC<br>CAGTGGTCAGTGTCTCCTCCAGTCTCAATAGTGGCAGTAGCCTGG<br>GCCTCAGCCTAGGCAGCAACTCCACTGTCACAGCCTCGACTCGAA<br>GCTCAGTTGCTACGACTTCAGGAAAAGCTCCTCCCAACCTCCCTC<br>CTGGGGTCCCGCCGTTGTTGCCTAATCCGTATATTATGGCTCCAGG<br>GCTGTTACATGCCTACCCGCCACAAGTATATGGTTATGATGACTT<br>GCAGATGCTTCAGACAAGATTTCCATTGGATTACTACAGCATCCC<br>ATTTCCCACACCCACTACTCCGCTGACTGGGAGGGATGGTAGCCT<br>GGCCAGCAACCCTTATTCTGGTGACCTCACAAAGTTCGGCCGTGG<br>GGATGCCTCCTCCCCAGCCCCGGCCACAACCTTGGCCCAACCCCA<br>ACAGAACCAGACGCAGACTCACCATACCACGCAGCAGACATTCC<br>TGAACCCGGCGCTGCCTCCTGGCTACAGTTACACCAGCCTGCCAT<br>ACTATACAGGGGTCCCGGGCCTCCCAGCACCTTCCAGTATGGGC<br>CTGCTGTGTTCCCTGTGGCTCCTACCTCTTCCAAGCAGCATGGTGT<br>GAATGTCAGTGTGAATGCATCGGCCACCCCTTTCCAACAGCCGAG<br>TGGATATGGGTCTCATGGATACAACACTGGTGTTTCAGTCACCTC<br>CAGTAACACGGGCGTGCCAGATATCTCGGGTTCTGTGTACTCCAA<br>AACCCAGCAGTCCTTTGAGAAACAAGGTTTTCATTCCGGTACTCC<br>TGCTGCTTCCTTCAACTTGCCTTCAGCCCTAGGAAGTGGGGGCCC<br>CATCAATCCGGCCACAGCTGCTGCCTACCCACCTGCCCCCTTTATG<br>CACATTCTGACCCCCCATCAGCAGCCGCATTCTCAGATCCTTCACC<br>ATCACCTGCAGCAGGATGGCCAGACGGGCAGCGGGCAACGTAGC<br>CAGACCAGCTCCATCCCGCAGAAGCCCCAGACCAACAAGTCTGCC<br>TACAACAGCTACAGCTGGGGGGCCAACTGAGGCCCTGACCCTCTT<br>CTCCCGGTCCCATCTTCTGAGAGGGCTTCTCAGCCTGGAAACTAT<br>GGAAACAGCATCAAAGAGAAAGGAATGTGGGGGGTTTCCGCTGC<br>CCCCCACCCCCAGCGGCCCACCCCATGCCTCAGCTTCATGTCTGTC<br>CCATTCCTATACCATCCCCACCCTGTTGTATGTATTATAGGATTTG<br>TATTTTCTCCTTTTTTTTCCCCCTTCCATTCCTTCTCCCCTCTTGCAT<br>TCAAGATTATGAAACTTTGCTATGGGCCCTGCACTTCCTTTGCTTC<br>CTCCTGTTCACCCTGGTGGTGTACGGATGAGGCGGGGAGGTGGGA<br>CCCCCAAACATATATCAGCCCAACAGCCCTAAGTCTCCTTCTTTAT<br>TATTAGGAAACAACAACAACAACAAACAAAAAAATGGCGTCAT<br>GAATATGAACAGCATTGTCAGATGAATTAGTTGAAGTGGTTTTTT<br>TTTTGTTTTTTTTTTTTTTGTACTGTGTCCTCAAATTTAATGGA<br>TTAATGTGTCTTGTATATAAAAAGAAAACCTCTACCTTCAAA<br>AAAAAAAAAAAAA | |
| UBAP2L<br>(NCBI Ref.<br>Sequence:<br>NM_014847.2) | MMTSVGTNRARGNWEQPQNQNQTQHKQRPQATAEQIRLAQMISDH<br>NDADFEEKVKQLIDITGKNQDECVIALHDCNGDVNRAINVLLEGNPD<br>THSWEMVGKKKGVSGQKDGGQTESNEEGKENRDRDRDYSRRGGP<br>PRRGRGASRGREFRGQENGLDGTKSGGPSGRGTERGRRGRGRGG<br>SGRRGGRFSAQMGMTFNPADYAEPANTDDNYGNSSGNTWNNTGHF<br>EPDDGTSAWRTATEEWGTEDWNEDLSETKIFTASNVSSVPLPAENVT<br>ITAGQRIDLAVLLGKTPSTMENDSSNLDPSQAPSLAQPLVFSNSKQTA<br>ISQPASGNTFSHHSMVSMLGKGFGDVGEAKGGSTTGSQFLEQFKTA<br>QALAQLAAQHSQSGSTTTSSWDMGSTTQSPSLVQYDLKNPSDSAVH<br>SPFTKRQAFTPSSTMMEVFLQEKSPAVATSTAAPPPPSSPLPSKSTSAP<br>QMSPGSSDNQSSSPQPAHQKLKQQKKASLTSKIPALAVEMPGSADI<br>SGLNLQFGALQFGSEPVLSDYESTPTTSASSSQAPSSLYTSTASESSSTI<br>SSNQSQESGYQSGPIQSTTYTSQNNAQGPLYEQRSTQTRRYPSSISSSP<br>QKDLTQAKNGFSSVQATQLQTTQSVEGATGSAVKSDSPSTSSIPPLNE<br>TVSAASLLTTTNQHSSSLGGLSHSEEIPNTTTTQHSSTLSTQQNTLSSS<br>TSSGRTSTSTLLHTSVESEANLHSSSSTFSTTSSTVSAPPPVVSVSSSLN<br>SGSSLGLSLGSNSTVTASTRSSVATTSGKAPPNLPPGVPPLLPNPYIMA<br>PGLLHAYPPQVYGYDDLQMLQTRFPLDYYSIPFPTPTTPLTGRDGSL<br>ASNPYSGDLTKFGRGDASSPAPATTLAQPQQNQTQTHHTTQQTFLNP<br>ALPPGYSYTSLPYYTGVPGLPSTFQYGPAVFPVAPTSSKQHGVNVSV<br>NASATPFQQPSGYGSHGYNTGVSVTSSNTGVPDISGSVYSKTQQSFE<br>KQGFHSGTPAASFNLPSALGSGGPINPATAAAYPPAPFMHILTPHQQP<br>HSQILHHHLQQDGQTGSGQRSQTSSIPQKPQTNKSAYNSYSWGAN | 6 |
| UBA domain<br>nucleotide | CAAAACCAGACACAGCACAAGCAGCGGCCACAGGCCACTGCAGA<br>ACAAATTAGACTTGCACAGATGATTTCGGACCATAATGATGCTGA<br>CTTTGAGGAGAAGGTGAAACAATTGATTGATATTACAGGCAAGA<br>ACCAGGATGAATGTGTGATTGCTTTGCATGACTGCAATGGAGATG<br>TCAACAGAGCTATCAATGTTCTTCTGGAAGGAAACCCAGACACGC<br>ATTCCTGGGAGATGGTCGGGAAGAAGAAGGGAGTCTCAGGCCAG | 7 |

SEQUENCE LISTING

| Description | Sequence | SEQ ID NO: |
|---|---|---|
| UBA domain amino acid | QNQTQHKQRPQATAEQIRLAQMISDHNDADFEEKVKQLIDITGKNQDECVIALHDCNGDVNRAINVLLEGNPDTHSWEMVGKKKGVSGQ | 8 |
| RGG domain nucleotide | CGTGGTGGGCCACCAAGACGGGGGAGAGGTGCCAGCCGTGGACGAGAGTTTCGAGGTCAGGAAAATGGATTGGATGGCACCAAGAGTGGAGGGCCTTCTGGAAGAGGAACAGAAAGAGGCAGAAGGGGCCGTGGCCGAGGCAGAGGTGGCTCTGGTAGGCGAGGAGGA | 9 |
| RGG domain amino acid | RGGPPRRGRGASRGREFRGQENGLDGTKSGGPSGRGTERGRRGRGRGRGGSGRRGG | 10 |

TABLE 1

Stress Granule-Associated Proteins Gene Symbol

ADAR
AGO1
AGO2
AHSA1
AKAP9
ALYREF
ANG
APOBEC3G
ATP2C1
ATXN2
ATXN2L
BRF1
CALR
CAPRIN1
CASC3
CCAR1
CCR4
CDC37
CELF1
CELF2
CIRBP
CNBP
CNOT8
CPEB1
CPEB2
CPEB3
CPEB4
CYFIP2
DAZAP2
DAZL
DCP1A
DCP1B
DCP2
DDX1
DDX39A
DDX39B
DDX3X
DDX5
DDX58
DDX6
DHX36
DHX58
DHX9
DYRK3
EDC3
EDC4
EIF2A
EIF2AK2
EIF2S1
EIF2S2
EIF2S3
EIF3A
EIF3B
EIF3C
EIF3D
EIF3E
EIF3F
EIF3G
EIF3H
EIF3I
EIF3J
EIF3K
EIF3L
EIF3M
EIF4A1
EIF4A2
EIF4A3
EIF4B
EIF4E
EIF4G1
EIF4G2
EIF4G3
EIF4H
EIF5
EIF5A
EIF5A2
EIF5B
ELAVL1
ELAVL2
ELAVL3
ELAVL4
ETF1
EWSR1
FASTK
FMR1
FUBP1
FUBP3
FUS
FXR1
FXR2
G3BP1
G3BP2
GBP2
GIGYF2
GRB7
GSPT1
GSPT2
HDAC6
HNRNPA0
HNRNPA1
HNRNPA2B1
HNRNPA3
HNRNPAB
HNRNPC
HNRNPD
HNRNPH1
HNRNPK
HNRNPL
HNRNPM
HNRNPR

TABLE 1-continued

Stress Granule-Associated Proteins
Gene Symbol

HNRNPU
HOPX
HSP90AA1
HSPA8
HSPB1
HTT
IGF2BP1
IGF2BP2
IGF2BP3
ILF2
ILF3
IPO8
KHDRBS1
KHSRP
KPNA2
KPNA4
KPNA5
KPNB1
LARP4
LARP4B
LIN28A
LSM1
LSM12
LSM14A
LSM14B
MAP1LC3A
MAPK8
MATR3
MBNL1
MCRIP1
MCRIP2
MEX3A
MEX3B
MSI1
MSI2
NCL
NONO
NPM1
NRG2
NUFIP2
NXF1
NXF5
OAS1
OAS2
OAS3
OGFOD1
OGG1
OGN
PABPC1
PABPC3
PABPC4
PABPC5
PAN2
PAN3
PATL1
PCBP1
PCBP2
PFN1
PFN2
PHB2
PKP1
PKP3
PQBP1
PRKCA
PRKRA
PRMT1
PSD3
PSPC1
PTBP1
PTK2
PUM1
PUM2
PURA
PURB
QKI
RACK1
RAN

TABLE 1-continued

Stress Granule-Associated Proteins
Gene Symbol

RBM3
RBM4
RBM42
RC3H1
RHOA
RNASEL
RNH1
ROCK1
RPL3
RPS18
RPS19
RPS3
RPS6
RPS6KA3
RTCA
SAMD4A
SERBP1
SFPQ
SMG1
SMN1
SMN2
SND1
SPATS2L
STAU1
STAU2
SYNCRIP
TAF15
TARDBP
TDRD3
TIA1
TIAL1
TNPO1
TNRC6A
TNRC6B
TRAF2
TRIM2
TRIM3
UPF1
UPF2
UPF3A
UPF3B
USP10
USP6
WDR62
XRN1
YBX1
YTHDF1
YTHDF2
ZBP1
ZC3HAV1
ZFP36

TABLE 2

List of Candidate SG Proteins Identified by Mass Spectrometry
Gene Symbol

ANXA11
ANXA7
APOBEC3C
ASCC1
ATXN2
ATXN2L
BCLAF1
C14orf166
CAPRIN1
CELF1
CIRBP
CSDE1
CSTB
DAZAP1
DDX1
DDX3X
DHX36

TABLE 2-continued

List of Candidate SG Proteins Identified by Mass Spectrometry
Gene Symbol

DSP
DYNLL1
EIF3A
EIF3C
EIF3E
EIF3G
EIF3H
EIF3J
EIF3L
EIF4A1
EIF4A2
EIF4B
EIF4G1
EIF4H
ELAVL1
FAM120A
FAM98A
FMR1
FUBP1
FUBP3
FUS
FXR1
FXR2
G3BP1
G3BP2
GLRX3
GRSF1
GSPT1
HDLBP
HELZ
HNRNPA2B1
HNRNPA3
HNRNPAB
HNRNPDL
HNRNPF
HNRNPH1
HNRNPH3
HSPB1
IGF2BP1
IGF2BP2
IGF2BP3
KHSRP
KPNA1
KPNA3
LARP4
LARP4B
LASP1
LIG3
LIN28B
LSM12
MAGED1
MAPK1IP1L
MAPRE2
MSI1
MSI2
NUFIP2
OSBPL9
OTUD4
P4HB
PABPC1
PABPC4
PCBP1
PCBP2
PDIA3
PEF1
PGP
PPP2R1B
PRRC2A
PRRC2B
PRRC2C
PTBP1
PTBP3
PUM1
PUM2
PURA
RBM3
RBM38
RBM4
RBMS1
RBMS2
RTCB
SEC24C
SRI
SRSF1
SRSF9
STAU1
STRAP
SYNCRIP
TAF15
THRAP3
TIA1
TIAL1
TNPO1
TRIM25
UBAP2
UBAP2L
UPF1
UPF3B
USP10
XRN1
YBX1
YBX3
YTHDF1
YTHDF2
YTHDF3
ZC3HAV1

TABLE 3

Stress granule RBPs by stress-type specificity

| HeLa NaAsO2 specific | HeLa heat shock-specific | HeLa NaAsO2 and heat shock-specific | | | | |
|---|---|---|---|---|---|---|
| Gene Symbol | Gene Symbol | Gene Symbol | Gene Symbol | Gene Symbol | Gene Symbol | Gene Symbol |
| ABCF1 | DDX6 | AQR | EIF3G | FXR2 | PABPC4 | SRSF5 |
| ADD1 | EIF2C1 | ATXN2 | EIF3H | G3BP1 | PCBP2 | TIAL1 |
| DAZAP1 | SF1 | BCCIP | EIF4B | G3BP2 | PRRC2C | UBAP2L |
| EIF3A | | CASC3 | EIF4G1 | IGF2BP1 | PSPC1 | ZONAB |
| EIF4G3 | | CIRBP | EIF4H | IGF2BP3 | PUM1 | |
| FUS | | DDX3X | FAM120A | METAP2 | PUM2 | |
| NOLC1 | | DDX3Y | FMR1 | MSI2 | RBM25 | |

TABLE 3-continued

Stress granule RBPs by stress-type specificity

| HeLa NaAsO2 specific | HeLa heat shock-specific | HeLa NaAsO2 and heat shock-specific | | | | |
|---|---|---|---|---|---|---|
| Gene Symbol | Gene Symbol | Gene Symbol | Gene Symbol | Gene Symbol | Gene Symbol | Gene Symbol |
| SLBP | | DROSHA | FUBP3 | NKRF | SAFB2 | |
| XRN2 | | EIF3D | FXR1 | NUFIP2 | SND1 | |

TABLE 4

Stress Granule RBPs by cell-type specificity

| HepG2 specific | NPC specific | HepG2 and HeLa specific | HepG2, HeLa, and NPC-specific | | |
|---|---|---|---|---|---|
| RECQL | CCDC124 | SLBP | AQR | FUBP3 | RBM25 |
| RPS11 | DHX30 | | ATXN2 | FUS | SND1 |
| SRSF7 | DHX33 | HepG2 and NPC specific | BCCIP | FXR1 | SRSF5 |
| SRSF9 | AGO1 | | CASC3 | FXR2 | TIAL1 |
| HeLa specific | EIF4A2 | CELF1 | CIRBP | G3BP1 | UBAP2L |
| EIF3A | EIF4A3 | DDX1 | DAZAP1 | G3BP2 | YBX3 |
| NOLC1 | HSPD1 | LIN28B | DDX3X | IGF2BP1 | |
| | IGF2BP2 | PPP1R8 | DDX3Y | IGF2BP3 | |
| | MSI1 | RBM17 | DROSHA | METAP2 | |
| | NELFE | ZC3H11A | EIF3D | MSI2 | |
| | PARN | HeLa and NPC-specific | EIF3G | NKRF | |
| | PNPT1 | | EIF3H | NUFIP2 | |
| | RBM15 | ABCF1 | EIF4B | PABPC4 | |
| | RPS24 | ADD1 | EIF4G1 | PCBP2 | |
| | SRP68 | SAFB2 | EIF4G3 | PRRC2C | |
| | TRIP6 | XRN2 | EIF4H | PSPC1 | |
| | TROVE2 | | FAM120A | PUM1 | |
| | UTP18 | | FMR1 | PUM2 | |

TABLE 5

List of RBPs based on localization

| Cell body | | | Neuronal Projection | | |
|---|---|---|---|---|---|
| Control & Mutant | | | Control | Mutant | |
| ADD1 | FMR1 | PCBP2 | EIF4B | CIRBP | MSI1 |
| AQR | FUBP3 | PNPT1 | FXR1 | DDX3X | NKRF |
| ATXN2 | FXR1 | PRRC2C | FXR2 | EIF4B | NUFIP2 |
| CASC3 | FXR2 | PSPC1 | SND1 | FAM120A | PABPC4 |
| CIRBP | G3BP1 | PUM1 | | FMR1 | PCBP2 |
| DAZAP1 | HSPD1 | RBM15 | | FXR1 | RBM15 |
| DDX3X | IGF2BP1 | RBM25 | | FXR2 | RBM25 |
| DDX3Y | IGF2BP2 | SAFB2 | | G3BP1 | SAFB2 |
| EIF2C1 | IGF2BP3 | SND1 | | IGF2BP1 | SND1 |
| EIF3G | LIN28B | SRP68 | | IGF2BP2 | UTP18 |
| EIF3H | MSI1 | TIAL1 | | IGF2BP3 | XRN2 |
| EIF4B | MSI2 | TRIP6 | | | |
| EIF4G1 | NKRF | TROVE2 | | | |
| EIF4G3 | NUFIP2 | UTP18 | | | |
| EIF4H | PABPC4 | XRN2 | | | |
| FAM120A | PARN | YBX3 | | | |
| | ZC3H11A | | | | |

TABLE 6

List of RBP localization pattern in untreated control MNs

| Cell body | | | Neuronal projections | | |
|---|---|---|---|---|---|
| CASC3 | FXR1 | PSPC1 | ADD1 | FAM120A | RBM15 |
| CIRBP | FXR2 | PUM1 | AQR | HSPD1 | SLBP |
| CUGBP1 | G3BP2 | PUM2 | ATXN2 | IGF2BP1 | SND1 |
| DDX3X | IGF2BP2 | RBM25 | DAZAP1 | NELFE | SRP68 |
| EIF3G | IGF2BP3 | RECQL | DDX1 | NKRF | SRSF7 |
| EIF3H | LIN28B | RPS24 | DDX3Y | PARN | TRIP6 |
| EIF4A3 | METAP2 | SAFB2 | DROSHA | PNPT1 | TROVE2 |
| EIF4G1 | MSI1 | SRSF5 | EIF2C1 | PPP1R8 | ZC3H11A |
| EIF4G3 | MSI2 | SRSF9 | EIF4B | PRRC2C | YBX3 |
| EIF4H | NUFIP2 | TIAL1 | | | |
| FMR1 | PABPC4 | UTP18 | | | |
| FUBP3 | PCBP2 | XRN2 | | | |

TABLE 7

Oligonucleotides

| SEQ ID NO: | Oligo name | Sequence | Use and additional information |
|---|---|---|---|
| 11 | G3BP1_gRNA4_F | caccTCATGCAGCCATACAAACCC | Cloning of G3BP1 gRNAs into px458 Cas9 expression plasmid |
| 12 | G3BP1_gRNA4_R | aaacGGGTTTGTATGGCTGCATGA | |
| 13 | G3BP1_gRNA5_F | caccTCCATGAAGATTCACTGCCG | |
| 14 | G3BP1_gRNA5_R | aaacCGGCAGTGAATCTTCATGGA | |
| 15 | G3BP_5AoH_v15_NdeI_F | TCAGAGCAGATTGTACTGAGAGTGCAC CATATG TCCCCGGCCCTTAGTTTGCTAGTCCT | Amplification of homology arms for donor G3BP1-APEX2-GFP donor plasmid |
| 16 | V5_loxP_1-15_R | TGCTATACGAAGTTATcgtagaatcg agaccgaggagagggttagggataggataccG A | |
| 17 | G3BP_3AoH_SP_SalI_F | cggcatggacgagctgtacaagtaaGTCGAC ATCTTCATGGATCTTCATGCAG CCATACA | |
| 18 | G3BP_3AoH_v12_HR_SphI_R | AGCTATGACCATGATTACGCCA AGCTT GCATGC CCATCAATAAAAGAGAACCATA AC | |
| 19 | G3BP_intmap_F1 | AGCCACTGAAGAACCCAGAA | Integration mapping of APEX2-GFP into G3BP1 locus |
| 20 | attB1_UBAP2L_F | GGGGACAAGTTTGTACAAAAA AGCAGGCTTCACCATGATGACA TCGGTGGGCACTAACCG | Cloning of full-length UBAP2L into pDONR221 gateway plasmid |
| 21 | attB2_UBAP2L_R | GGGGACCACTTTGTACAAGAAA GCTGGGTTTTActtgtagagctcgtccatg ccg | |
| 22 | UBAP2L_deltaUBA_F | AAGGATGGTGGCCAGAC | Deletion of UBA domain in UBAP2L by PCR |
| 23 | UBAP2L_deltaUBA_R | GTTTTGAGGTTGTTCCCAG | |
| 24 | UBAP2L_intseq_F1 | TCTGCTCAAGGAATGGGAAC | Sequence verification of cloned UBAP2L constructs |
| 25 | UBAP2L_intseq_F2 | ACAGATGTCGCCTGGATCTT | |
| 26 | UBAP2L_intseq_F3 | TCCATTCTTCCTCCAGCACT | |
| 27 | UBAP2L_intseq_F4 | TCCTTCAACTTGCCTTCAGC | |
| 28 | pLKO.1-shRNA-control | AACAAGATGAAGAGCACCAAC TCGAGTTGGTGCTCTTCATCTTG TT | non targeting, scrambled siRNA |
| 1 | UBAP2L-Sh3 | CCGGGCCAATACTGATGATAAC TATCTCGAGATAGTTATCATCA GTATTGGCTTTTT | siRNA against UBAP2L, TRCN0000007680, targets NM_014847.2-671s1c1 |
| 2 | UBAP2L-Sh4 | CCGGCGCAGCAGAATACCCTTT CATCTCGAGATGAAAGGGTATT CTGCTGCGTTTTT | siRNA against UBAP2L, TRCN0000007681, targets NM_014847.2-2145s1c1 |

TABLE 8

| REAGENT or RESOURCE | SOURCE | IDENTIFIER |
|---|---|---|
| hnRNPA2/B1 D290v-1.1 hPSC | Generated in-house, (Martinez et al., 2016) | N/A |
| hnRNPA2/B1 D290v-1.2 hPSC | Generated in-house, (Martinez et al., 2016) | N/A |

TABLE 8-continued

| REAGENT or RESOURCE | SOURCE | IDENTIFIER |
|---|---|---|
| C9-3.2 $G_4C^2$ repeat-expansion hiPSC | Generated in-house, fibroblasts described in (Lagier-Tourenne et al., 2013) | N/A |
| C9-5.2 $G_4C^2$ repeat-expansion hiPSC | Generated in-house, fibroblasts described in (Lagier-Tourenne et al., 2013) | N/A |
| C9-6.3 $G_4C^2$ repeat-expansion hiPSC | Generated in house, fibroblasts described in (Lagier-Tourenne et al., 2013) | N/A |
| Experimental Models: Organisms/Strains | | |
| D. melanogaster: strain w[1118] | Gao Lab | N/A |
| D. melanogaster: UAS-GFP strain | Gao Lab | N/A |
| D. melanogaster: UAS-(GR)$_{80}$ transgenic strain: Vg-Gal4: UAS-(GR)$_{80}$/TM6B | (Yang et al., 2015) | N/A |
| D. melanogaster: Mutant allele of Bel/DDX3X/Y y[1] w[67c23]; P{w[+mC] y[+mDint2] = EPgy2}belEY08943] | Bloomington Drosophila Stock Center | BDSC: 19945; Flybase: FBst001945 |
| D. melanogaster: RNAi of Bel/DDX3X/Y y[1] v[1]; P{y[+t7.7] v[+t1.8] = TRiP.JF02884}attP2 | Bloomington Drosophila Stock Center | BDSC: 28049; Flybase: FBst0028049 |
| D. melanogaster: RNAi of Bel/DDX3X/Y y[1] sc[*] v[1]; P{y[+t7.7] v[+t1.8] = TRiP.GL00205}attP2 | Bloomington Drosophila Stock Center | BDSC: 35302; Flybase: FBst0035302 |
| D. melanogaster: Mutant allele of Hrb27C/DAZAP1 w[1118]; PBac{w[+mC] = WH}Hrb27C[f04375]/CyO | Bloomington Drosophila Stock Center | BDSC: 18765; Flybase: FBst0018765 |
| D. melanogaster: RNAi of Hrb27C/DAZAP1 y[1] v[1]; P{y[+t7.7] v[+t1.8] = TRiP.JF01477}attP2 | Bloomington Drosophila Stock Center | BDSC: 31684; Flybase: FBst0031684 |
| D. melanogaster: RNAi of Hrb27C/DAZAP1 y[1] v[1]; P{y[+t7.7] v[+t1.8] = TRiP.JF01478}attP2 | Bloomington Drosophila Stock Center | BDSC: 31685; Flybase: FBst0031685 |
| D. melanogaster: Mutant allele of Lig/UBAP2(L) w[1118]; PBac{w[+mC] = RB}lig[e01268]/CyO | Bloomington Drosophila Stock Center | BDSC: 18242; Flybase: FBst0018242 |
| D. melanogaster: Mutant allele of Lig/UBAP2(L) y[1]; P{y[+mDint2] w[BR.E.BR] = SUPor-P}lig[KG08208]/CyO; y[506] | Bloomington Drosophila Stock Center | BDSC: 14943; Flybase: FBst0014943 |
| D. melanogaster: RNAi of Lig/UBAP2(L) y[1] v[1]; P{y[+t7.7] v[+t1.8] = TRiP.HMJ23346}attP40 | Bloomington Drosophila Stock Center | BDSC: 61857; Flybase: FBst0061857 |
| D. melanogaster: Mutant allele of Psi/FUBP1/3 y[1] w[*]; P{w[+mC] = EP}Psi[G5862] | Bloomington Drosophila Stock Center | BDSC: 27192; Flybase: FBst0027192 |
| D. melanogaster: RNAi of Psi/FUBP1/3 y[1] v[1]; P{y[+t7.7] v[+t1.8] = TRiP.JF01247}attP2 | Bloomington Drosophila Stock Center | BDSC: 31301; Flybase: FBst0031301 |
| D. melanogaster: RNAi of Psi/FUBP1/3 y[1] v[1]; P{y[+t7.7] v[+t1.8] = TRiP.JF01247}attP2 | Bloomington Drosophila Stock Center | BDSC: 31683; Flybase: FBst0031683 |
| D. melanogaster: RNAi of Psi/FUBP1/3 y[1] sc[*] v[1]; P{y[+t7.7] v[+t1.8] = TRiP.HMS00140}attP2 | Bloomington Drosophila Stock Center | BDSC: 34825; Flybase: FBst0034825 |
| D. melanogaster: Mutant allele of Unr/CSDE1 y[1] w[*]; P{w[+mC] = EP}Psi[G5862] | Bloomington Drosophila Stock Center | BDSC: 17673; Flybase: FBst0017673 |
| D. melanogaster: Mutant allele of Unr/CSDE1 w[1118]; PBac{w[+mC] = PB}Unr[c01923] | Bloomington Drosophila Stock Center | BDSC: 10757; Flybase: FBst0010757 |

TABLE 9

| REAGENT or RESOURCE | SOURCE | IDENTIFIER |
|---|---|---|
| D. melanogaster: RNAi of Unr/CSDE1 y[1] sc[*] v[1]; P{y[+t7.7] v[+t1.8] = TRiP.HMS00428}attP2 | Bloomington Drosophila Stock Center | BDSC: 32432; Flybase: FBst0032432 |
| D. melanogaster: RNAi of Unr/CSDE1 y[1] v[1]; P{y[+t7.7] v[+t1.8] = TRiP.JF02496}attP2 | Bloomington Drosophila Stock Center | BDSC: 29334; Flybase: FBst0029334 |
| D. melanogaster: GMR-GAL4/CyO, tub-GAL80; UAS-FUS-hR521C/TM6B, Tb | (Periz et al., 2015) | N/A |
| D. melanogaster: GMR-GAL4, UAS-TDP-43-hM337V/CyO, tub-GAL80 | (Periz et al., 2015) | N/A |
| D. melanogaster: Rox8e04432 | Exelixis Collection at Harvard University | PBac{RB}Rox8e04432; Flybase: FBst1015699 |
| D. melanogaster: Rbp6d08411 | Exelixis Collection at Harvard University | P{XP}Rbp6d08411; Flybase: FBst1011661 |
| D. melanogaster: ligf03269 | Exelixis Collection at Harvard University | PBac{WH}liogf03269; Flybase: FBst1018357 |
| D. melanogaster: CG2889d07154 | Exelixis Collection at Harvard University | P{XP}CG2883d07154 mapped internally; Flybase: FBst1011297 |
| D. melanogaster: D12e01238 | Exelixis Collection at Harvard University | PBac{RB}D12e01238: mapped internaly; Harvard Only |
| D. melanogaster: Su(var)205c06825 | Exelixis Collection at Harvard University | PBac{PB}Su(var)205c05825; Flybase: FBst1008382 |

TABLE 9-continued

| REAGENT or RESOURCE | SOURCE | IDENTIFIER |
|---|---|---|
| D. melanogaster: shepd07053 | Exelixis Collection at Harvard University | P{XP}shepd07053; Flybase: FBst1011268 |
| Oligonucleotides | | |
| Oligos for PCR, cloning and siRNA, see Table S8 | This paper | N/A |
| Recombinant DNA | | |
| Plasmid: pcDNA3 APEX2-NES | (Lam et al., 2015) | Addgene #49386 |
| Plasmid: GFP-Fusion HR Targeting Vector | System Biosciences (SBI) | Cat#HR120PA-1 |
| Plasmid: HR_G38P1-V5-APEX2-GFP | This study | N/A |
| Plasmid: hPGK_V5-APEX2-GFP | This study | N/A |
| Plasmid: pSpCas9(BB)-2A-GFP (PX458) | Gift from Feng Zhang (Ran et al., 2013) | Addgene #48138 |
| Plasmid: pLIX403_UBAP2L_mCherry | This study | N/A |
| Plasmid: pLIX403_AUBA_UBAP2L_mCherry | Thh study | N/A |
| Plasmid: pRSV-Rev | Gift from Didier Trono (Dull et al., 1998) | Addgene #12253 |
| Plasmid: pMDLg/pRRE | Gift from Didier Trono (Dull et al., 1998) | Addgene #12251 |
| Plasmid: pCMV-VSV-G | Gift from Bob Weinberg (Stewart et al.,2003) | Addgene #8154 |
| Software and Algorithms | | |
| Enrichr Gene Set Enrichment Analysis | (Kuleshov et al., 2016) | amp.pharm.mssm.edu/Enrichr/ |
| Cytoscape | (Shannon et al., 2003) | www.cytoscape.org |
| Detecting significant changes in protein abundance | (Kammers et al., 2015) | www.biostat.jhsph.edu/~kkammers/software/eupa/R_guide.html |

REFERENCES

1. Ainger, K., Avossa, D., Morgan, F., Hill, S. J., Barry, C., Barbarese, E., and Carson, J. H. (1993). Transport and localization of exogenous myelin basic protein mRNA microinjected into oligodendrocytes. J. Cell Biol. 123, 431-441.
2. Alami, N. H., Smith, R. B., Carrasco, M. A., Williams, L. A., Winborn, C. S., Han, S. S. W., Kiskinis, E., Winborn, B., Freibaum, B. D., Kanagaraj, A., et al. (2014). Axonal transport of TDP-43 mRNA granules is impaired by ALS-causing mutations. Neuron 81, 536-543.
3. Aulas, A., Fay, M. M., Lyons, S. M., Achorn, C. A., Kedersha, N., Anderson, P., and Ivanov, P. (2017). Stress-specific differences in assembly and composition of stress granules and related foci. J. Cell Sci. 130, 927-937.
4. Becker, L. A., Huang, B., Bieri, G., Ma, R., Knowles, D. A., Jafar-Nejad, P., Messing, J., Kim, H. J., Soriano, A., Auburger, G., et al. (2017). Therapeutic reduction of ataxin-2 extends lifespan and reduces pathology in TDP-43 mice. Nature 544, 367-371.
5. Beckmann, B. M., Horos, R., Fischer, B., Castello, A., Eichelbaum, K., Alleaume, A. M., Schwarzl, T., Curk, T., Foehr, S., Huber, W., et al. (2015). The RNA-binding proteomes from yeast to man harbour conserved enigmRBPs. Nat. Commun. 6,10127.
6. Behrends, C., Sowa, M. E., Gygi, S. P., and Harper, J. W. (2010). Network organization of the human autophagy system. Nature 466,68-76.
7. Blokhuis, A. M., Koppers, M., Groen, E. J., van den Heuvel, D. M., Dini Modigliani, S., Anink, J. J., Fumoto, K., van Diggelen, F., Snelting, A., Sodaar, P., et al. (2016). Comparative interactomics analysis of different ALS-associated proteins identifies converging molecular pathways. Acta Neuropathol. 132,175-196.
8. Boeynaems, S., Bogaert, E., Kovacs, D., Konijnenberg, A., Timmerman, E., Volkov, A., Guharoy, M., De Decker, M., Jaspers, T., Ryan, V. H., et al. (2017). Phase separation of C9orf72 dipeptide repeats perturbs stress granule dynamics. Mol. Cell 65,1044-1055.
9. Brannan, K. W., Jin, W., Huelga, S. C., Banks, C.A., Gilmore, J. M., Florens, L., Washburn, M. P., Van Nostrand, E. L., Pratt, G. A., Schwinn, M. K., et al. (2016). SONAR discovers RNA-binding proteins from analysis of large-scale proteinprotein interactomes. Mol. Cell 64,282-293.
10. Buchan, J. R., Kolaitis, R. M., Taylor, J. P., and Parker, R. (2013). Eukaryotic stress granules are cleared by autophagy and Cdc48/VCP function. Cell 153, 1461-1474.
11. Ciechanover, A., and Kwon, Y. T. (2017). Protein quality control by molecular chaperones in neurodegeneration. Front. Neurosci. 11, 185.
12. Conrad, T., Albrecht, A. S., de Melo Costa, V. R., Sauer, S., Meierhofer, D., and Orom, U. A. (2016). Serial interactome capture of the human cell nucleus. Nat. Commun. 7, 11212.
13. Cox, J., and Mann, M. (2008). MaxQuant enables high peptide identification rates, individualized p.p.b.-range mass accuracies and proteome-wide protein quantification. Nat. Biotechnol. 26, 1367-1372.
14. Du, Z. W., Chen, H., Liu, H., Lu, J., Qian, K., Huang, C. L., Zhong, X., Fan, F., and Zhang, S. C. (2015). Generation and expansion of highly pure motor neuron progenitors from human pluripotent stem cells. Nat. Commun. 6, 6626.
15. Dull, T., Zufferey, R., Kelly, M., Mandel, R.J., Nguyen, M., Trono, D., and Naldini, L. (1998). A third-generation lentivirus vector with a conditional packaging system. J. Virol. 72, 8463-8471.
16. Freibaum, B. D., Chitta, R. K., High, A. A., and Taylor, J. P. (2010). Global analysis of TDP-43 interacting proteins reveals strong association with RNA splicing and translation machinery. J. Proteome Res. 9, 1104-1120.
17. Gendron, J. M., Webb, K., Yang, B., Rising, L., Zuzow, N., and Bennett, E. J. (2016). Using the ubiquitin-modified proteome to monitor distinct and spatially restricted protein homeostasis dysfunction. Mol. Cell. Proteomics 15, 2576-2593.
18. Gore, A., Li, Z., Fung, H. L., Young, J. E., Agarwal, S., Antosiewicz-Bourget, J., Canto, I., Giorgetti, A., Israel, M. A., Kiskinis, E., et al. (2011). Somatic coding mutations in human induced pluripotent stem cells. Nature 471, 63-67.
19. Hung, V., Zou, P., Rhee, H. W., Udeshi, N. D., Cracan, V., Svinkina, T., Carr, S. A., Mootha, V. K., and Ting, A. Y. (2014). Proteomic mapping of the human mitochondrial intermembrane space in live cells via ratiometric APEX tagging. Mol. Cell 55, 332-341.
20. Jain, S., Wheeler, J. R., Walters, R. W., Agrawal, A., Barsic, A., and Parker, R. (2016). ATPase-modulated stress granules contain a diverse proteome and substructure. Cell 164, 487-498.
21. Kammers, K., Cole, R. N., Tiengwe, C., and Ruczinski, I. (2015). Detecting significant changes in protein abundance. EuPA Open Proteom. 7, 11-19.
22. Kato, M., Han, T. W., Xie, S., Shi, K., Du, X., Wu, L. C., Mirzaei, H., Goldsmith, E. J., Longgood, J., Pei, J., et al. (2012). Cell-free formation of RNA granules: low complexity sequence domains form dynamic fibers within hydrogels. Cell 149, 753-767.
23. Kedersha, N., and Anderson, P. (2002). Stress granules: sites of mRNA triage that regulate mRNA stability and translatability. Biochem. Soc. Trans. 30, 963-969.
24. Kedersha, N. L., Gupta, M., Li, W., Miller, I., and Anderson, P. (1999). RNAbinding proteins TIA-1 and TIAR link the phosphorylation of eIF-2 alpha to the assembly of mammalian stress granules. J. Cell Biol. 147, 1431-1442.
25. Kuleshov, M. V., Jones, M. R., Rouillard, A. D., Fernandez, N. F., Duan, Q., Wang, Z., Koplev, S., Jenkins, S. L., Jagodnik, K. M., Lachmann, A., et al. (2016). Enrichr: a comprehensive gene set enrichment analysis web server 2016 update. Nucleic Acids Res. 44 (W1), W90-7.
26. Lagier-Tourenne, C., Baughn, M., Rigo, F., Sun, S., Liu, P., Li, H. R., Jiang, J., Watt, A. T., Chun, S., Katz, M., et al. (2013). Targeted degradation of sense and antisense C9orf72 RNA foci as therapy for ALS and frontotemporal degeneration. Proc. Natl. Acad. Sci. USA 110, E4530-E4539.
27. Lam, S. S., Martell, J. D., Kamer, K. J., Deerinck, T. J., Ellisman, M. H., Mootha, V. K., and Ting, A. Y. (2015). Directed evolution of APEX2 for electron microscopy and proximity labeling. Nat. Methods 12, 51-54.
28. Lanson, N. A., Jr., Maltare, A., King, H., Smith, R., Kim, J. H., Taylor, J. P., Lloyd, T. E., and Pandey, U.B. (2011). A Drosophila model of FUS-related neurodegeneration reveals genetic interaction between FUS and TDP-43. Hum. Mol. Genet. 20, 2510-2523.
29. Lee, K., Zhang, P., Kim, H. J., Mitrea, D. M., Sarkar, M., Freibaum, B. D., Cika, J., Coughlin, M., Messing, J., Molliex, A., et al. (2016). C9orf72 dipeptide repeats impair the assembly, dynamics, and function of membrane-less organelles. Cell 167, 774-788.
30. Lin, Y., Mori, E., Kato, M., Xiang, S., Wu, L., Kwon, I., and McKnight, S. L. (2016). Toxic PR poly-dipeptides encoded by the C9orf72 repeat expansion target LC domain polymers. Cell 167, 789-802.
31. Mackenzie, I. R., Nicholson, A. M., Sarkar, M., Messing, J., Purice, M. D., Pottier, C., Annu, K., Baker, M., Perkerson, R. B., Kurti, A., et al. (2017). TIA1 mutations in amyotrophic lateral sclerosis and frontotemporal dementia promote phase separation and alter stress granule dynamics. Neuron 95, 808-816.
32. March, Z. M., King, O. D., and Shorter, J. (2016). Prion-like domains as epigenetic regulators, scaffolds for subcellular organization, and drivers of neurodegenerative disease. Brain Res. 1647, 9-18.
33. Margolin, A. A., Ong, S. E., Schenone, M., Gould, R., Schreiber, S. L., Carr, S. A., and Golub, T. R. (2009). Empirical Bayes analysis of quantitative proteomics experiments. PLoS ONE 4, e7454.
34. Martinez, F. J., Pratt, G. A., Van Nostrand, E. L., Batra, R., Huelga, S. C., Kapeli, K., Freese, P., Chun, S. J., Ling, K., Gelboin-Burkhart, C., et al. (2016). ProteinRNA networks regulated by normal and ALS-associated mutant HNRNPA2B1 in the nervous system. Neuron 92, 780-795.
35. Molliex, A., Temirov, J., Lee, J., Coughlin, M., Kanagaraj, A. P., Kim, H. J., Mittag, T., and Taylor, J. P. (2015). Phase separation by low complexity domains promotes stress granule assembly and drives pathological fibrillization. Cell 163, 123-133.
36. Murakami, T., Qamar, S., Lin, J. Q., Schierle, G. S., Rees, E., Miyashita, A., Costa, A. R., Dodd, R. B., Chan, F. T., Michel, C. H., et al. (2015). ALS/FTD mutation-induced phase transition of FUS liquid droplets and reversible hydrogels into irreversible hydrogels impairs RBP granule function. Neuron 88, 678-690.
37. Ohn, T., Kedersha, N., Hickman, T., Tisdale, S., and Anderson, P. (2008). A functional RNAi screen links O-GlcNAc modification of ribosomal proteins to stress granule and processing body assembly. Nat. Cell Biol. 10, 1224-1231.
38. Patel, A., Lee, H. O., Jawerth, L., Maharana, S., Jahnel, M., Hein, M. Y., Stoynov, S., Mahamid, J., Saha, S., Franzmann, T. M., et al. (2015). A liquidto-solid phase transition of the ALS protein FUS accelerated by disease mutation. Cell 162, 1066-1077.
39. Perez-Gonzalez, A., Pazo, A., Navajas, R., Ciordia, S., Rodriguez-Frandsen, A., and Nieto, A. (2014). hCLE/C14orf166 associates with DDX1-HSPC117FAM98B in a novel transcription-dependent shuttling RNA-transporting complex. PLoS ONE 9, e90957.
40. Periz, G., Lu, J., Zhang, T., Kankel, M. W., Jablonski, A. M., Kalb, R., McCampbell, A., and Wang, J. (2015). Regulation of protein quality control by UBE4B and LSD1 through p53-mediated transcription. PLoS Biol. 13, e1002114.
41. Ran, F. A., Hsu, P. D., Wright, J., Agarwala, V., Scott, D. A., and Zhang, F. (2013). Genome engineering using the CRISPR-Cas9 system. Nat. Protoc. 8, 2281-2308.
42. Reinhardt, P., Glatza, M., Hemmer, K., Tsytsyura, Y., Thiel, C. S., Hoing, S., Moritz, S., Parga, J. A., Wagner, L., Bruder, J. M., et al. (2013). Derivation and expansion using only small molecules of human neural progenitors for neurodegenerative disease modeling. PLoS ONE 8, e59252.
43. Rhee, H. W., Zou, P., Udeshi, N. D., Martell, J. D., Mootha, V. K., Carr, S. A., and Ting, A. Y. (2013). Proteomic mapping of mitochondria in living cells via spatially restricted enzymatic tagging. Science 339, 1328-1331.
44. Ritson, G. P., Custer, S. K., Freibaum, B. D., Guinto, J. B., Geffel, D., Moore, J., Tang, W., Winton, M. J., Neumann, M., Trojanowski, J. Q., et al. (2010). TDP-43 mediates degeneration in a novel Drosophila model of disease caused by mutations in VCP/p97. J. Neurosci. 30, 7729-7739.

45. Salminen, A., and Kaarniranta, K. (2012). AMP-activated protein kinase (AMPK) controls the aging process via an integrated signaling network. Ageing Res. Rev. 11, 230-241.
46. Shannon, P., Markiel, A., Ozier, O., Baliga, N. S., Wang, J. T., Ramage, D., Amin, N., Schwikowski, B., and Ideker, T. (2003). Cytoscape: a software environment for integrated models of biomolecular interaction networks. Genome Res. 13, 2498-2504.
47. Smith, B. N., Topp, S. D., Fallini, C., Shibata, H., Chen, H. J., Troakes, C., King, A., Ticozzi, N., Kenna, K. P., Soragia-Gkazi, A., et al. (2017). Mutations in the vesicular trafficking protein annexin A11 are associated with amyotrophic lateral sclerosis. Sci. Transl. Med. 9, eaad9157.
48. Smyth, G. K. (2004). Linear models and empirical Bayes methods for assessing differential expression in microarray experiments. Stat. Appl. Genet. Mol. Biot 3, Article3.
49. Stewart, S. A., Dykxhoorn, D. M., Palliser, D., Mizuno, H., Yu, E. Y., An, D. S., Sabatini, D. M., Chen, I. S., Hahn, W. C., Sharp, P. A., et al. (2003). Lentivirus-delivered stable gene silencing by RNAi in primary cells. RNA 9, 493-501.
50. Storey, J. D., and Tibshirani, R. (2003). Statistical significance for genomewide studies. Proc. Natl. Acad. Sci. USA 100, 9440-9445.
51. Sundararaman, B., Zhan, L., Blue, S. M., Stanton, R., Elkins, K., Olson, S., Wei, X., Van Nostrand, E. L., Pratt, G. A., Huelga, S. C., et al. (2016). Resources for the comprehensive discovery of functional RNA elements. Mol. Cell 61, 903-913.
52. Wheeler, J. R., Matheny, T., Jain, S., Abrisch, R., and Parker, R. (2016). Distinct stages in stress granule assembly and disassembly. eLife 5, e18413.
53. Yang, D., Abdallah, A., Li, Z., Lu, Y., Almeida, S., and Gao, F. B. (2015). FTD/ALS-associated poly(GR) protein impairs the Notch pathway and is recruited by poly(GA) into cytoplasmic inclusions. Acta Neuropathol. 130, 525-535.
54. Yasuda, K., and Mili, S. (2016). Dysregulated axonal RNA translation in amyotrophic lateral sclerosis. Wiley Interdiscip. Rev. RNA 7, 589-603.

What is claimed is:

1. A method for inhibiting the formation of a toxic insoluble protein aggregate stress granule (SG) comprising a ubiquitin associated protein 2-like (UBAP2L) protein in a mammalian neuronal cell, the method comprising contacting the cell with an effective amount of an antisense oligonucleotide (ASO) or an RNA interference (RNAi) molecule that hybridizes to a region within an mRNA encoding a UBAP2L protein.

2. The method of claim 1, wherein the mammalian neuronal cell is a spinal group neuron or a brain neuron.

3. The method of claim 1, further comprising subjecting the cell to an environmental stressor.

4. The method of claim 1, further comprising detecting SG formation.

5. A method for inhibiting the formation of stress granules in a neuronal cell of a subject suffering from amyotrophic lateral sclerosis (ALS), comprising administering to the subject an effective amount of an antisense oligonucleotide (ASO) or an RNA interference (RNAi) molecule that hybridizes to a region within an mRNA encoding a UBAP2L protein.

6. The method of claim 1, wherein the ASO does not hybridize to a region of the mRNA that encodes for an ubiquitin associated (UBA) domain or arginine and glycine-rich motif (RGG domain).

7. The method of claim 1, wherein the RNAi molecule comprises the oligonucleotide sequence of SEQ ID NO: 1 or SEQ ID NO: 2 or an oligonucleotide having at least 95% sequence identity thereto.

8. The method of claim 1, wherein the RNAi molecule does not hybridize to a region of the mRNA that encodes for an ubiquitin associated (UBA) domain or arginine and glycine-rich motif (RGG domain).

9. The method of claim 5, wherein the RNAi molecule comprises the nucleotide sequence of SEQ ID NO: 1 or SEQ ID NO: 2 or an oligonucleotide having at least 95% sequence identity thereto.

10. The method of claim 5, wherein the ASO does not hybridize to a region of the UBAP2L mRNA molecule that encodes for an ubiquitin associated (UBA) domain or arginine and glycine-rich motif (RGG domain).

11. The method of claim 5, wherein the RNAi molecule does not hybridize to a region of the mRNA that encodes for an ubiquitin associated (UBA) domain or arginine and glycine-rich motif (RGG domain).

12. The method of claim 2, wherein the RNAi molecule comprises the oligonucleotide sequence of SEQ ID NO: 1 or SEQ ID NO: 2 or an oligonucleotide having at least 95% sequence identity thereto.

\* \* \* \* \*